US008163502B2

(12) United States Patent
Denny et al.

(10) Patent No.: US 8,163,502 B2
(45) Date of Patent: *Apr. 24, 2012

(54) METHOD FOR PREDICTING THE RISK OF DISEASE BASED ON LECTIN BINDING

(75) Inventors: Patricia Denny, Los Angeles, CA (US); Paul C. Denny, Los Angeles, CA (US); Mahvash Navazesh, Los Angeles, CA (US)

(73) Assignees: Proactive Oral Solutions, Inc., Long Beach, CA (US); University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/786,395

(22) Filed: May 24, 2010

(65) Prior Publication Data

US 2010/0233185 A1 Sep. 16, 2010

Related U.S. Application Data

(63) Continuation of application No. 10/551,612, filed as application No. PCT/US2004/010169 on Apr. 1, 2004, now Pat. No. 7,736,857.

(60) Provisional application No. 60/459,878, filed on Apr. 1, 2003.

(51) Int. Cl.
*G01N 33/53* (2006.01)
*G01N 33/543* (2006.01)

(52) U.S. Cl. ......... 435/7.1; 436/501; 436/518; 436/827; 435/7.34

(58) Field of Classification Search ............. None
See application file for complete search history.

(56) References Cited

U.S. PATENT DOCUMENTS

| | | | |
|---|---|---|---|
| 4,217,341 A | 8/1980 | Suddick et al. | |
| 4,444,879 A * | 4/1984 | Foster et al. | 435/7.95 |
| 4,582,795 A * | 4/1986 | Shibuya et al. | 435/34 |
| 4,692,407 A | 9/1987 | Jordan et al. | |
| 4,725,576 A | 2/1988 | Pollock et al. | |
| 4,768,238 A | 9/1988 | Kleinberg et al. | |
| 5,013,542 A | 5/1991 | Hay et al. | |
| 5,103,836 A | 4/1992 | Goldstein et al. | |
| 5,112,758 A | 5/1992 | Fellman et al. | |
| 5,268,148 A | 12/1993 | Seymour | |
| 5,335,673 A | 8/1994 | Goldstein et al. | |
| 5,356,782 A | 10/1994 | Moorman et al. | |
| 5,374,538 A | 12/1994 | Bratthall | |
| 5,376,532 A | 12/1994 | Singer, Jr. | |
| 5,486,503 A | 1/1996 | Oppenheim et al. | |
| 5,585,241 A * | 12/1996 | Lindmo | 435/6 |
| 5,631,228 A | 5/1997 | Oppenheim et al. | |
| 5,646,119 A | 7/1997 | Oppenheim et al. | |
| 5,695,929 A | 12/1997 | Goldstein | |
| 5,714,341 A | 2/1998 | Thieme et al. | |
| 5,736,322 A | 4/1998 | Goldstein | |
| 5,736,341 A | 4/1998 | Sorsa et al. | |
| 5,756,361 A | 5/1998 | Winterbottom et al. | |
| 5,801,226 A | 9/1998 | Cummins et al. | |
| 5,807,541 A | 9/1998 | Aberg et al. | |
| 5,830,489 A | 11/1998 | Valenti et al. | |
| 5,866,432 A | 2/1999 | Sorsa et al. | |
| 5,885,965 A | 3/1999 | Oppenheim et al. | |
| 5,886,054 A | 3/1999 | Van Nieuw Amerongen et al. | |
| 5,910,122 A | 6/1999 | D'Angelo | |
| 5,912,230 A | 6/1999 | Oppenheim et al. | |
| 5,968,746 A | 10/1999 | Schneider | |
| 6,063,588 A | 5/2000 | Lamster | |
| 6,130,042 A | 10/2000 | Diehl et al. | |
| 6,136,298 A | 10/2000 | Gaffar et al. | |
| 6,230,052 B1 | 5/2001 | Wolff et al. | |
| 6,231,857 B1 | 5/2001 | Shi et al. | |
| 6,436,721 B1 | 8/2002 | Kuo et al. | |
| 7,736,857 B2 * | 6/2010 | Denny et al. | 435/7.1 |
| 2002/0177171 A1 | 11/2002 | Stromberg | |
| 2003/0040009 A1 | 2/2003 | Denny et al. | |

FOREIGN PATENT DOCUMENTS

WO    WO 94/06012    3/1994
WO    WO 97/09620    3/1997

OTHER PUBLICATIONS

Seemann et al. (Caries Research, 2001, vol. 35, pp. 156-161).*
Akintoye et al. (Archives of Oral Biology, vol. 47, 2002, pp. 337-345).*
Sharon (1996, Adv Exp Med Biol, vol. 408, pp. 1-8).*
W.R. Hume (Journal of Dental Education, vol. 57, No. 6, Jun. 1993, pp. 439-443).*
Newbrun, E., and Leverett, D. (1990). "Risk assessment dental caries working group summary statement." In Risk Assessment in Dentistry. J.D. Bader, ed., Chapel Hill, N.C.: University of North Carolina, pp. 304-305.
Nielsen, P.A., et al. (1996). "Differential expression of human high-molecular-weight salivary mucin (MG1) and low-molecular-weight salivary mucin (MG2)." J Dent Res. 75(11):1820-1826.
Nolan, A., et al. (1991). "Recurrent aphthous ulceration: vitamin B1, B2 and B6 status and response to replacement therapy." J Oral Pathol Med. 20(8):389-391.
Offenbacher, S., et al. (1996). Periodontal infection as a possible risk factor for preterm low birth weight. J Periodontol. 67(10 Suppl):1103-1113.
Offner, G.D., and Troxler, R.F. (2000). "Heterogeneity of high-molecular-weight human salivary mucins." Adv Dent Res. 14:69-75.
Oxholm, P., and Asmussen, K. (1996). "Primary Sjögren's syndrome: the challenge for classification of disease manifestations." J Intern Med. 239(6):467-474.
Park, N.H., et al. (1995). "Combined oral carcinogenicity of HPV-16 and benzo(α)pyrene: an in vitro multistep carcinogenesis model." Oncogene. 10(11):2145-2153.

(Continued)

*Primary Examiner* — Lisa Cook
(74) *Attorney, Agent, or Firm* — VLP Law Group LLP; Richard G. A. Bone

(57) ABSTRACT

Provided are methods, test devices, and diagnostic kits for predicting, assessing, and diagnosing the risk of a disease using salivary analysis. The methods comprise providing a whole (unfractionated) saliva sample from a subject; contacting an aliquot of the saliva with two or more lectins under conditions that allow the two or more lectins to bind to a lectin-binding component of the saliva; detecting the amount of bound lectin; and comparing the amount of bound lectin to the amount known to bind a saliva sample from a control patient, to predict the risk of a disease in the subject. Also provided are methods for reducing the risk of a disease and a method for assessing the risk of the disease at a defined level.

26 Claims, 18 Drawing Sheets

OTHER PUBLICATIONS

Payne, J.B., et al. (1997). "The association between estrogen status and alveolar bone density changes in postmenopausal women with a history of periodontitis." J Periodontol. 68(1)24-31.

Powell, L.V. (1998). "Caries prediction: a review of the literature." Community Dent Oral Epidemiol. 26(6):361-371.

Prakobphol, A., et al. (1999). "Separate oligosaccharide determinants mediate interactions of the low-molecular-weight salivary mucin with neutrophils and bacteria." Biochemistry. 38(21):6817-6825.

Rayment, S.A., et al. (2000). "Immunoquantification of human salivary mucins MG1 and MG2 in stimulated whole saliva: factors influencing mucin levels." J Dent Res. 79(10):1765-1772.

Romero, R., et al. (1993). "The relationship between spontaneous rupture of membranes, labor, and microbial invasion of the amniotic cavity and amniotic fluid concentrations of prostaglandins and thromboxane B2 in term pregnancy." Am J Obstet Gynecol. 168(6 Pt 1):1654-1668.

Saah, A.J., et al. (1992). "Predictors of the risk of development of acquired immunodeficiency syndrome within 24 months among gay men seropositive for human immunodeficiency virus type 1: a report from the Multicenter AIDS Cohort Study." Am J Epidemiol. 135(10):1147-1155.

Samaranayake, L.P., and Holmstrup, P. (1989). "Oral candidiasis and human immunodeficiency virus infection." J Oral Pathol Med. 18(10):554-564.

Scannapieco, F.A., et al. (1998). "Associations between oral conditions and respiratory disease in a national sample survey population." Ann Periodontol. 3(1):251-256.

Scannapieco, F.A., and Mylotte, J.M. (1996). "Relationships between periodontal disease and bacterial pneumonia." J Periodontol. 67(10 Suppl):1114-1122.

Schenkein, H.A., and Van Dyke, T.E. (1994). "Early-onset periodontitis: systemic aspects of etiology and pathogenesis." Periodontol 2000 6(1):7-25.

Scully, C., and Porter, S. (1989). "Recurrent aphthous stomatitis: current concepts of etiology, pathogenesis and management." J Oral Pathol Med. 18(1):21-27.

National Institute of Health Consensus Development Panel. National Institutes of Health Consensus Development Conference statement. Diagnosis and management of dental caries throughout life, Mar. 26-28, 2001. J Am Dent Assoc. (2001) 132(8):1153-1161.

Shapiro, S., et al. (1980). "Relevance of correlates of infant deaths for significant morbidity at 1 year of age." Am J Obstet Gynecol. 136(3):363-373.

Woo, S.B., and Sonis, S.T. (1996). "Recurrent aphthous ulcers: a review of diagnosis and treatment." J Am Dent Assoc. 127(8):1202-1213.

Ship, I.I. (1965). "Inheritance of aphthous ulcers of the mouth." J Dent Res. 44(5):837-844.

Socransky, S.S., and Haffajee, A.D. (1992). "The bacterial etiology of destructive periodontal disease: current concepts." J Periodontol. 63(4 Suppl):322-331.

Steinfeld, S., et al. (2000). "Labeled neoglycoproteins and human lectins as diagnostic and potential functional markers in salivary glands of patients with Sjögren's syndrome." J Rheumatol. 27(8):1910-1916.

Strous, G.J., and Dekker, J. (1992). "Mucin-type glycoproteins." Crit Rev Biochem Mol Biol. 27(1-2):57-92.

Sugerman, P.B., and Shillitoe, E.J. (1997). "The high risk human papillomaviruses and oral cancer: evidence for and against a causal relationship." Oral Dis. 3(3):130-147.

Suzuki, J.B. (1988). "Diagnosis and classification of the periodontal diseases." Dent Clin North Am. 32(2):195-216.

Svojanovsky, S.R., et al. (1999). "High sensitivity ELISA determination of taxol in various human biological fluids." J Pharm Biomed Anal. 20(3):549-555.

Syrjänen, S.M., et al. (1988). "Human papillomavirus (HPV) DNA sequences in oral precancerous lesions and squamous cell carcinoma demonstrated by in situ hybridization." J Oral Pathol. 17(6):273-278.

Tanzer, J.M. (1997). "Understanding dental caries: an infectious disease, not a lesion." Internat. J. Oral Biol. 22(4):205-214.

Talal, N. (1992). "Sjögren's syndrome: historical overview and clinical spectrum of disease." Rheum Dis Clin North Am. 18(3):507-515.

Tindall, et al. (1995). "Primary HIV infection: clinical, immunologic, and serologic aspects." Medical Management of AIDS, Sande, et al., eds., pp. 105-129; W.B. Saunders, 1995.

Wintergerst, U., et al. (2000). "Use of saliva specimens for monitoring indinavir therapy in human immunodeficiency virus-infected patients." Antimicrob Agents Chemother. 44(9):2572-2574.

Van Dyke, T.E., et al. (1980). "Neutrophil chemotaxis dysfunction in human periodontitis." Infect Immun. 27 (1):124-132.

Wheeler, Jr., C.E. (1988). "The herpes simplex problem." J Am Acad Dermatol. 18(1 Pt 2):163-168.

Whitley, R.J. (1992). "Neonatal herpes simplex virus infections: pathogenesis and therapy." Pathol Biol (Paris). 40(7):729-734.

Exam report in Australian Patent Application: AU2004227999 from Nov. 30, 2007.

Exam report in Japanese Patent Application: JP2006-509624 from Sep. 3, 2009.

Supplementary European Search Report for Application No. EP 04 75 8774 dated Jan. 22, 2007.

International Preliminary Report on Patentability From Application PCT/US2004/010169 from Jan. 12, 2005.

Miller, A. J., et al. Oral health of United States adults: national findings. National Institute of Dental Research, U.S. Department of Health and Human Services. NIH Publication No. 87:2868, (1987).

Akinyinka, O.O., et al. (2000). The effects of acute falciparum malaria on the disposition of caffeine and the comparison of saliva and plasma-derived pharmacokinetic parameters in adult Nigerians. Eru. J. Clin. Pharmacol. 56(2):159-165.

Astor, F.C., et al. (1999). Xerostomia: a prevalent condition in the elderly. Ear Nose Throat J. 78(7):476-479.

Atkinson, J.C., et al. (1993). "Guidelines for saliva nomenclature and collection," in Saliva as a Diagnostic Fluid, Ann. NY Acad. Sciences 694:xi-xii.

Ayad, M., et al. (2000). The association of basic proline-rich peptides from human parotid gland secretions with caries experience. J. Dent. Res. 79(4):976-982.

Bagán, J.V., et al. (1991). Recurrent aphthous stomatitis. A study of the clinical characteristics of lesions in 93 cases. J. Oral Pathol. Med. 20(8):395-397.

C. Baldwin, et al., (2000) "Analysis of pigeon intestinal mucin allergens using a novel dot blot assay," Carbohydrate Research, 326:43-49.

L. Baughan, et al.,(2000) "Salivary mucin as related to oral Streptococcus mutans in elderly people," Oral Microbiology and Immunology, 15:10-14.

Beck, J.D. (1996). "Periodontal implications: older adults." Ann. Periodontol 1(1):322-357.

Beck, J., et al. (1996). Periodontal disease and cardiovascular disease. J. Periodontol 67(10 Suppl):1123-1137.

Belce, A. et al. (2000). Evaluation of salivary sialic acid level and Cu—Zn superoxide dismutase activity in type 1 diabetes mellitus. Tohoku J. Exp. Med. 192(3):219-225.

Bobek, L.A., et al. (1996). "Structure and chromosomal localization of the human salivary mucin gene, MUC7. Genomics." 31(3):277-282.

Bolscher, J.G., et al. (1999). "Detection and quantification of MUC7 in submandibular, sublingual, palatine, and labial saliva by antipeptide antiserum." J. Dent. Res. 78(7):1362-1369.

Caton, J. (1989). "Periodontal diagnosis and diagnostic aids." In Proceedings of the World Workshop in Clinical Periodontics. M. Nevins, W. Becker, and K. Kornman, Eds., Princeton, NJ: American Academy of Periodontology; 1:1-22.

Chang, F., et al. (1990). "Detection of human papillomavirus (HPV) DNA in oral squamous cell carcinomas by in situ hybridization and polymerase chain reaction." Arch. Dermatol. Res. 282(8):493-497.

Daniels, T.E., and Fox, P.C. (1992). "Salivary and oral components of Sjögren's syndrome." Rheum Dis Clin North Am. 18(3):571-589.

de Villiers, E.M. (1989). "Papilloma viruses in cancers and papillomas of the aerodigestive tract." Biomed Pharmacother. 43(1):31-36.

Denny, P.C., et al. (2006). "A novel saliva test for caries risk assessment." CDA Journal 34(4):287-290, 292-294.

Dusek, M., et al. (1996). "Masticatory function in patients with xerostomia." Gerodontology 13(1):3-8.

Ellen, R.P. (1976). "Microbiological assays for dental caries and periodontal disease susceptibility." Oral Sci Rev. 1976(8):3-23.

Epstein, J.B., and Scully, C. (1992). "Neoplastic disease in the head and neck of patients with AIDS." Int J Oral Maxillofac Surg. 21(4):219-226.

"Evidence Report/Technology Assessment, No. 36: Diagnosis and Management of Dental Caries" (U.S. Dept. of Health & Human Services. National Institutes of Health Consensus Development Conference Statement. Diagnosis and Management of Dental Caries Throughout Life AHRQ Pub. No. 01-E041, Mar. 2001, pp. 1-8.

Ferguson, D.B. (1987). "Current diagnostic uses of saliva." J. Dent. Res. 66(2):420-424.

Ferguson, M.M., et al. (1984). "An epidemiological study of factors associated with recurrent aphthae in women." J. Oral Med. 39(4):212-217.

Fox, P.C., et al. (1985). "Xerostomia: evaluation of a symptom with increasing significance." J Am Dent Assoc. 110(4):519-525.

Franceschi, S., et al. (1996). "Human papillomavirus and cancers of the upper aerodigestive tract: a review of epidemiological and experimental evidence." Cancer Epidemiol Biomarkers Prev. 5(7):567-575.

Genco, R.J. (1990). "Classification of clinical and radiographic features of periodontal diseases." In Genco, R., Goldman, H., Cohen, W., eds. Contemporary Periodontics. St. Louis: pp. 63-81.

Genco, R.J. (1996). "Current view of risk factors for periodontal diseases." J Periodontol. 67(10 Suppl):1041-1049.

Gendler, S.J., and Spicer, A.P. (1995). "*Epithelial mucin* genes." Annu Rev Physiol. 57(3):607-634.

Gibbs, R.S., et al. (1992). "A review of premature birth and subclinical infection." Am J Obstet Gynecol. 166(5):1515-1528.

Diabetes statistics. NIH Publication No. 99-3892. Bethesda, MD: National Institute of Diabetes and Digestive and Kidney Diseases, Mar. 1999.

Hayes, C., et al. (1998). "The association between alveolar bone loss and pulmonary function: the VA dental longitudinal study." Ann Periodontol. 3(1):257-261.

Hillier, S.L., et al. (1988). "A case-control study of chorioamnionic infection and histologic chorioamnionitis in prematurity." N Engl J Med. 319(15):972-978.

Hillier, S.L., et al. (1995). "Association between bacterial vaginosis and preterm delivery of a low-birth-weight infant." N Engl J Med. 333(26)1737-1742.

Navazesh, M. (1993). "Methods for collecting saliva." Ann NY Acad Sci. 694:72-77.

Igarashi, T., et al. (1996). Direct detection of Streptococcus mutans in human dental plaque by polymerase chain reaction. Oral Microbiol Immunol. 11(5):294-298.

Institute of Medicine, Committee to Study the Prevention of Low Birth Weight, Division of Health. Promotion and Disease Progression. Preventing low birth weight. Washington: National Academy Press (1985), pp. R1-R6, 1-37.

Klein, A., et al. (1992). "Progress of HIV infection and changes in the lipid membrane structure of CD4+ cells." AIDS 6(3):332-333.

Kline, M.W. (1996). "Oral manifestiations of pediatric human immunodeficiency virus infection: a review of the literature." Pediatrics. 97(3):380-388.

Lenander-Lumikari, M., and Loimaranta, V. (2000). "Saliva and dental caries." Adv Dent Res. 14:40-47.

Lehner, T. (1968). "Autoimmunity in oral diseases, with special reference to recurrent oral ulceration." Proc R Soc Med. 61(5):515-524.

Löe, H. (1993). "Periodontal disease. The sixth complication of diabetes mellitus." Diabetes Care. 16(1):329-334.

Mandel, I.D., and Gaffar, A. (1986). "Calculus revisited. A review." J Clin Periodontol. 13(4):249-257.

Mandel, I.D. (1993). "Salivary diagnosis: promises, promises." Ann N Y Acad Sci. 694:1-10.

Mandel, I.D. (1995). "Calculus update: prevalence, pathogenicity and prevention." J Am Dent Assoc. 126(5):573-580.

Mealey, B.L. (1996). "Periodontal implications: medically compromised patients." Ann Periodontol. 1(1):256-321.

McCullough, M.J., et al. (1996). "*Candida albicans*: a review of its history, taxonomy, epidemiology, virulence attributes, and methods of strain differentiation." Int J Oral Maxillofac Surg. 25(2):136-144.

Najera, M.P., et al. (1997). "Prevalence of periodontal disease in patients with Sjögren's syndrome." Oral Surg Oral Med Oral Pathol Oral Radiol Endod. 83(4):453-457.

* cited by examiner

METHOD FOR PREDICTING THE RISK OF DISEASE BASED ON LECTIN BINDING

RELATED APPLICATIONS

This application claims priority to U.S. Provisional Application Ser. No. 60/459,878, filed Apr. 1, 2003, the content of which is incorporated herein by reference. This application is a continuation of application Ser. No. 10/551,612 now U.S. Pat. No. 7,736,857 which is a 371 of PCT/US2004/010169 filed on Apr. 1, 2004, both of which are incorporated herein by reference.

ACKNOWLEDGMENT

This invention was made with government support under STTR Grant Number 2 R42 DE014650, awarded by the National Institutes of Health. The Government has certain rights in the invention.

FIELD OF THE INVENTION

This present invention provides methods and test devices for predicting, assessing, and diagnosing the risk of a disease using salivary analysis.

BACKGROUND OF THE INVENTION

Insight into a wide range of clinical situations may be gained from salivary analysis (See e.g., Mandel, I. D., "Salivary Diagnosis: Promises, Promises," in Saliva as a Diagnostic Fluid, Malamud et al., eds., Ann. NY Acad. Sciences 694: 1-10 (1993)). The earliest sialochemical studies on oral fluids examined saliva for specific components that would be diagnostic for various systemic conditions, including gout and rheumatism. (Atkinson, et al., "Guidelines for Saliva Nomenclature and Collection," in Saliva as a Diagnostic Fluid, Ann. NY Acad. Sciences 694: xi-xii (1993)). A recent example utilizes salivary acetaminophen concentration to assess the gastric emptying rate of liquids. A number of studies report using saliva specimens for monitoring pharmaceuticals and chemicals, including taxol (Svojanovsky, et al., *J. Pharm. Biomed. Anal.*, 20:549-555 (1999)); caffeine (Akinyinka, et al., *Eur. J. Clin. Pharmacol.*, 56:159-165 (2000)); and the protease inhibitor, indinavir (Wintergerst, et al., *Antimicrobial Agents and Chemotherapy*, 44:2572-2574 (2000)).

In general, the analysis of saliva for diagnostic purposes has been directed towards evaluating systemic disease (e.g., Sjogren's syndrome, cystic fibrosis, HIV infection, etc.), or as a means of determining systemic levels of therapeutic drugs such as steroids (Ferguson, *J. Dent. Res.* 66(2): 420-424 (1987)). There have also been many attempts to measure other factors in saliva and then relate them to oral diseases. For example, salivary analysis has also been used to diagnose periodontal disease (U.S. Pat. No. 6,063,588 to Lamster; U.S. Pat. No. 5,376,532 to Singer, Jr.; U.S. Pat. Nos. 5,866,432 and 5,736,341 to Sorsa, et al.; and U.S. Pat. No. 5,756,361 to Winterbottom, et al.). However, the vast majority of studies have not been able to relate factors in saliva with other common oral diseases such as dental caries. These studies reported values for pH, various ions, macromolecules, and flow rate, but found little evidence of a correlation. The few studies that have shown a small amount of correlation were found not to correlate with other studies. Thus, there remains a need for a saliva-based test for predicting the risk of oral diseases and associated diseases that is simple and accurate.

I. Oral Diseases and Associated Diseases

The most common oral diseases are dental caries and the periodontal diseases. Individuals are vulnerable to dental caries throughout life, affecting 85 percent of adults aged 18 and older. Periodontal diseases are most often seen in maturity, with the majority of adults experiencing some signs and symptoms by the mid-30s. Certain rare forms of periodontal disease affect young people. Oral disorders also include certain mucosal infections, as well as oral and pharyngeal cancers and precancerous lesions.

A. Dental Caries

Caries is a unique multifactorial infectious disease (Lenander-Lumikari, et al., Adv. Dent. Res. 14:40-47 (December 2000)). Dental caries affects teeth at all levels and can cause extensive crown mutilations, bacterial disorders of the periapical tissues, or even loss of the affected dental elements. Clinically, the disease is characterized by demineralization of the dental enamel and of the dentin in various stages of progress, until it affects the pulp space. When the lesion passes beyond the enamel-dentin border, a phlogistic reaction of the pulp tissues is constantly observed, with the formation of reaction dentin in some cases. Approximately 50% of adult individuals have at least four caries-related lesions that are treated and require treatment, and approximately 30% of adult individuals have over 50% of their teeth affected by caries (U.S. Pat. No. 5,830,489 to Valenti, et al.).

The bacterium *Streptococcus mutans*, or *S. mutans*, is known to be a prime etiologic agent for the initiation and progression of human dental caries, or cavities. *S. mutans* is one of the primary factors in acid dissolution of the apatite (mineral) component of the enamel then the dentin, or of the cementum then the dentin (Tanzer, J. M., *Inter. J. Oral Biol.* 22:205-214 (1997)). A strong correlation between the proportion of *S. mutans* in dental plaque or in saliva relative to other bacterial species and the presence or risk of future outbreaks of dental caries has been documented (Tanzer, J. M., supra). Therefore, *S. mutans* in plaque or saliva may serve as an index for both caries activity state and caries risk or susceptibility. These indices play an increasingly important role in the diagnosis and treatment of dental caries (Hume, W. R., *J. Dent. Educ.* 57:439-443 (1993)).

Present techniques for detecting and quantitatively determining *S. mutans* include bacterial culture with selective media using either broth or agar plate systems, and polymerase chain reaction techniques (Ellen, R. P., *Oral Sci. Rev.* 8:3-23 (1976); Igarashi, et al., *Oral Microbiol. and Immunol.* 11:294-298 (1996); U.S. Pat. No. 5,374,538 to Bratthall; U.S. Pat. No. 4,692,407 to Jordan, et al.). However, each of these methods require significant time (on the order of days), well trained personnel and sophisticated equipment to perform. Consequently, existing techniques are relatively expensive and time consuming. Moreover, the use of the titer of *S. mutans* in the oral cavity as a predictor of caries risk is consistently significant only within the first two years of age.

Human dental caries may also be detected by changes in translucency, color, hardness or X-ray density of teeth. However, these technologies have limitations both in specificity and reproducibility. Furthermore, they do not show whether or not the disease is active at a single time point (U.S. Pat. No. 6,231,857 to Shi, et al.).

B. Periodontal Diseases

Like dental caries, the periodontal diseases are infections caused by bacteria in the biofilm (dental plaque) that forms on oral surfaces. The basic division in the periodontal diseases is between gingivitis, which affects the gums, and periodontitis, which may involve all of the soft tissue and bone supporting the teeth. Gingivitis and milder forms of periodontitis are common in adults. The percentage of individuals with moderate to severe periodontitis, in which the destruction of supporting tissue may cause the tooth to loosen and fall out, increases with age.

1. Gingivitis

Gingivitis is an inflammation of the gums characterized by a change in color from normal pink to red, with swelling, bleeding, and often sensitivity and tenderness. These changes result from an accumulation of biofilm along the gingival margins and the immune system's inflammatory response to the release of destructive bacterial products. The early changes of gingivitis are reversible with thorough toothbrushing and flossing to reduce plaque. Without adequate oral hygiene, however, these early changes can become more severe, with infiltration of inflammatory cells and establishment of a chronic infection. Biofilm on tooth surfaces opposite the openings of the salivary glands often mineralizes to form calculus or tartar, which is covered by unmineralized biofilm—a combination that may exacerbate local inflammatory responses (Mandel, *J. Am. Dent. Assoc.*, 126:573-80 (1995)). A gingival infection can persist for months or years, yet never progress to periodontitis.

Gingival inflammation does not appear until the biofilm changes from one composed largely of gram-positive streptococci (which can live with or without oxygen) to one containing gram-negative anaerobes (which cannot live in the presence of oxygen). Numerous attempts have been made to pinpoint which microorganisms in the supragingival (above the gum line) plaque are the culprits in gingivitis. Frequently mentioned organisms include *Fusobacterium nucleatum*, *Veillonella parvula*, and species of *Campylobacter* and *Treponema*.

Gingival inflammation may be influenced by steroid hormones, occurring as puberty gingivitis, pregnancy gingivitis, and gingivitis associated with birth control medication or steroid therapy. The presence of steroid hormones in tissues adjacent to biofilm apparently encourages the growth of certain bacteria and triggers an exaggerated response to biofilm accumulation (Caton, "Periodontal diagnosis and diagnostic aids," in Proceedings of the World Workshop in Clinical Periodontics, American Academy of Periodontology, pp. 1-1-22, Princeton, N.J. (1989)). Certain prescription drugs may also lead to gingival overgrowth and inflammation. These include the antiepileptic drug phenyloin (DILANTIN®), cyclosporin, and various calcium channel blockers used in heart disease.

2. Adult Periodontitis

The most common form of adult periodontitis is described as general and moderately progressing. A second form is described as rapidly progressing and severe, and is often resistant to treatment. The moderately progressive adult form is characterized by a gradual loss of attachment of the periodontal ligament to the gingiva and bone, along with loss of the supporting bone. It is most often accompanied by gingivitis (Genco, "Classification of clinical and radiographic features of periodontal diseases," in Contemporary Periodontics, Genco et al., eds., pp. 63-81, (1990)). It is not necessarily preceded by gingivitis, but the gingivitis-related biofilm often seeds the subgingival plaque. The destruction of periodontal ligament and bone results in the formation of a pocket between the tooth and adjacent tissues, which harbors subgingival plaque. The calculus formed in the pocket by inflammatory fluids and minerals in adjacent tissues is especially damaging (Mandel and Gaffar, *J. Clin. Periodontol.*, 13: 249-57 (1986)).

The severity of periodontal disease is determined through a series of measurements, including the extent of gingival inflammation and bleeding, the probing depth of the pocket to the point of resistance, the clinical attachment loss of the periodontal ligament measured from a fixed point on the tooth (usually the cemento-enamel junction), and the loss of adjacent alveolar bone as measured by x-ray (Genco, *J. Periodontol.*, 67(10 Suppl.): 1041-9 (1996)). Severity is determined by the rate of disease progression over time and the response of the tissues to treatment. Adult periodontitis often begins in adolescence but is usually not clinically significant until the mid-30s. Prevalence and severity increase but do not accelerate with age (Beck, *Ann. Periodontol.*, 7(1): 322-57 (1996)).

3. Early-Onset Periodontitis

The forms of periodontitis occurring in adolescents and young adults generally involve defects in neutrophil function (Van Dyke et al., *Infect. Immun.* 27(1): 124-31 (1980)). Localized juvenile periodontitis (LJP) mainly affects the first molar and incisor teeth of teenagers and young adults, with rapid destruction of bone but almost no telltale signs of inflammation and very little supragingival plaque or calculus. *Actinobacillus actinomycetemcomitans* has been isolated at 90 to 100 percent of diseased sites in these patients, but is absent or appears in very low frequency in healthy or minimally diseased sites (Socransky and Haffajee, *J. Periodontol.*, 63(4 Suppl.): 322-31 (1992)). It is possible that the bacteria are transmitted among family members through oral contacts such as kissing or sharing utensils, because the same bacterial strain appears in affected family members. However, evidence of a neutrophil defect argues for a genetic component. Another organism frequently associated with LJP is *Capnocytophaga ochracea*. Neither of these bacteria dominate in the generalized adult form of the disease, where *Porphyromonas gingivalis* is considered of greatest significance (Schenkein and Van Dyke, *Periodontol.*, 6: 7-25 (1994).

Prepubertal periodontitis is rare and may be either general or localized. The generalized form begins with the eruption of the primary teeth and proceeds to involve the permanent teeth. There is severe inflammation, rapid bone loss, tooth mobility, and tooth loss. The localized form of the disease is less aggressive, affecting only some primary teeth. The infection involves many of the organisms associated with periodontitis, but the mix can differ somewhat, with *Actinobacillus actinomycetemcomitans*, *Prevotella intermedia*, *Eikenella corrodens*, and several species of *Capnocytophaga* implicated (Caton, supra). Defects in neutrophil function in both forms of the disease may explain why patients are highly susceptible to other infections as well (Suzuki, *Dent. Clin. North Am.*, 32(2): 195-216 (1988)).

C. Other Diseases Associated with Oral Disorders

Chronic obstructive pulmonary disease, characterized by obstruction of airflow due to chronic bronchitis or emphysema and by recurrent episodes of respiratory infection, has been associated with poor oral health status (Hayes et al., *Ann. Periodontol.* 3(1):257-61 (1998); Scannapieco et al., *Ann. Periondontol.*, 3(1):251-6 (1998)). A positive relationship between periodontal disease and bacterial pneumonia has also been shown (Scannapieco and Mylotte, *J. Periodontol.*, 67(10 Suppl.): 1114-22 (1996)).

Recent studies have also underscored the association of oral infections with certain medically important conditions. Increasing data implicate periodontal disease as a risk factor for cardiovascular diseases such as heart attack and stroke (See e.g., U.S. Pat. No. 6,130,042 to Diehl, et al.; J. Beck, et al., *J. Periodontol.*, 67:1123 (1996)). Epidemiologic studies indicate that, even after accounting for other known risk factors for cardiovascular disease, the relative risk attributable to periodontal infections is significant. Secondly, recent studies have shown that mothers with periodontitis are at greater risk for having low weight babies than those without periodontitis (Offenbacher et al., *J. Periodontol.*, 67:1103 (1996)).

There is also growing acceptance that diabetes is associated with increased occurrence and progression of periodontitis—so much so that periodontitis has been called the "sixth complication of diabetes" (Loe, *Diabetes Care*, 16(1): 329-34 (1993)). The risk is independent of whether the diabetes is type 1 or type 2. Type 1 diabetes is the condition in which the pancreas produces little or no insulin. It usually begins in childhood or adolescence. In type 2 diabetes, secretion and utilization of insulin are impaired; onset is typically after age 30. Together, these two types of diabetes affect an estimated 15.7 million people in the United States and represent the seventh leading cause of death (National Institute of Diabetes and Digestive and Kidney Diseases (NIDDK). Diabetes statistics. NIH Pub. No. 99-3892 (1999)). The goal of diabetic care is to lower blood glucose levels to recommended levels. Some investigators have reported a two-way connection between diabetes and periodontal disease, proposing that not only are diabetic patients more susceptible to periodontal disease, but the presence of periodontal disease affects glycemic control.

D. Oral Disease and Adverse Pregnancy Outcomes

Preterm birth and low birth weight are considered the leading perinatal problems in the United States (Gibbs et al., *Am. J. Obstet. Gynecol.*, 166(5): 1515-28 (1992)). Although infant mortality rates have decreased substantially over the past generation, the incidence of low birth weight (just under 300,000 cases in 1995) has not shown a comparable decline (Institute of Medicine, Committee to Study the Prevention of Low Birth Weight, Division of Health. Promotion and Disease Progression. Preventing low birth weight. Washington: National Academy Press (1985)). Over 60 percent of the mortality of infants without structural or chromosomal congenital defects may be attributed to low birth weight (Shapiro, et al., *Am. J. Obstet. Gynecol.*, 136(3): 363-73 (1980)).

Oral disease may contribute to adverse outcomes of pregnancy as a consequence of a chronic oral inflammatory bacterial infection. For example, toxins or other products generated by periodontal bacteria in the mother can reach the general circulation, cross the placenta, and harm the fetus. In addition, the response of the maternal immune system to the infection elicits the continued release of inflammatory mediators, growth factors, and other potent cytokines, which may directly or indirectly interfere with fetal growth and delivery.

Evidence of increased rates of amniotic fluid infection, chorioamnion infection, and histologic chorioamnionitis supports an association between preterm birth, low birth weight, and general infection during pregnancy. It is noteworthy that the largest proportion of such infections occurred during the pregnancies of the most premature births (Hillier, et al., *N. Engl. J. Med.* 319(15): 972-8 (1988); Hillier, et al., *N. Engl. J. Med.*, 333(26):1737-42 (1995)). The biological mechanisms involve bacteria-induced activation of cell-mediated immunity leading to cytokine production and the synthesis and release of prostaglandins, which may trigger preterm labor (Hillier, et al., supra). Elevated levels of prostaglandin as well as cytokines (interleukin-1 (IL-1), interleukin-6 (IL-6), and tumor necrosis factor alpha (TNF-α) have been found in the amniotic fluid of patients in preterm labor with amniotic fluid infection (Romero, et al., *Am. J. Obstet. Gynecol.*, 186(6 Pt 1):1654-64 (1993)), compared with levels in patients with preterm labor without infection.

E. Mucosal Infections

The mucosal lining of the mouth is subject to a variety of infections and conditions, ranging from benign canker sores to often fatal cancers.

Oral Candidiasis

Chronic hyperplastic candidiasis is a red or white lesion that may be flat or slightly elevated and may adhere to soft or hard tissue surfaces, including dental appliances. It is caused by species of *Candida*, especially *Candida albicans*, the most common fungal pathogen isolated from the oral cavity. Normally, the fungi are present in relatively low numbers in up to 65 percent of healthy children and adults and cause no harm (McCullough, et al., *Int. J. Oral Maxillofac. Surg.*, 25:136-44 (1996)).

The most common form of oral candidiasis is denture stomatitis. It occurs when tissues are traumatized by continued wearing of ill-fitting or inadequately cleaned dental appliances and is described as chronic erythematous candidiasis. Another form, candidal angular cheilosis, occurs in the folds at the angles of the mouth and is closely associated with denture sore mouth (Tyldesley and Field, Oral Medicine, 4th ed., Oxford University Press (1995)). Other common forms of *Candida* infection are *pseudomembranous candidiasis* (thrush), which may affect any of the mucosal surfaces, and acute erythematous candidiasis, a red and markedly painful variant commonly seen in AIDS patients.

In most cases, *Candida* infection may be controlled with antifungal medications used locally or systemically. Control is difficult, however, in patients with immune dysfunction, as in AIDS, or other chronic debilitating diseases. Often the organisms become resistant to standard therapy, and aggressive approaches are necessary (Tyldesley and Field, supra). The spread of oral candidiasis to the esophagus or lungs may be life-threatening and is one of the criteria used to define frank AIDS (Samaranayake and Holmstrup, *J. Oral Pathol. Medi.*, 18:554-64 (1989)).

F. Herpes Simplex Virus Infections

In any given year, about one-half-million Americans will experience their first encounter with the herpes simplex virus type 1 (HSV-1), the cause of cold sores. That first encounter usually occurs in the oral region and can be so mild as to go unnoticed. But in some people, particularly young children and young adults, infection may take the form of primary herpetic stomatitis, with symptoms of malaise, muscle aches, sore throat, and enlarged and tender lymph nodes, prior to the appearance of the familiar cold sore blisters. These blisters usually show up on the lips, but any of the mucosal surfaces may be affected. Bright-red ulcerated areas and marked gingivitis can also be seen (Tyldesley and Field, supra).

Herpes viruses also cause genital infections, which are transmitted sexually. Both HSV-1 and HSV-2 have been found in oral and genital infections, with HSV-1 predominating in oral areas and HSV-2 in genital areas (Wheeler, *J. Am. Acad. Dermatol.*, 18(1 Pt. 2): 163-8 (1988)). Herpes viruses have also been implicated as cofactors in the development of oral cancers. Crowded living conditions may result in greater contact with infected individuals, which aids in transmission of HSV (Whitley, *Pathol. Biol.*, 40(7): 729-34 (1992)).

G. Oral Human Papillomavirus Infections.

There are more than 100 recognized strains of oral human papillomavirus (HPV), a member of the papovavirus family, implicated in a variety of oral lesions (Regezi and Sciubba, Oral pathology. Clinical-pathologic correlations, 2nd ed., (1993)). Most common are papillomas (warts) found on or around the lips and in the mouth. HPV is found in 80 percent of these oral squamous papillomas (de Villiers, *Biomed. Pharmacother.*, 43:31-6 (1989)). The virus has also been identified in 30 to 40 percent of oral squamous cell carcinomas (Chang, et al., *Arch. Dermatol. Res.*, 282(8):493-497 (1990)) and has been implicated in cervical cancer as well. Whether a cancer or nonmalignant wart develops may depend on which virus is present or on which viral genes are activated. Oral warts are most often found in children, probably as a result of chewing warts on the hands. In adults, sexual transmission from the anogenital region may occur (Franchesi, et al., *Cancer Epidemiol. Biomarkers Prev.*, 5:565-575 (1996)). In general, viral warts spontaneously regress after 1 or 2 years. The immune system normally keeps HPV infections under control, as evidenced by the increased prevalence of HPV-associated lesions in HIV-infected patients and others with immunodeficiency.

H. Recurrent Aphthous Ulcers

Recurrent aphthous ulcers (RAU), also referred to as recurrent aphthous stomatitis, is the technical term for canker sores, the most common and generally mild oral mucosal disease. Between five and twenty-five percent of the general population is affected, with higher numbers in selected groups, such as health professional students (Ferguson, et al, *J. Oral Med.*, 39(4):212-217 (1984); Kleinman, et al., *Community Dent. Oral Epidemiol.*, 5:140-144 (1991)).

The disease takes three clinical forms: RAU minor, RAU major, and herpetiform RAU. The minor form accounts for 70 to 87 percent of cases. The sores are small, discrete, shallow ulcers surrounded by a red halo appearing at the front of the mouth or the tongue. The ulcers, which usually last up to two weeks, are painful and can make eating or speaking difficult. About half of RAU patients experience recurrences every one to three months; as many as thirty percent report continuous recurrences (Bagan et al., *J. Oral Pathol. Med*, 20:395-7 (1991)).

RAU major accounts for seven to twenty percent of cases and usually appears as one to ten larger coalescent ulcers at a time, which may persist for weeks or months (Bagan, et al., supra). Herpetiform RAU has been reported as occurring in seven to ten percent of RAU cases. The ulcers appear in crops of ten to one hundred at a time, concentrating in the back of the mouth and lasting for seven to fourteen days (Bagan, et al., supra).

RAU can begin in childhood, but the peak period for onset is the second decade (Lehner, *Proc. R. Soc. Med.*, 61:515-24 (1968)). About fifty percent of close relatives of patients with RAU also have the condition (Ship, *J. Dent. Res.*, 44:837-44 (1965)), and a high correlation of RAU has been noted in identical but not fraternal twins. Associations have been found between RAU and specific genetic markers (Scully and Porter, *J. Oral Pathol. Med.*, 18:21-7 (1989)).

RAU has also been associated with hypersensitivities to some foods, food dyes, and food preservatives (Woo and Sonis, *J. Am. Dent. Assoc.*, 127(8):1202-13 (1996)). Nutritional deficiencies—especially in iron, folic acid, various B vitamins, or combinations thereof—have also been reported, and improvements noted with suitable dietary supplements (Nolan, et al., *J. Oral Pathol. Med.*, 20:389-91 (1991)).

I. Oral and Pharyngeal Cancers and Precancerous Lesions

Oral cancer is the sixth most common cancer in U.S. males and takes a disproportionate toll on minorities; it now ranks as the fourth most common cancer among African American men (Kosary, et al., SEER Cancer Statistics Review, NIH Pub. No. 96-2789 (1995)). The most common oral sites are on the tongue, the lips, and the floor of the mouth.

Viruses that have been implicated in oral cancer include herpes simplex type 1 and human papillomavirus. Epstein-Barr virus, also a herpes virus, is now accepted as an oncogenic virus responsible for Burkitt's lymphoma, occurring primarily in Africa, and nasopharyngeal carcinoma, occurring primarily in China. HPV is a major etiologic agent in cervical cancer, and has been found in association with oral cancer as well (Sugerman and Shillitoe, *Oral Dis.*, 3:130-47 (1997)). HPV DNA sequences have been found in oral precancerous lesions as well as in squamous cell carcinomas (Syrjanen, et al., *J. Oral Pathol.*, 17(6):273-8 (1988)), and experimental evidence has shown that HPV-16 may be an important cofactor in oral carcinogenesis (Park et al., *Oncogene*, 10(11: 2145-53 (1995)). Herpes simplex type 1 antibodies were demonstrated in patients with oral cancer, and herpes was found to induce dysplasia (abnormal cellular changes) in the lips of hamsters when combined with the application of tobacco tar condensate.

More recently, human herpes virus 8, a newly identified member of the herpes virus family, has been found in Kaposi's sarcoma, an otherwise rare cancer occurring in patients with AIDS. These tumors often appear initially within the oral cavity (Epstein and Scully, *Int. J. Oral Maxillofac. Surg.*, 21(4):219-26 (1992)). Other uncommon oral malignant tumors, such as Hodgkin's lymphoma and non-Hodgkin's lymphoma, may also occur in the mouths of AIDS patients. In addition to viruses, infection with strains of the fungus *Candida albicans* has been linked to the development of oral cancers via the fungal production of nitrosamines, which are known carcinogens.

J. Associated Autoimmune Disorders

Oral, dental, or craniofacial signs and symptoms play a critical role in autoimmune disorders such as Sjogren's syndrome, and in a number of chronic and disabling pain conditions. Sjogren's syndrome is one of several autoimmune disorders in which the body's own cells and tissues are mistakenly targeted for destruction by the immune system. Like other autoimmune conditions, Sjogren's syndrome is more prevalent among women. The ratio of females to males affected is 9:1, with symptoms usually developing in middle age. There are an estimated one to two million individuals in the United States with Sjogren's syndrome (Talal, *Rheum. Dis. Clin. North Am.*, 18(3):507-15 (1992)).

The disease occurs in two forms. Primary Sjogren's involves the salivary and lacrimal (tear) glands. In secondary Sjogren's the glandular involvement is accompanied by the development of a connective tissue or collagen disease, most often rheumatoid arthritis, lupus erythematosis, scleroderma, or biliary cirrhosis.

The glandular involvement causes a marked reduction in fluid secretion, resulting in xerostomia and xerophthalmia (dry eyes). The constant oral dryness causes difficulty in speaking, chewing, and swallowing; the dry eyes often itch and feel gritty. There is no cure for Sjogren's, and patients often carry eye drops and water bottles or saliva substitutes in an attempt to provide symptomatic relief. Clinically, the reduction in salivary flow changes the bacterial flora, which, in addition to the reduction in salivary protective components, increases the risk of caries and candidiasis (Daniels and Fox, *Rheum. Dis. Guilt North Am.*, 18:571-589 (1992)). Recent studies have indicated that there is a reduction in masticatory function (Dusek, et al. *Gerodontology* 13(1): 3-6 (1996)) and an increased prevalence of periodontal disease (Najera, et al., *Oral Surg. Oral Med Oral Pathol Oral Radiol. Endod.*, 83(4): 453-7 (1997)). In advanced stages the salivary glands can swell because of obstruction and infection or lymphatic infiltration. In both forms of the disease, other systems can eventually become affected. Nasal, laryngeal, and vaginal dryness can occur, as well as abnormalities in internal organs (Oxholm and Asmussen, *J. Intern. Med.*, 239:467-474 (1996)). Patients with Sjogren's syndrome are at some risk of developing diseases such as non-Hodgkin's lymphoma; clinical data indicate that such lymphomas develop in 5 percent of patients with Sjogren's syndrome (Moutsopoulos et al., *Am. J. Med.*, 64(5):732-741 (1978)).

K. HIV and Osteoporosis

The mouth may serve as an early warning system, diagnostic of systemic infectious disease and predictive of its progression, such as with HIV infection. In the case where oral cells and tissues have counterparts in other parts of the body, oral changes may indicate a common pathological process. During routine oral examinations and perhaps in future screening tests, radiographic or magnetic resonance imaging of oral bone may be diagnostic of early osteoporotic changes in the skeleton.

L. HIV Infection

The progressive destruction of the body's immune system by HIV leads to a number of oral lesions, such as oral candidiasis and oral hairy leukoplakia, that have been used not only in diagnosis but also in determining specific stages of HIV infection. Oral candidiasis is rarely seen in previously healthy young adults who have not received prior medical therapy such as cancer chemotherapy or treatment with other immunosuppressive drugs. Oral candidiasis may be the first sign of HIV infection and often occurs as part of the initial phase of infection—the acute HIV syndrome (Tindall, et al., "Primary HIV infection: Clinical, Immunologic, and Serologic Aspects," in The Medical Management of AIDS, Sande, et al., eds., pp. 105-129; W.B. Saunders, 1995). It tends to increase in prevalence with progression of HIV infection when CD4 lymphocyte counts fall. It also appears to be the most common oral manifestation in pediatric HIV infection (Kline, *Pediatrics,* 97(3):380-388 (1996) and has been demonstrated to proceed to esophageal candidiasis, a sign of overt AIDS. (Saah at al., Am. J. Epidemiol., 135:1147-1155 (1992)). Both the pseudomembranous and the erythematous forms of candidiasis appear to be important predictors of progression of HIV infection (Klein et al., AIDS, 6(3): 332-333 (1992)).

Like oral candidiasis, oral hairy leukoplakia in HIV-positive persons heralds more rapid progression to AIDS. Oral hairy leukoplakia is an oral lesion first reported in the early days of the AIDS epidemic. Since its discovery, hairy leukoplakia has been found in HIV-negative persons with other forms of immunosuppression, such as organ or bone marrow recipients and those on long-term steroid therapy, and less frequently among immunocompetent persons.

Linear gingival erythema and necrotizing ulcerative periodontitis may be predictive of progression of HIV infection. (Mealey, *Ann. Periodontaol.,* 1:256-321 (1996)). Necrotizing ulcerative periodontitis, a more serious periodontal condition observed in HIV-infected persons, is a good predictor of CD4+ cell counts of under 200 per cubic millimeter. In addition, the numerous ulcerative and nonulcerative conditions that affect the oral cavity may affect the biologic activity of HIV and are affected by its treatments (Mealey, supra).

M. Osteoporosis and Oral Bone Loss

Osteoporosis, a degenerative disease characterized by the loss of bone mineral and associated structural changes, has long been suspected as a risk factor for oral bone loss. In addition, measures of oral bone loss have been proposed as potential screening tests for osteoporosis. Osteoporosis affects over 20 million people in the United States, most of whom are women, and results in nearly 2 million fractures per year (National Institute of Arthritis, Musculoskeletal and Skin Diseases 2000). The disease is more prevalent in white and Asian American women than in black women. Oral bone loss has been reported to be more prevalent in women than in men. Also, the association between estrogen status, alveolar bone density, and history of periodontitis in postmenopausal women has been studied (Payne et al., *J. Periodontol.,* 6:24-31 (1997)).

Larger cross-sectional studies, as well as longitudinal and mechanism studies, are needed to better define the relationship between osteoporosis, osteopenia, and oral bone loss, periodontal disease, and tooth loss. The role of factors involved in the regulation of bone mineral density in men as well as in postmenopausal women needs to be evaluated further with reference to oral bone loss, tooth loss, and periodontal disease. Variables such as sex, race, dietary calcium and phosphorus, vitamin D intake, exercise, body mass index, smoking, genetics, medication use, reproductive history, and psychosocial factors need to be assessed in depth. In addition, reliable and valid criteria and imaging technologies for assessing osteoporosis and oral bone loss are needed to better elucidate the full relationship between skeletal and mandibular bone mineral density, periodontal disease, alveolar ridge resorption, and tooth loss.

II. Salivary Mucins

The functional properties of saliva proteins, known as salivary mucins, relative to oral health status are the subject of continuing research (Ayad, et al., *J. Dent. Res.,* 79:976-982 (2000)). The existence of high-molecular-weight glycoproteins in saliva and saliva secretions, called mucins, has been recognized for nearly thirty years (Offner, et al., *Adv. Dent. Res.,* 14:69-75 (2000)). Mucins are essential for oral health and perform many diverse functions in the oral cavity. For example, mucins are the principal protein components of the mucous layer which coats epithelial surfaces in the gastrointestinal, respiratory, and reproductive tracts. This layer forms a viscous barrier which protects the underlying epithelium from desiccation, mechanical injury, and microbial assault, while allowing for active absorption and secretion by mucosal cells. Mucins are also secreted by salivary glands and are thought to have a major role in the protection of oral epithelial surfaces, as well as in the non-immune host defense system in the oral cavity (Offner, et al., supra).

From a biochemical standpoint, mucins are comprised of approximately 15%-20% protein, and up to 80% carbohydrate, present largely in the form of O-linked glycans (Strous and Dekker, *Crit. Rev. Biochem. Mol. Biol.,* 27:57-92 (1992); Gendler and Spicer, *Ann. Rev. Physiol.,* 57:607-634 (1995)). Serine and threonine are the most abundant amino acids and serve as the attachment sites for these carbohydrate chains. Many mucins have monomeric molecular weights greater than two million Daltons, and form multimers more than ten times that size (Offner et al., supra). To date, eleven distinct human mucin genes have been isolated and have been numbered MUC1-MUC4, MUC5AC, MUC5B, MUC6-8, and MUC11-MUC12, in the order of their discovery.

These mucins share several common properties. The polypeptide backbone can be divided into three regions. The central region is enriched in serine, threonine, and sometimes proline, and contains tandemly repeated sequences ranging in length from 8 to 169 amino acids. This domain serves as the attachment site for the O-glycans, and each mucin has a unique, signature tandem-repeat sequence. The N- and C-terminal regions of mucins are non- or sparsely glycosylated with both O- and N-linked sugars. In many mucins, these flanking regions are cysteine-rich, containing nearly 10% cysteine. Mucins could be organized into three distinct classes: the large gel-forming mucins (i.e., MUC2, MUC5AC, MUC5B, and Iv UC6); the large membrane-associated mucins (i.e., MUC1, MUC3, MUC4, and MUC12); and the small soluble mucins represented by MUC7. Insufficient information is available to assign MUC8 and MUC11 to one of these categories (Ofnner, et al., supra).

The MUC7 gene has previously been reported (Bobek, et al., *Genomics*, 31:277-282 (1998)). The MUC7 mucin is generally regarded as having the ability to bind to and aggregate several species of oral bacteria, including several strains of *S. mutans*, and *A. actinomycetemcomitans*. The former is thought to be the most cariogenic of the oral bacteria and the latter is one of two major pathogens in periodontal disease. The MUC7 mucin also binds *C. albicans* and can have candidicidal activity. Desialylation of the mucin apparently destroys its ability to aggregate some species of oral bacteria. Recent studies further indicate that MUC7 mucin binds oral neutrophils on a different oligosaccharide motif than is used to bind oral bacteria. With regard to the primary site of binding to oral bacteria, recent studies suggest that a non-glycosylated domain of MUC7 mucin can be more responsible than its oliogosaccharides.

Bolscher et al., (*J. Dent. Res.*, 78:1362-1369 (1999)) have developed an ELISA for MUC7 that quantitated mucin in stimulated separate salivas from the parotid, submandibular, and sublingual glands of six subjects. The Bolscher study reported the mean concentration of MUC7 for each of the three glandular salivas. Rayment et al. (*J. Dent. Res.*, (2000) 79:1765-1772) have developed a capture ELISA for MUC7 and measured the mean concentration in the stimulated whole saliva of 61 subjects.

In addition, others have either studied the functional properties of MUC7 or the concentrations of other saliva proteins relative to oral health status. Prakobphol, et al. have studied the different types of oligosaccharide chains on MUC7 (*Biochemistry* 38:6817-6825 (1999)). Prakobphol, et al. reported that different individuals have different classes of oligosaccharides on their MUC7, but they did not include a population study, nor did they quantitate the mucin or its oligosaccharides. Bobek, et al. first cloned the MUC7 gene and is now studying its functional properties (*Genomics* 31:277-282 (1998)). Ayad, et al., have systematically tested the relationship of various components in saliva to oral health status (*J. Dent. Res.* 79:976-982 (2000)).

U.S. Patent Publication No. 2003/0040009 A1 to Denny et al., which is incorporated herein by reference, describes the relationship of mucin concentration to DFT (decayed and filled permanent teeth). The mucin test, as described in U.S. Patent Publication No. 2003/0040009 A1, comprises first separating a salivary mucin, e.g., MUC7 mucin, from all other sialic acid-containing molecules in the saliva, by known methods such as sodium dodecylsulfate-polyacrylamide gel electrophoresis (SDS-PAGE). The sialic acid attached to the mucin is then quantitated and reported.

There have been many attempts to measure other factors in saliva and then relate such factors to the caries experience of the individual donors. However, the vast majority of studies, which have reported values for pH, various ions, macromolecules, and flow rate, have found little evidence of a correlation. A few studies have shown a small amount of correlation, though without consensus between studies. Thus it would be of value to develop a test that exhibits a strong correlation between a specific factor and the risk level for caries development, and would allow for the prediction or forecasting of existing caries levels. In addition, this test should be simple and accurate.

Despite advances, caries remains a disease experienced by 85% of U.S. school children before the age of 17. Though wide spread, approximately 75% of all caries is concentrated in only 25% of the population (U.S. Dept. of Health & Human Services. National Institutes of Health Consensus Development Conference Statement. *Diagnosis and Management of Dental Caries Throughout Life* (2001)). At present, these caries-prone individuals are identified by accumulated caries experience, usually in an office setting. However, this professional judgment is based on personal anecdotal experience. Literature on the prediction of future caries development in specific individual subjects is lacking. The current level of scientific effort is reflected in 24 studies of the efficacy of caries preventives and non-invasive treatments, whose subject populations were selected on the basis of "high-risk" or "caries-active." These studies are summarized in "Evidence Report/Technology Assessment, Number 36: Diagnosis and Management of Dental Caries" (U.S. Dept. of Health & Human Services. National Institutes of Health Consensus Development Conference Statement. *Diagnosis and Management of Dental Caries Throughout Life* (2001)). With average ages ranging from 1 to 13 years, these studies averaged 175 individuals per study. Each study was evaluated on the quality of the evidence for judging the efficacy of a particular treatment. The four grades achievable were "good," "fair," "poor," and "incomplete." Only four of the individual studies received a fair rating for their results and conclusions. The remaining 20 were rated as incomplete. While a number of factors were at play in this rating, special note was made of the lack of consistency in the inclusion criteria for "at-risk" and "caries-active" participants.

In general, these studies have used either *Streptococcus mutans* titers or past caries history, such as dmft or dmfs (deciduous teeth), and DMFT or DMFS (permanent teeth), to select the high risk and/or caries-active subjects. A problem associated with these inclusion criteria is the subjectiveness associated with the actual diagnoses, as well as lack of agreement on what number constitutes a caries-prone individual. This uncertainty about identification of individuals who have a high potential for future caries development is exemplified in a divided study that was partitioned into "high-risk" (*S. mutans* titer-based), and "caries-active" (DMFS-based) subjects. The same treatment agent gave a 33% reduction in new caries in the "high-risk" group and a 9% increase in the "caries-active" group (U.S. Dept. of Health & Human Services. National Institutes of Health Consensus Development Conference Statement. Diagnosis and Management of Dental Caries Throughout Life (2001)). In addition to the confusion about what inclusion criteria best identify those with the highest projected rates of cariogenesis, the assessment report notes that neither approach to caries risk assessment has ever been validated.

Thus, there is value and need for a test that provides standard subject-identification criteria and that leads to a consistent diagnosis throughout childhood and early adulthood. A preferred test would have a uniform design such that it would accommodate all age groups and races.

SUMMARY OF THE INVENTION

This present invention provides methods and test devices for predicting, assessing, and diagnosing the risk of a disease using salivary analysis. It is not intended that the present invention be limited to compositions and methods for predicting and preventing specific diseases. Thus, the present invention provides methods for predicting and reducing the risk of a disease and diagnostic kits for detecting a disease based on measurement of the content of lectin-binding components in a whole (i.e., unfractionated) saliva sample.

More specifically, one aspect of the present invention provides a method for predicting the risk of a disease in a subject, comprising providing an unfractionated saliva sample from a subject; contacting an aliquot of the saliva with one or more lectins under conditions that allow the one or more lectins to bind to lectin-binding components of the saliva; detecting the amount of bound lectin; and comparing the amount of bound lectin to the amount known to bind a saliva sample from a control patient (i.e., a patient or patients without the disease), wherein the amount detected is indicative of the risk of the disease. The saliva sample may be a stimulated saliva sample or, in a preferred embodiment, an unstimulated saliva sample. The lectin-binding components may be any of the salivary oligosaccharides that bind lectins. In one embodiment, the lectin is MAL I. In another embodiment, the lectin is selected from a lectin other than PNA.

In one embodiment, the contacting and detecting steps are part of a Western blot procedure. For example, in one embodiment, the contacting comprises applying a drop of said saliva sample to a matrix material, and then contacting the matrix material with a solution of said one or more lectins. In another embodiment, the contacting comprises applying one or more lectins to said matrix material; and then contacting the matrix-bound lectins with the saliva sample.

A further aspect of this invention provides a method of using one or more lectins for predicting the risk of a disease, comprising providing an unfractionated saliva sample from a subject; providing one or more lectins that bind to one or more oligosaccharide components of the saliva; contacting the saliva sample with the one or more lectins under conditions that allow the one or more oligosaccharide components to bind to the one or more lectins; and detecting the amount of bound lectins, wherein the amount of bound lectins correlates with the risk of the disease. In one embodiment, the contacting and detecting steps are part of a Western blot procedure.

In one embodiment, the methods of the present invention can further comprise the step of assessing the risk of the disease at a defined level, such as high, medium, low, very low or zero. In addition, the methods of the present invention can further comprise the step of assessing the risk of future development of a disease in a subject.

Another aspect of this invention provides a method for preventing or reducing the risk of a disease, comprising providing an unfractionated saliva sample from a subject; contacting an aliquot of the saliva with one or more lectins under conditions that allow the one or more lectins to bind to a lectin-binding component of the saliva; detecting the amount of bound lectin; comparing the amount of bound lectin to the amount known to bind a saliva sample from a control subject, wherein the amount is proportional to the risk of a disease in said subject; and administering a therapeutic reagent to the subject when the content of the component in the saliva is above or below the level expressed in normal control (i.e., a subject free from the disease being tested for). The oral fluid standard can comprise a sample from a control (i.e., a subject who does not suffer from the disease being tested for).

Another aspect of this invention provides a diagnostic kit for detecting a disease, comprising: a) a means for collecting a saliva sample; b) a means for measuring the amount of a lectin-binding component in the sample; and c) an oral fluid standard for comparing the amount of the component in the sample. In one embodiment of the present invention, the kit is a Western blot format. In kits of this nature, a drop of a saliva sample is transferred onto a matrix material (e.g., a nitrocellulose filter). The drop is then probed with one or more lectins, and the lectins are detected by means of suitable methods.

It is not intended that the methods and devices of the present invention be limited to predicting diseases of human subjects within a particular age group or race. Preferably, the methods and devices of this invention are universal in that the accommodate subjects of all ages and races.

The diseases that can be predicted according to the methods of this invention include, but are not limited to, oral diseases and associated medical disorders. Oral diseases and associated medical disorders include, but are not limited to, dental caries; periodontal diseases (e.g., gingivitis, adult periodontitis, early-onset periodontitis, etc.); diseases associated with periodontal disorders (e.g., pulmonary and respiratory diseases, and cardiovascular diseases such as heart attack, stroke, atherosclerosis, etc.); diabetes; perinatal disorders (e.g., low birth weight and premature births); mucosal infections; oral and pharyngeal cancers; precancerous lesions; associated autoimmune disorders (e.g., Sjorgren's syndrome); HIV; and osteoporosis.

In preferred embodiments, the present invention provides a method for predicting dental caries risk. The dental caries can be early-onset dental caries, adult dental caries, root caries, DFT, DMF, DFS or DMFS in children and adults. In children dental caries can also include dft, dmf, dfs, dfs/t or dmfs.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Figure 1:
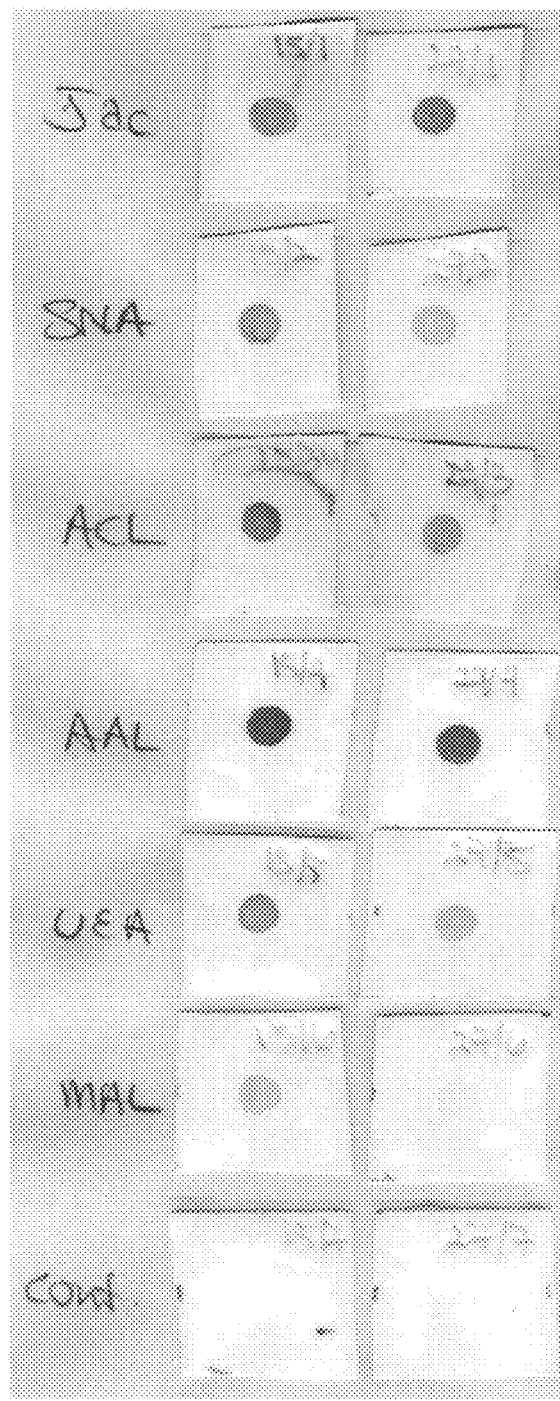
FIG. 1 is an image of a dot blot test of saliva samples from two individuals according to this invention using a lectin panel comprising Jacalin, SNA, ACL, AAL, UEA, and MAL I.

The inventors have identified and evaluated factors in saliva, i.e., lectin-binding components of saliva, which may or may not be associated with mucins, that facilitate caries prediction, and have utilized this discovery to develop a caries risk test that is suitable for commercialization. These lectin-binding components are better and more broadly applicable risk indicators than MUC7 and MUC5B mucins alone. Furthermore, it was discovered that for individuals whose mucin lacks a lectin-binding oligosaccharide(s) or who lack mucin, the lectin-binding oligosaccharides are present in quantity on other salivary glycoproteins. Accordingly, the salivary analyses of this invention provide a more universal method for predicting and reducing the risk of disease. Thus, with the risk tests of this invention, groups of children and young adults for whom the mucins may not be forecasters of accumulated caries experience can still be identified with high probability, even when grouped together with individuals for whom the mucins are indicators. The lectin-binding components can be quantitated with less difficulty than the mucins alone and therefore provide simple, reliable tests.

More specifically, one aspect of this invention provides a method for predicting the risk of a disease in a subject, comprising providing an unfractionated saliva sample from said subject; contacting an aliquot of said saliva with one or more lectins under conditions that allow said one or more lectins to bind to a component of said saliva; detecting the amount of bound lectin; and comparing the amount of bound lectin to the amount known to bind a saliva sample from a control patient or subject. In one embodiment, the disease is dental caries.

A "control" patient or subject as defined herein is a representative patient or subject of known disease level defined, e.g., according to the number of cavities. For example, in certain populations, 0-2 DFS (total Decayed and Filled tooth Surfaces in the permanent teeth) may be associated with very low risk of developing caries in young adults, while 3-8 DFS may be associated with low risk, 9-16 DFS with medium risk, and 17 or more DFS with high risk (see Example 4). When multiple lectins are employed in a method of this invention, they may be used either individually or in groups. The amount of bound lectin may be determined (e.g., through direct visual observation with naked eyes) by comparing it with one or more (i.e., a panel of) control amounts. Each control amount is the amount of bound lectin known to bind a saliva sample from a control patient or subject. The risk of a disease is then determined based on the amount of bound lectin. For example, if the amount of bound lectin is comparable to that for the above-defined "very low risk group," the individual is predicted to be at risk of developing 0-2 DFS.

An "adult" is defined according to National Institute of Health standards as a human that is at least 21 years old.

A "child" is defined according to National Institute of Health as a human that is less than 21 years old.

In one embodiment, the lectin-based caries risk tests of this invention, also referred to as "caries tests," measure two outcomes: 1) caries assessment and 2) risk evaluation. Caries assessment is described as the accumulated caries history of an individual. Examples of metrics are DFS, (total Decayed and Filled tooth Surfaces in the permanent teeth, dfs, (total decayed and filled surfaces in deciduous ("baby") teeth), and dfs/t, which refers to the number of decayed and filled surfaces per remaining deciduous teeth. Risk evaluation provides a projection of the number of caries an individual can expect to accumulate by a certain age in the absence of individualized preventive treatments. An example of a metric that is used according to this invention is the risk level scale of high, medium, low, and very low. As will be seen these risk levels can be linked directly to acquired ranges of DFT and dfs/t in the test populations. Risk may also be calibrated to more or less than four levels and can also be calibrated to different ranges of DFT or dft to better reflect the caries history patterns of different populations to which the caries test may be applied.

The risk tests of this invention can be integrated into dental practice as a common diagnostic procedure health screening, and in broader oral health campaigns to improve identification, treatment, and prevention in high-risk individuals. The diagnostic screening information provided by these combinations of test and technology will aid the health care provider in identifying caries-prone children, teen-agers, and young adults. This will be most helpful at stages of dental development when physical examination alone or dmfs (decayed, missing, and filled surfaces) in deciduous teeth and DMFS in permanent teeth cannot identify with statistical certainty, those individuals who are at-risk.

I. Definitions

To facilitate understanding of the invention, a number of terms are defined below.

As used herein, the term "saliva" refers to an oral fluid, regardless of where the saliva is secreted in the oral cavity, or how it is collected. The saliva can be unstimulated or stimulated. In a preferred embodiment, the sample of saliva is unstimulated. As used herein, the term "unstimulated saliva" means that the subject will expectorate in a collection vessel without stimulation of salivary flow. For example, a subject's saliva may not be stimulated by chewing on a piece of paraffin film or tart candy. An "unfractionated" saliva sample means that none of the components of the saliva sample have been separated out of the sample that is to be used in a method or test of this invention.

As used herein, the terms "prediction of dental caries risk" or "prediction of dental caries experience" refer to the risk of future dental caries development and the forecast of the current accumulated number of caries and fillings, respectively.

Caries is a disease characterized by demineralization of the dental enamel and of the dentin in various stages of progress, until it affects the pulp space. Fillings refer to those caries that have been treated or restored. "Prediction" is synonymous with the terms prognostication, forecasting, foretelling, foreseeing, portending, etc.

As used herein, the term "oral fluid standard" refers to a solution useful as a surrogate for naturally occurring oral fluid in the testing, calibration and standardization of oral fluid collection methods and devices, oral fluid handling, preservation and storage methods and devices, and oral fluid-based assay methods and devices. Oral fluid standards are not intended as an in vivo therapeutic replacement or supplement for saliva, but rather are used as ex vivo testing standards. The term oral fluid standard may refer to the oral fluid surrogate composition alone, or to the oral fluid surrogate spiked with one or more additional components such as an analyte and/or human serum. The particular meaning of the term oral fluid standard will be apparent from the context in which it is used.

As used herein, the term "oral fluid" refers to one or more fluids found in the oral cavity individually or in combination. Oral fluids include, but are not limited to, saliva and mucosal transudate. It is recognized that oral fluids (e.g., saliva) are a combination of secretions from a number of sources (e.g., parotid, submandibular, sublingual, accessory glands, gingival mucosa and buccal mucosa), and the term oral fluid includes the secretion of each of these sources individually or in combination.

As used herein, the term "mucins" refers to acid mucopolysaccharides complexed with proteins. The acid mucopolysaccharides are a group of related heteropolysaccharides usually containing two types of alternating monosaccharide units, of which at least one has an acidic group (typically either a carboxyl or a sulfuric group). The term "MUC7" refers to a particular mucin gene. The term "MUC7 mucin or occasionally MUC7 protein" refers to the protein encoded by the MUC7 gene and post-translationally modified to contain the necessary carbohydrates and possibly sulfur to qualify it as a mucin, which is a recognized biochemical class of glycoproteins. As used herein, the term "lectins" refers to proteins that bind, often with great specificity, to defined oligosaccharide structures on glycoproteins and glycolipids.

As used herein, the term "subject" refers to a subject whose saliva is being tested for a particular disease. The subject can be a human or an animal.

As used herein, the terms "normal subject" or "normal control" refer to a subject who does not suffer from the particular disease being tested for (e.g., dental caries or any diseases associated with dental caries experience).

As used herein, the terms "oral disorders" and "oral diseases" refer to diseases and disorders affecting the oral cavity, and associated medical disorders. Oral disorders include, but are not limited to, dental caries; periodontal diseases (e.g., gingivitis, adult periodontitis, early-onset periodontitis, etc.); mucosal infections (e.g., oral candidiasis, herpes simplex virus infections, oral human papillomavirus infections, recurrent aphtous ulcers, etc.); oral and pharyngeal cancers; and precancerous lesions.

As used herein, the term "associated medical disorders" refers to medical conditions associated with periodontal diseases (e.g., pulmonary and respiratory diseases, and cardiovascular diseases such as heart attack, stroke, atherosclerosis, etc.); associated autoimmune disorders (e.g., Sjorgren's syndrome); HIV; and osteoporosis.

A Western blot involves transfer of an aliquot (e.g., a drop) of a saliva sample to a membrane (e.g., nitrocellulose, nylon, or PVDF). Presence of a lectin-binding component in the saliva is then detected by contacting the membrane with a solution containing one or more lectins, which are in turn detected by suitable means. Detection may be by autoradiography, colorimetric reaction or chemiluminescence. For example, the lectins can be conjugated to biotin, which in turn can be detected and quantitated by contacting the bound lectin conjugates with fluorescently labeled avidin, or can be directly conjugated to any reporter, including but not limited to microparticles such as microlatex beads.

The present invention provides compositions and methods for assessing the risk of a disease using salivary analysis. In particular, the compositions and methods of the present invention can be used to predict and prevent the risk of oral diseases and other associated diseases.

II. Salivary Analysis For Predicting Diseases

The present invention provides new saliva-based methodologies and technologies for predicting the risk of and treating a disease. Specifically, the present invention relates to compositions and methods for predicting the risk of a disease based on analysis of salivary lectin-binding components. According to the invention, lectin-binding components of saliva, which may or may not be associated with mucins, can be probed with one or more lectins, and the lectin-binding activity of the saliva can be compared to the amount of lectin-binding activity of the saliva of a control subject, wherein the amount of bound lectin is indicative of the risk of the disease.

The lectin-binding components in saliva were discovered to be better and more broadly applicable risk indicators than MUC7 and MUC5B mucins alone. Furthermore, the present invention demonstrates that for individuals in whom the mucin test does not apply, either their mucin lacks the specific lectin-binding oligosaccharide(s), or that lacking mucin, the oligosaccharide(s) are present in quantity on another salivary glycoprotein. Thus, according to one embodiment of the invention, the risk of oral diseases and associated diseases is predicted by quantitating the total lectin binding from unstimulated or stimulated saliva.

A. Lectins

Lectins are a family of proteins derived from a variety of plants, animals, and microbes. As a family they can be characterized by their ability to bind selectively to specific sugars or sugar linkages present in the oligosaccharide chains of carbohydrate-bearing molecules. One of the most common uses of lectins is to ascertain individual blood types, of which there are at least 26 different families recognized at this time. The A, B, O blood types represent only one of these families, which have as their common thread the types of sugar and linkages that are represented in the carbohydrate-bearing molecules of an individual. As is commonly known, expression of blood types is genetically based. Some of the lectins used in the caries tests of this invention interact with common blood types. All of the lectins that are used in the caries tests of this invention are commercially available.

The role of lectins in the caries tests of this invention is to quantitate a variety of types of sugars and their intermolecular linkages associated with glycoproteins, glycolipids, complex polysaccharides, and other carbohydrate-containing molecules present in saliva. The tests according to this invention are based on the integration/combination of the quantitative results from a variety of lectins, some of which appear to be measuring carbohydrate properties that are positively correlated with caries history and others that are negatively associated with caries history. Individual outcomes of the caries test represent the relative balance between positively and negatively correlated lectin affinities in the saliva. The test may be run using a mixture of lectins or run with individual lectins whose quantitative results can then be mixed statistically.

In a preferred embodiment, the lectins used in the methods of this invention are one or more lectins selected from the group consisting of DSL, ECL, PSA, WGA, UEA; MAL I, MAA, PNA, AAL, LTL, MAL II, JAC, LEL, SNA, PTL I, ACL, GSL II, VVA, BPL, WFL, SJA, MPL, GNL, HHL, CCA, NPL, STL, PHA-L, PHA-E, GSL I, DBA, HMA, EEA, LPA, and PTL II. In another embodiment, the lectins are selected from the group consisting of AAL, LTL and UEA 1. In yet another embodiment, the lectin is selected from any lectin other than PNA.

In one nonlimiting example, a panel of lectins comprising DSL, ECL, PSA, MAL I, PNA, AAL, LTL, MAL II, JAC, LEL, PTL I, GSL II, VVA, BPL, SJA, MPL, and CCA can be used in a method of this invention to predict the risk for an adult for developing dental caries in permanent teeth.

In another nonlimiting example, a panel of lectins comprising ACL, PNA, LTL, PSA, MAL II, MAA, STL, PTL I, LEL, DSL, ECL, AAL, VVA, GNL I, CCA, SNA, JAC, WFL, SJA, MAL I, and BPL can be used in a method of this invention to predict the risk in a child for developing caries in deciduous teeth.

B. Sampling Methods

In a preferred embodiment, the methods of the present invention analyze an unstimulated or stimulated saliva sample to test for the risk of a disease. Saliva specimens for testing can be collected following various methods known in the art. Proper conditions for generating unstimulated saliva have been described (Nazaresh and Christiansen, *J. Dent. Res.*, 61:1158-1162 (1982)). Methods and devices for collecting saliva have also been described (U.S. Pat. No. 5,910,122 to D'Angelo; U.S. Pat. No. 5,714,341 to Thieme et al.; U.S. Pat. Nos. 5,335,673 and 5,103,836 to Goldstein et al.; U.S. Pat. No. 5,268,148 to Seymour; and U.S. Pat. No. 4,768,238 to Kleinberg et al., each of which is incorporated herein in its entirety by reference). It is contemplated that the methods of the present invention can also be practiced by analyzing stimulated saliva.

One preferred method of saliva collection utilizes a self-contained sterile device that is inserted into the mouth to collect a volume of unstimulated saliva, which is then combined with an aliquot of included sterile buffer. In an alternative embodiment, the sample is collected by having the subject lick or spit on a test strip of this invention.

Furthermore, the methods of the present invention are not limited to performing salivary analysis immediately after collection of the sample. In other embodiments, salivary analysis following the methods of the present invention can be performed on a stored saliva sample. The saliva sample for testing can be preserved using methods and apparatuses known in the art (See, e.g., U.S. Pat. No. 5,968,746 to Schneider, incorporated herein its entirety by reference).

It is also contemplated that the methods of the present invention be used to perform salivary analysis on saliva samples that have been treated to reduce its viscosity. Mucopolysaccharide-containing body fluids, such as saliva, contain antibodies and other metabolites that are useful in the diagnosis of diseases, including those of bacterial, viral, and metabolic origin. However, the viscous nature of such fluids, due to the nature of mucopolysaccharides, makes testing of these fluids difficult. In order to prepare saliva for any laboratory testing procedure, the saliva must be rendered sufficiently fluid (i.e., viscosity must be reduced) and free from debris. Techniques used to remove debris include centrifugation and filtration. The viscosity of saliva can also be reduced by mixing a saliva sample with a cationic quaternary ammonium reagent (See, U.S. Pat. No. 5,112,758 to Penman et al., incorporated herein in its entirety by reference).

Further, it is contemplated that the methods of the present invention be used in analyzing factors from saliva samples obtained from a subject suffering from xerostomia. Xerostomia is a condition in which the salivary glands do not produce sufficient quantities of saliva. The onset of the effects of xerostomia is insidious, with no clear line of demarcation when one suffers from the malady. It is estimated that several million individuals suffer from this condition nationwide. The actual number of individuals suffering from xerostomia is not known, however, because there has been little acknowledgement of the prevalence or severity of the problem until recently. It is estimated that about ten percent of the population over 50 years of age and 25 percent of the population over 65 years of age suffer from xerostomia. The majority of those affected are women.

Some direct primary causes of xerostomia are autoimmune diseases, such as Sjogren's syndrome, medical irradiation, malnutrition, hormonal imbalance, arthritis and aging. When areas of the head or neck are medically irradiated by as little as 1000 rads per week, 85 percent of the patients suffer from xerostomia after six weeks and 95 percent after three months. Radiation xerostomia onsets rapidly, with a greater than 50 percent decrease in salivary flow after one week, and a greater than 75 percent decline after six weeks of treatment. The xerostomia is progressive, persistent, and irreversible, reaching a greater than 95% reduction in saliva output three years after radiation. In patients where only part of the major salivary glands is in the path of the ionizing radiation, the non-exposed portion can undergo hyperplasia and partly compensate for the damaged acini. The most severe cases of xerostomia are caused by radiation therapy after head and neck surgery, and by autoimmune diseases such as lupus, Sjogrens Syndrome, and rheumatoid arthritis (See, e.g., P. C. Fox, et al., *J. Am. Dental Assoc.*, 110:519-525 (1985)). Secondarily, xerostomia is a side effect from the administration of over 400 drugs, including major antihypertensives, antidepressants, antispasmodics, diuretics, muscle relaxants, antipsychotics, appetite depressants, and therapeutics for Parkinson's disease.

To predict the risk of a disease in a subject suffering from xerostomia, it is contemplated that various methods for enhancing saliva be used to obtain a salivary sample for analysis. Various methods for enhancing saliva are known in the art. For example, U.S. Pat. No. 5,886,054 (incorporated herein in its entirety by reference) teaches a therapeutic method for enhancing saliva, using an aqueous solution of at least one polymer and one electrolyte. The aqueous solution is preferably buffered and optionally contains at least one mucin. In another example, U.S. Pat. No. 6,230,052 (incorporated herein in its entirety by reference) teaches an implantable device for inducing salivation by neural stimulation at neurally sensitive location within an oral or perioral tissue of a user.

It is understood that the examples for sampling saliva described above are for illustrative purposes only. It is also understood that various modifications for sampling saliva are contemplated to be within the scope of the present invention.

C. Statistical Tests

In one embodiment, the methods of this invention for predicting the risk of a disease in a subject can further comprise the step of assessing the risk of the disease as high, medium, low, very low, or zero. In another embodiment, the methods of this invention for predicting the risk of a disease in a subject can further comprises assessing the risk of future development of the disease in the subject. For example, the method of assessing future risk can comprise comparing the amount of lectin binding to a regression analysis derived from a group of subjects expressing a range of disease severity.

The statistical tests involved in the discovery of the predictive nature of lectin-binding components of saliva are standard and well-known in the art of statistical analyses. Specifically, the present invention used Pearson's correlation coefficient, simple linear regression analysis, multiple linear regression analysis, and ANOVA. An aspect of the reliability for the prediction of dental caries risk is the accuracy of representation involving the relationship between the test results and the observed decay or fillings on teeth (DFT) in the standard population. In most statistical programs, this relationship is calculated by the least squares method, and yields the mathematical formula from which the linear regression line is derived and predictions can be made. However, the typical regression line takes into account only the variation of the dependent variable. In a particular embodiment, the variation of dental caries experience is a dependent variable.

In an embodiment of the invention where there is a normal variation in DFT and lectin-binding component concentration, a different type of statistical test can be used to give the most representative mathematical regression equation. This approach to regression analysis can be performed by a variety of statistical tests, such as orthogonal least squares, geometric mean regression, Bartlett's, three-group method (i.e., for Type II regression analysis), and random variable regression analysis. These alternative methods can also be used to calculate the mathematical description of the regression line on the data. In this embodiment, these methods did not measurably alter the predictive outcomes obtained by traditional simple linear regression analysis.

The $R^2$ of the regression analysis is preferably at least 0.3 (i.e., any number between and including 0.3 and 1). For example, for a 3-level test, the $R^2$ may be at least 0.9; for a 4-level test, the $R^2$ may be at least 0.98; for a 5-level test, the $R^2$ may be at least 0.99.

D. Test Versions

In general, this invention provides a method for predicting the risk of a disease in a subject, comprising providing an unfractionated saliva sample from the subject; contacting an aliquot of the saliva with one or more lectins under conditions that allow the lectin(s) to bind to a lectin-binding component of the saliva; detecting the amount of bound lectin; and comparing the amount of bound lectin to the amount known to bind a saliva sample from a control subject, wherein the amount of bound lectin is indicative of the risk of the disease.

In one embodiment, the contacting and detecting steps are part of a Western blot procedure. In one example, the procedure comprises applying a drop of said saliva to a matrix material; and contacting the matrix with a solution containing one or more lectins. In order to visualize the amount of binding, the lectins can be coupled to a reporter or to a colored microparticle, as discussed below in detail.

Alternatively, the Western blot procedure comprises applying one or more lectins to a matrix material; and contacting the matrix-bound lectins with the saliva sample.

The present invention also provides tests based on the methods of this invention for diagnosing diseases. In general, the test includes: i) a means for collecting saliva; ii) a means for measuring the amount of one or more lectin-binding components in the saliva; and iii) an oral fluid standard for evaluating the amount of lectin-binding component. Different versions of the compositions and methods of the present invention can be used for various applications.

Preferably the test for predicting caries experience from saliva is easily and accurately interpreted. In one embodiment, the present invention provides a practical test for predicting caries from a single saliva sample of young adults.

In a particular embodiment, the means for measuring the amount of one or more lectin-binding components in a saliva sample comprises a strip test format, analogous to a dot blot test. Preferably the strip test can distinguish multiple lectin-binding component concentrations. A strip test format provides various advantages over other possible designs in its ease of distribution, use, and interpretation.

Accordingly, one embodiment of an assay device comprises a test strip having a sample receiving zone comprising a first matrix material for receiving an aliquot of the saliva sample; and optionally a control zone comprising a second matrix material having at least one control lectin-binding compound of a known concentration bound to the surface of the second matrix material. In one embodiment, a strip of this design is packaged dry.

The test strip preferably comprises a semi-rigid support that has a matrix material laminated to one side of an end of the strip. The support can be made of any suitable rigid or semi-rigid material, such as poly(vinyl chloride), polypropylene, polyester, and polystyrene. Matrix materials suitable for purposes of this invention include, but are not limited to, nitrocellulose, cotton, polyester, rayon, nylon, polyethersulfone, and polyethylene.

The matrix material may be affixed to the support by any suitable adhesive means such as with a double-sided adhesive tape. Alternatively, the support may be a pressure sensitive adhesive laminate, e.g., a polyester support having an acrylic pressure sensitive adhesive on one side that is optionally covered with a release liner prior to application to the matrix material.

Various ways of visualizing the amount of lectin that binds to the matrix-bound lectin-binding component can be used, and many methods are known in the art, such as direct binding of specific visualizing stains (e.g., alcian blue, silver-enhanced alcian blue, or Stains-All); chromophore-labelled lectins; and various indirect methods, such as enzyme catalyzed amplification. The vast majority of the reagents to be used during development of the test are commercially available.

In accordance with one embodiment of the present invention, the lectins may be labeled with a reporter. As used herein, "reporter" refers to a moiety that provides the ability to detect a complex formed between the lectin and the lectin-binding component of the saliva. The reporter may be detected by such characteristics as color change, luminescence, fluorescence, or radioactivity. Examples of reporters include, but are not limited to, dyes, chemiluminescent compounds, enzymes, fluorescent compounds, metal complexes, biotin, haptens, radioluminescent compounds, radioactive-labeled biomolecules, and colored microparticles. One skilled in the art can readily determine a suitable reporter once the type of probe biopolymer to be utilized is determined.

In one embodiment, the labeling procedure may occur prior to analysis (direct labeling) or after complex formation (indirect labeling). Many binding pairs are known in the art for indirect labeling, including, for example, biotin—avidin, biotin—streptavidin, hapten—antihapten antibody, sugar—lectin, and the like. An example of indirect labeling would be the biotinylation of a lectin, contacting the biotinylated lectin with the membrane-bound saliva sample, and reacting of the lectin/lectin-binding component complexes with a streptavidin-alkaline phosphatase conjugate. The lectin moieties that are retained after binding to the lectin-binding components in the saliva then bind to a streptavidin-alkaline phosphatase conjugate, which then acts on a chromogenic substrate, such as Enzyme Labeled Fluorescent (ELF) reagent (Molecular Probes, Inc.).

According to one method of this invention, a test strip of this invention is spotted with a saliva sample and then contacted with a solution comprising a single lectin. In another embodiment, the spotted test strip is contacted with a mixture of lectins. For example, the design of a test strip can be based on either spotting multiple concentrations of the saliva sample (and therefore multiple concentrations of the lectin-binding component) onto a immobilizing matrix and a single intensity of color to be matched against a standard, or a single spot of the saliva sample and multiple intensities of colors to be matched with a range of standard color intensities. The specific design will depend on the kinetics and affinities of various antibody and dye/stain combinations.

For example, an assay device of this invention can comprise a test strip a sample having receiving zone on one portion the strip comprising a first matrix material and one or more lectins bound to the first matrix material; and optionally a control zone comprising a second matrix material having at least one control saliva sample of a known concentration. In this embodiment, detection can comprise contacting the matrix material with a binding partner coupled to a reporter, wherein the binding partner specifically binds the lectin-binding component.

An alternative method of visualizing and quantitating the amount of lectin binding involves the use of particles that can be directly visualized. That is, the lectin can be coupled to a particle, which can be visualized in the test strip upon performing the assay. In another example of this embodiment, the matrix spotted with the saliva sample can be contacted with a mixture comprising a first lectin conjugated to a microparticle having a first color and a second lectin conjugated to a microparticle having a second color, wherein the first and second colors are distinguishable from one another. In one embodiment, the test is performed to determine the risk of dental caries. In this embodiment, the first lectin is positively correlated with DFS and the second lectin is negatively correlated with DFS.

In an alternative embodiment, a method for predicting the risk of a disease in a subject comprises providing an unfractionated saliva sample from the subject; applying a drop of said saliva to a matrix material; contacting the matrix with a mixture of a first set of lectins conjugated to a microparticle having a first color and a second set of lectins conjugated to a microparticle having a second color, wherein said first and second colors are distinguishable from one another; detecting the amount of bound lectins, preferably by visualization by the naked eye; and comparing the amount of bound lectin to the amount known to bind a saliva sample from a control subject, wherein the amount of bound lectin is indicative of the risk of the disease.

For example, each set of lectins may include one lectin or two or more different lectins. Preferably, the first set of lectins is coupled to microparticles of a first color (e.g., blue) in proportions that reflect their contributions in the regression equation, and the second set of different lectins is coupled to microparticles of a second color (e.g., yellow) that is distinguishable from the first color, also in proportions that reflect their contributions in the regression equation. The use of this mixture of two different colors of beads in an assay of this invention provides results in multiple colors on the test strip, e.g., ranging from blue, through the greens, and ending with yellow. In certain cases, the yellow was difficult to see against a white nitrocellulose matrix material. Thus, some red beads were added to the yellow at a ratio of 1:2 to make orange, which is much easier to see, but at that proportion still gives the green intermediate color with blue. Adding red and yellow in a ratio of 1:1 or greater gives brown intermediate colors rather than the green. In this example, the red and yellow beads are coupled to the same lectins.

The visible particles according to this invention are microparticles (i.e., a micrometer-sized particles) that can be directly visualized, such as a dyed particle. Any suitable insoluble particle may be employed for purposes of this invention, including, but not limited to, particles of a polymeric material which may include, but is not limited to, a thermoplastic (e.g., one or more of polystyrenes, polyvinyl chloride, polyacrylate, nylon, substituted styrenes, polyamides, polycarbonate, polymethylacrylic acids, polyaldehydes, and the like), latex, acrylic, latex or other support materials such as silica, agarose, glass, polyacrylamides, polymethyl methacrylates, carboxylate modified latex, SEPHAROSE, methacrylate, acrylonitrile, polybutadiene, metals, metal oxides and their derivatives, silicates, paramagnetic particles and colloidal gold, dextran, cellulose, and liposomes, and natural particles such as red blood cells, pollens, and bacteria. The size of the microparticles used in this invention is selected to optimize the binding and detection of lectin-binding components of saliva, and are typically 0.01 to 10.0 Tm in diameter and preferably 0.01 to 1.0 Tm in diameter, specifically not excluding the use of either larger or smaller microparticles as appropriately determined. In one embodiment, the microparticle is substantially spherical in shape. The preferred microparticle in the present invention is composed of latex containing a colored dye.

In accordance with the invention, the microparticles are coupled to or complexed with a lectin. Methods of coupling proteins such as lectins to particles are well known in the art. For example, in one embodiment, the microparticles possess surface sulfate charge groups that can be modified by the introduction of functional groups such as hydroxyl, carboxyl, amine and carboxylate groups. The functional groups are used to bind a wide variety of lectins to the microparticles, and are selected based on their ability to facilitate binding with the selected lectin. Conjugation of the lectins to the microparticle is accomplished by covalent binding or, in appropriate cases, by adsorption of the lectin onto the surface of the microparticle. Techniques for adsorption or covalent binding of proteins to microparticles are well know in the art and require no further explanation.

The strip test format according to this invention is suitable for a number of different applications, including, but not limited to:

1) A simple strip: this test could be used in a classroom setting to provide a general expectation of caries experience (such as high, medium, low, and very low) for the dentally indigent student, as well as to assess the risk for future caries development. This version would also be appropriate for use in underdeveloped regions so that limited oral health resources can be targeted to those who are deemed most in need of care; thereby supporting cost-effective community-based health programs.

2) A visual high throughput (HTP): this more precise test version would be compatible with multi-analyte technologies, but would still enable quantitation of caries risk leading to prediction of future caries experience. This test might be administered in a dentist's office where, in combination with other wellness tests, appropriate countermeasures could be initiated if warranted.

3) A high throughput (HTP) semi-analytical visual test that could be used on archived salivas without expensive quantitation devices 4) A full analytical test with HTP characteristics. This multi-analyte test requires a capture step involving antisera or lectins.

In a preferred embodiment, the test strip has a uniform design that accommodates, as many ages, races and ethnicities as possible.

In one embodiment, two or three concentrations of a known ligand (i.e., binding partner) of the caries-predictive lectins are incorporated above the matrix to serve as standards or controls. As used herein, the term "ligand" or "binding partner" refers to a member of a pair of molecules and/or compositions capable of recognizing a specific structural aspect of another molecule or composition, wherein the binding partners interact with each other by means of a specific, noncovalent or covalent interaction.

One example of test version of this invention can be used in a non-clinical setting to provide a general forecast of cumulative caries experience, as well as to assess the risk of future caries development (e.g., high, medium, low, very low risk, or zero, for future caries development). This version would also be appropriate for use in underdeveloped regions, so that limited oral health resources can be targeted at those who are deemed most in need of care, thereby supporting cost-effective community-based health programs.

Another test version of the present invention can be used to quantitate dental caries risk leading to the prediction of future caries experience at subsequent ages. This test can be administered in a dentist's office where appropriate countermeasures could be initiated.

Yet another test version is diagnostic and used with medically compromised patients, such as those suffering from diabetes or AIDS. Still another test version features multiple sample, high throughput characteristics. The use of this test version would be used to screening populations of saliva samples, such as those used for epidemiological surveys.

The present invention also provides a diagnostic kit for detecting a disease, comprising: a) a means for collecting a saliva sample; b) a means for measuring the amount of a lectin-binding component in said sample; and c) an oral fluid standard for comparing the amount of said component in said sample. In one embodiment of the present invention, the kit is a Western blot format. In kits of this nature, a drop of a saliva sample is transferred onto an immobilizing matrix (e.g., nitrocellulose filter). The drop is then probed with one or more lectins, and the lectins can then be detected by means of suitable methods.

III. Methods For Preventing Diseases

The present invention also provides methods for preventing or reducing the risk of diseases. In particular, the compositions and methods of the present invention can be used for preventing oral diseases and associated diseases. Once symptoms of associated diseases (e.g., cardiovascular and respiratory diseases) are detected, treatment is difficult and expensive. Thus, treatment results would be much better if individuals could be determined to be at risk prior to symptoms. In this manner, preventive measures could be taken and early intervention strategies could be employed.

In one embodiment, the present invention provides a method for preventing or reducing the risk of a disease in a subject, comprising providing an unfractionated saliva sample from a subject; contacting an aliquot of the saliva with one or more lectins under conditions that allow the one or more lectins to bind to a lectin-binding component of the saliva; detecting the amount of bound lectin; comparing the amount of bound lectin to the amount known to bind a saliva sample from a control subject, wherein the amount is proportional to the risk of a disease in said subject; and administering a therapeutic reagent to the subject when the content of the component in the saliva is above or below the level expressed in normal control (i.e., a subject free from the disease being tested for). In some embodiments, the normal control comprises an oral fluid standard.

A. Oral Fluid Standards

Various oral fluid standards for testing, calibration and standardization of devices and methods for the analysis of oral fluids are well known in the art (See e.g., U.S. Pat. Nos. 5,736,322 and 5,695,929 to Goldstein, incorporated herein in their entirety by reference). U.S. Pat. No. 5,736,322 describes oral fluid standards composed of an aqueous solution of a mucin and a protease inhibitor. A preferred oral fluid standard additionally includes an amylase. Any protease inhibitor that reduces or eliminates proteolytic activity associated with a mucin is suitable. Preferred protease inhibitors inhibit the papain-like (cysteine) proteases. Particularly preferred protease inhibitors include, but are not limited to, leupeptin, antipain, benzamidine, chymostatin, pepstatin A, and aprotinin. In a particularly preferred embodiment, the mucin is present at a concentration ranging from about 0.001% to about 0.4% (w/v); the amylase is present at a concentration ranging from about 0.1 g/L to about 5.0 g/L; and the protease inhibitor is present in a concentration sufficient to reduce or prevent proteolysis of antibodies added to the oral fluid standard.

The oral fluid standards can additionally include one or more components selected from the group consisting of magnesium, calcium, sodium, phosphate, chloride, potassium, and bicarbonate. The oral fluid standard can additionally include a preservative, most preferably a preservative selected from the group consisting of thimerosal, gentamycin, chlorhexidine digluconate, and polyhexamethylene-diguanide.

The standard oral fluid standard can include serum, more preferably human serum. The serum can be positive or negative for an analyte including, but not limited to any of the above-identified analytes. A particularly preferred oral fluid standard includes nitrite at a concentration ranging from about 0.1 mM to about 2 mM; magnesium at a concentration ranging from about 0.03 mM to about 0.6 mM; calcium at a concentration ranging from about 0.5 mM to about 5.0 mM; sodium at a concentration ranging from about 2 mM to about 80 mM; phosphate at a concentration ranging from about 1.8 mM to about 25 mM; chloride at a concentration ranging from about 10 mM to about 56 mM; potassium at a concentration ranging from about 10 mM to about 40 mM; and bicarbonate at a concentration ranging from about 2 mM to about 35 mM. This standard can additionally include a preservative.

Similarly, the oral fluid standards can additionally include one or more analytes. Suitable analytes include, but are not limited to an antibody selected from the group consisting of an antibody to HIV-1, an antibody to HIV-2, an antibody to HTLV-1, an antibody to HTLV-2, an antibody to *Helicobacter pylori*, an antibody to hepatitis A, an antibody to hepatitis B, an antibody to hepatitis C, an antibody to measles, an antibody to mumps, an antibody to rubella, cotinine, cocaine, benzoylecgonine, benzodiazapine, tetrahydrocannabinol, theophylline, phenyloin, β-hCG, thyroxine, thyroid stimulating hormone, follicle stimulating hormone, luteinizing hormone, glucose, insulin, or cholesterol.

U.S. Pat. No. 5,696,929 to Goldstein also describes a saliva standard for measuring the efficacy of saliva collection kits and for comparing and standardizing analytical methods. Generally, the inventive substitute saliva standard has the composition (ingredients presented as mmol/liter): Nitrite 0.1-0.2; Magnesium 0.15-0.6; Calcium 0.5-0.47; Sodium 2-80; Phosphate 1.5-25; Chloride 10-56; Potassium 13-40; Bicarbonate 2-35; Thimerosal 0.01-0.1 g/100 ml; Amylase 0.025-0.1 g/100 ml; Mucin (5%) 0.02-0.5 g/liter; Antipain 0.05 mg/liter; Deionized Water QS to 1 L (approx. eq. 998 ml).

According to one embodiment, in order to test a particular assay, a given amount of the substitute saliva standard is spiked with a predetermined amount of analyte, the desired dilution made, and then the assay is run. The substitute saliva standard could be spiked with, e.g., HIV antibody-positive serum, HIV antibody-negative serum, or any other target analyte which would ordinarily be detectable in human saliva. Representative of such analytes are those mentioned in the aforementioned U.S. Pat. No. 5,103,836 (incorporated herein in its entirety by reference).

B. Anti-Caries Reagents

Various anti-caries reagents well-known in the art can used to practice the methods of the present invention. For example, U.S. Pat. No. 6,136,298 to Gaffar, et al. (incorporated herein in its entirety by reference) describes oral compositions containing a substantially water insoluble noncationic antimicrobial agent, such as triclosan or xylitol for inhibiting *S. mutans* and dental caries. Typical examples of water insoluble noncationic antibacterial agents which are particularly desirable from considerations of effectiveness, safety and formulation are: halogenated diphenyl ethers; benzoic esters; sesquiterpene alcohols such as farnesol, nerolidol, bisabolol, santalol and like compounds; halogenated carbanilides; and phenolic compounds (including phenol and its homologs; mono-, poly-alkyl and aromatic halo-phenols; resorcinol and catechol and their derivatives; and bisphenolic compounds. The noncationic antibacterial agent is present in the dentifrice in an effective antiplaque amount, typically about 0.01-5% by weight, preferably about 0.03-1.0% by weight and most preferably about 0.3-0.5% by weight. The antibacterial agent is substantially water-insoluble, meaning that its solubility is less than about 1% by weight in water at 25° C., and can be even less than about 0.1% by weight.

The preferred halogenated diphenyl ether and most preferred noncationic antibacterial agent is triclosan. Preferred other noncationic antibacterial agents are hexyl resorcinol and 2,2'-methylene bis(4-chloro-6-bromophenol). Xylitol, when present in amounts ranging from about 0.1% by weight to about 40% by weight, also enhances the antibacterial and anticaries properties of the oral compositions described above.

U.S. Pat. No. 5,807,541 to Aberg, et al. (incorporated herein in its entirety by reference) describes compositions and methods for inhibiting the development of caries using non-steroidal anti-inflammatory drugs (NSAIDs) and fluoride reagents. NSAIDS can be characterized into five groups: (1) the propionic acids; (2) the acetic acids; (3) the fenamic acids; (4) the biphenylcarboxylic acids; and (5) the oxicams.

Propionic acid NSAIDs are non-narcotic analgesics/nonsteroidal antiinflammatory drugs having a free —CH(CH$_3$) COOH group, which optionally can be in the form of a pharmaceutically acceptable salt group, e.g., —CH(CH$_3$)COO$^-$Na$^+$. The propionic acid side chain is typically attached directly or via a carbonyl function to a ring system, preferably to an aromatic ring system. Exemplary propionic acid NSAIDS include: ibuprofen, indoprofen, ketoprofen, naproxen, benoxaprofen, flurbiprofen, fenoprofen, fenbufen, pirprofen, carpofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Acetic acid NSAIDs are non-narcotic analgesics/nonsteroidal antiinflammatory drugs having a free —CH$_2$COOH group (which optionally can be in the form of a pharmaceutically acceptable salt group, e.g., —CH$_2$COO$^-$Na$^+$) typically attached directly to a ring system, preferably to an aromatic or heteroaromatic ring system. Exemplary acetic acid NSAIDS include, but are not limited to, ketorolac, indomethacin, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid. Structurally related acetic acid derivatives having similar analgesic and antiinflammatory properties are also intended to be encompassed by this group.

Fenamic acid NSAIDs are non-narcotic analgesics/nonsteroidal antiinflammatory drugs having a substituted N-phenylanthranilic acid structure. Exemplary fenamic acid derivatives include mefenamic acid, meclofenamic acid, flufenamic acid, niflumic acid, and tolfenamic acid. Biphenylcarboxylic acid NSAIDS are non-narcotic analgesics/nonsteroidal antiinflammatory drugs incorporating the basic structure of a biphenylcarboxylic acid. Exemplary biphenylcarboxylic acid NSAIDs include diflunisal and flufenisal. Oxicam NSAIDs are N-aryl derivatives of 4-hydroxyl-1,2-benzothiazine 1,1-dioxide-3-carboxamide. Exemplary oxicam NSAIDs are piroxicam, sudoxicam and isoxicam.

Certain histidine-rich polypeptides ("HRPs," also referred to as histatins) having a substantial proportion L-histidine (i.e., between about 14 and 40 mole and amino acid residues), have antibacterial and antifungal properties, particularly against *S. mutans* and *Candida albicans*. (U.S. Pat. No. 4,725,576 to Pollock, et al.). HRPs are administrable to the loci of infection, particularly in the oral surfaces. Delivery can be by any conventional means, preferably topical means. In the case of oral administration, this would include dentifrices; mouthwashes; denture washes or soaks; denture adhesives or cements; and incorporation into polymers associated within the denture, particularly with the interface of the denture with the gum. Histatin-based peptides having antibacterial and antifungal properties are also described in U.S. Pat. Nos. 5,912,230; 5,885,965; 5,631,228; 5,646,119; and 5,486,503 to Oppenheim et al., each of which is incorporated herein in its entirety.

U.S. Pat. No. 5,801,226 to Cummins, et al. (incorporated herein in its entirety by reference) describes sodium and stannous fluorides, aminefluorides, monosodium fluorophosphate, casein, and plaque buffers such as urea, calcium lactate, calcium glycerophosphate, strontium polyacrylates, as anti-caries reagents.

U.S. Pat. No. 5,013,542 to Hay, et al. (incorporated herein in its entirety by reference) describes compositions containing non-immunogenic amino acid segments of proline-rich proteins for inhibiting the adhesion of disease-causing microorganisms to tooth surfaces. Such microorganisms include, but are not limited to *S. mutans, S. sanguis*, S. sobrinus, *Actinomyces viscosus*, and *Bacteroides* gingivalis. The amino acid segment can be obtained from acidic, proline-rich proteins, such as those derived from human saliva. These proline-rich proteins show marked charge, structural asymmetry and exceptional reactivity to apatitic surfaces. When intact, these proline-rich proteins also promote the adhesion of microorganisms to apatitic surfaces. Because they are derived from human proline-rich proteins, they are recognized as "self" by humans, and antibodies to them have not been reported in humans. The mineral-binding segments can be used as the active ingredients alone or in combination with the other compounds, such as enzymes, antimicrobial agents, etc., in various compositions used for the treatment of the teeth so as to limit the adhesion and/or growth of microorganisms.

The active ingredient can be derived from segmenting a natural or synthetic, proline-rich protein, to provide a non-immunogenic ingredient. The non-immunogenic amino acid segment can be obtained by various techniques, such as by cloning, or by synthesizing analogs of the natural molecules or their segments by chemical means. The non-immunogenic amino acid segment can also be obtained enzymatically or by cleaving the proline-rich protein derived from human saliva by the enzyme trypsin. The removed portion of the proline-rich protein contains the bacterial binding sites. A variety of human, proline-rich phospho-proteins can be employed.

U.S. Pat. No. 6,231,857 to Shi, et al., incorporated herein in its entirety by reference, describes antibodies of *S. mutans*, which can be used in treating dental caries. Specifically, Shi, et al. describe three monoclonal IgG antibodies, each of which specifically binds an antigen on the surface of *S. mutans*. One monoclonal antibody is produced by a hybridoma deposited with the American Type Culture Collection as ATCC No. HB 12559, and is designated SWLA1. A second monoclonal antibody is produced by a hybridoma deposited with the American Type Culture Collection as ATCC No. HB 12560, and is designated SWLA2. The third monoclonal antibody is produced by a hybridoma deposited with the American Type Culture Collection as ATCC No. HB 12258, and is designated SWLA3.

IV. Results

The methods of this invention for predicting the risk of a disease in a subject provide a method for assessing the risk of the disease according to risk levels such as high, medium, low, very low, or zero. For example, in certain populations, 0-2 DFS may be associated with a very low risk of developing caries in young adults, while 3-8 DFS may be associated with low risk, 9-16 DFS with medium risk, and 17 or more DFS with high risk. Thus, for example, according to one embodiment, if the amount of bound lectin is comparable to that for the "very low risk group," it can be predicted that this individual is at risk of developing 0-2 DFS.

In another embodiment, the methods of this invention for predicting the risk of a disease in a subject can further comprises assessing the risk of future development of the disease in the subject. For example, the method of assessing future risk can comprise comparing the amount of lectin binding to a regression analysis derived from a group of subjects expressing a range of disease severity.

In one embodiment, the methods of the present invention provide a correlation between the amount of lectin that binds to a saliva sample, combined with age and gender information, with the number of dental decays (e.g., early-onset dental caries, adult dental caries, root caries, DFT, DMF, DMFS, dfs, dft, draft, dmfs, and dfs/t). The $R^2$ of the regression analysis is preferably at least 0.3 (i.e., any number between and including 0.3 and 1). For example, for a 3-level test, the $R^2$ may be at least 0.9; for a 4-level test, the $R^2$ may be at least 0.98; for a 5-level test, the $R^2$ may be at least 0.99.

In general, according to one method of this invention, a single droplet of saliva is applied to a matrix membrane. This and the standard dots (i.e., saliva samples from a control subject) are then probed with a single lectin or a specific panel of lectins that work together as a mixture to give a single visual test report. The standards are calibrated to be appropriate for as many unique groups as are found. In one embodiment, the test is universalized to accommodate all groups using a test of uniform design.

The amount of bound lectin is visualized, for example, with coupled enzymes, such as alkaline phosphatase or horseradish peroxidase, by a coupled fluorochrome, such as FITC or AMCA, or through the use of lectins that are coupled to colored microparticles. In one example, the lectin result, combined with age and gender, provided a correlation with DFT that has an $R^2$ of 0.90 for a group of individuals that include 7-9 year-old Chinese girls and Hispanic boys as well as 20-25 year-old Asians and Caucasians of both sexes.

The lectin test with the 7 to 25 age span, though forecasting the correct number of DFT, may not be useful for predicting individual risk levels because it simply predicts the number of DFT, regardless of age. For instance, this particular regression equation placed the 25 year-old with five DFT above the 7-9 year-olds with four DFT in spite of the likelihood that the former was in the low to medium DFT for his age group and the latter in the high group for their age. However, if age is removed from the regression equation and the Hispanic and Chinese 7-9 year-olds are considered together as a group and the 20-25 year-old Chinese and Caucasians considered as a group, the following was achieved with the panel of three lectins and gender. The regression equation for the children gave an $R^2$ of 0.972 and a P-value of $2.96 \times 10^{-5}$ against a four-level risk assessment system equivalent to high, medium, low, and very low. The regression equation for the young adults gave an $R^2$ of 0.983 and a P-value of $6.18 \times 10^4$ against the same four-level risk assessment system.

Several different test formats can be used for specialized applications. For instance, one test version could be used in a classroom setting to provide a general expectation of caries experience (such as high, medium, low, or very low) for the dentally indigent student, as well as to assess the risk for future caries development. This version would also be appropriate for use in underdeveloped regions so that limited oral health resources can be targeted to those who are deemed most in need of care; thereby supporting cost-effective community-based health programs. Another more precise test version would be compatible with multi-analyte technologies, but would still enable quantitation of caries risk leading to prediction of future caries experience. This test might be administered in a dentist's office where, in combination with other wellness tests, appropriate countermeasures could be initiated if warranted. A third version would be a high throughput (HTP) semi-analytical visual test that could be used on archived salivas without expensive quantitation devices. A fourth version would be full analytical with HTP characteristics. The use of this variant of the original test would be targeted to screening populations of saliva samples, such as might be envisioned for epidemiological surveys as well as for discovery.

In addition, the use of this test could apply to the risk assessment of additional diseases with which caries experience is correlated or caries experience is found to be an indicator of, or associated with, their risk.

In pre-teenagers, teenagers, and young adults, there are not enough teeth and/or enough exposure time for the teeth to achieve high enough correlations to support individual risk prediction, simply by counting the number of cavities. The method of the present invention bridges these ages of uncertainty by providing significant individual diagnoses of caries risk that could lead to earlier intervention and prevention.

V. Advantages of the Present Invention

The methods, test devices, and diagnostic kits of the present invention present the following advantages over conventional methods and test devices. First, scientific evidence suggests that the MUC7 mucin concentration is likely to be one of the key determinants of the *S. mutans* titers in saliva. Thus, the present invention allows the prediction and diagnosis of the cariogenesis process at an earlier stage than *S. mutans* titer alone, and provides more avenues of prevention.

Second, the experimental results of the present invention show a clear numerical relationship to caries experience, in contrast to currently available technology for detecting *S. mutans* such as DENTOCULT® Strip Mutans ("SM") test strips (manufactured by Orion Diagnostica, Finland). At best, the DENTOCULT® SM test strips can differentiate the *S. mutans* titers in saliva into categories of high, medium, low and none. The present invention is also advantageous over DENTOCULT® strips because of the simplicity and ease of use. In a preferred embodiment, the methods of the present invention can be evaluated in a non-clinical setting by non-technical personnel. In contrast, the DENTOCULT® SM strips must be cultured under sterile conditions and evaluated by a trained, experienced personnel.

The present invention also provides non-invasive compositions and methods for predicting and diagnosing the risk of a disease in a subject. Numerous analytical methods have been developed for determining the presence or absence of, and/or quantifying the amount of various analytes in tissues and fluids of organisms. Currently, most diagnostic testing is done with either blood, urine, fecal material, or tissue biopsy. Testing based on these materials, however, entails substantial invasion of privacy, and poses a significant safety hazard (particularly with testing of blood). In contrast, the collection of oral fluid for testing, including saliva and/or mucosal transudate, entails relatively little invasion of privacy, is relatively safe, and can be accomplished rapidly with relative ease.

Furthermore the methods and test devices of the present invention provide new diagnostic tests for early disease detection, defining individual patient risk of adverse response to drugs, monitoring therapeutic progress, and determining outcomes of treatment. The saliva diagnostic methods and kits of this invention have provide selectivity, sensitivity, appropriate response time, dynamic range (values of interest), representative sampling, reliability or stability as well as the ability to assess multiple substances simultaneously.

The mucin test, as described in U.S. Patent Publication No. 2003/0040009 A1, does not apply to all races or ethnicities. The present invention addresses this issue by providing a universal test which can forecast equally well the accumulated caries history, i.e., DFT (decayed and filled permanent teeth) among various races and age groups. For example, in one embodiment of the invention, the test forecasted equally well the accumulated caries history in Hispanic and Chinese 7-9 year-old children and in Asian and Caucasian 20-25 year-old adults.

The dental examiner cannot reliably identify those who are high or low risk for future caries development simply by counting the number of caries. This is especially true throughout the late pre-teen, teenage, and early adult years, simply because the range of DFT is too narrow to achieve statistical significance for distinguishing the different levels of caries experience. The present invention provides this missing piece of diagnostic information. This leads to earlier, better, more individualized treatment planning. The outcome of the test will also provide a rationale for individualizing the frequency and aggressiveness of preventive measures. With the aid of this tests described herein, the dental examiner will be able to assume the role of oral health care manager to the extent that their individualized intervention could lead to abolition of new caries development even in those who are most at risk.

Another application of this invention is in so-called third world environments, where the tests of the present invention can be used to identify the highest risk individuals in non-clinical settings by non-clinicians. This identification of high-risk children and young adults could lead to targeted treatment, maximizing the effectiveness of limited resources.

The following examples serve to explain and illustrate the present invention. The examples are not to be construed as limiting of the invention in anyway. Various modifications are possible within the scope of the invention.

EXAMPLE 1

The first objective of this study was to confirm and extend the inventors' original findings from the 1991 young adult dataset to a contemporary group of similar composition, recruiting 80-100 students at the USC School of Dentistry.

The second object of this study was to perform a similar study in 7-8 year-old children to learn if the correlations between DFT and mucin concentrations seen in young adults also apply. Analysis of this data provided new insights that are reflected in Example 2.

The third objective was first to better understand the component of MUC7 and MUC5B mucins which appear to have the best association with the forecast of DFT. A second aspect of this aim was then to incorporate these elements into a prototype test with commercial potential.

A. Carbohydrate Studies Leading to Identification of the Most Predictive Element(s) Related to MUC7 and MUC5B Mucin Concentrations.

1. Dot blots: The first objective was to evaluate whether the broader attributes, such as total sialic acid, total carbohydrate, and total apomucin, of the mucins in saliva against a panel of individuals whose DFT and mucin content, as measured by Stains-all, are consistent with the correlation that was noted in young adult Caucasians. A second objective was to use a library of lectins to determine a connection between the content of Lewis and T antigens known to be present on MUC7 mucin in varying amounts, and the caries-prone and caries-resistant individuals identified by our test.

This library of lectins also included the potential to distinguish $\alpha$-2,6 and $\alpha$-2,3 linked sialic acids.

A pilot experiment, using 0.2 µL of whole saliva, quickly revealed that the lectin study is a promising, simple approach to quantitating the main factor associated with caries-resistance. The results of this experiment are shown in FIG. 1. The lectin panel (Vector Laboratories) included Jacalin (Jackfruit seed lectin) and ACL (*Amaranthus Caudatus* Lectin) for different configurations of sialylated T-antigen, AAL (Aleuria Aurantia Lectin) and UEA I (*Ulex Europaeus* Agglutinin I) for different Lewis antigens, SNA (Sanbucus Nigra Lectin) primarily for $\alpha$-2,6 linked sialic acid with some $\alpha$-2,3 activity, and MAL I (Maackia Amurensis Lectin I) for $\alpha$-2,3 linked sialic acid. The saliva of the two boys also contained substantially different levels of mucins (MUC7 at 3078 U/mL [subject #15] vs. 407 U/mL [subject #27], and MUC5B at 3725 U/mL [subject #15] vs. 696 U/mL [subject #27]). This pilot study suggested that the quantity of $\alpha$-2,3 linked sialic acid in whole saliva might embody a DFT-forecasting potential similar to that of Stains-all binding to the two mucins. Indeed, the intensity difference between the spots for subjects #15 and #27, which is 6.9×, and the difference between their combined Stains-all derived mucin concentrations, which is 6.2×, are very similar. Differences in the other lectins can also be seen.

The panel of lectins was repeated with the same two salivas at the equivalent of 0.2, 0.1, 0.05, and 0.02 µL diluted to equivalent spotting volumes of 5.0 µl. This provided a concentration series for each lectin and subject. Linear regressions obtained for all of the lectins with the subject #15 saliva had an $R^2$ of >0.93. The relative differences that are reported have been repeated within the limitations of the dot blot system. The results of this experiment are summarized in Table 1. In this and the experiments that follow, the 0.2 μL intensity value from the regression of each lectin with Griffin #15 saliva is assigned a value of 100 for convenience and all other samples are normalized relative to that value and volume of saliva.

TABLE 1

Evaluation of lectin panel with Griffin subjects #15 and #27

|  | Griffin #15 | Griffin #27 |
| --- | --- | --- |
| JAC | 100 | 320 |
| ACL | 100 | 100 |
| AAL | 100 | 56.5 |
| UEA I | 100 | 26.5 |
| SNA | 100 | 29.4 |
| MAL I | 100 | 14.4 |

Saliva standards indicate that the mucin concentrations have remained stable since the 1990 study as long as they were kept frozen. The lectin assay system was simple and lacked the precision of an established analytical system, but provided repeatable data on a relative scale.

Griffin subject #15 provided a relative standard curve for every lectin using the following amounts of saliva: 0.2, 0.1, 0.05, and 0.02 μL. All spotting volumes were 5.0 μL. The sample was dried on nitrocellulose and reacted with the lectin-biotin complex.

After washing, the nitrocellulose was bathed in avidin-alkaline phosphatase. Color development was with NBT/BCIP that was allowed to continue until there was a range of color intensities. Quantitation was accomplished by measuring the average color intensity on a transect of the diameter of the dot blot.

TABLE 2

| YEAR | STUDY | SUB. # | AGE/SEX | RACE/ETHNIC | MUC7 resting | MUC5B resting | DFT (H, L) | S. MUTAN (H, L) | JAC T-antig. | AAL Lewis | UEA I Lewis | SNA α-2,6 | MAL I α-2,3 | MAA α-2,3 |
| --- | --- | --- | --- | --- | --- | --- | --- | --- | --- | --- | --- | --- | --- | --- |
| 1991 | Aging | | | | | | | | | | | | | |
| | | 8 | 26/M | Cauc | 1505 | 344 | L | — | 107 | 62.9 | 40.2 | 51.6 | 44.9 | 78 |
| | | 17 | 21/F | Cauc. | 170 | 922 | H | — | 56 | 2.3 | 0 | 20.0 | 0 | 10 |
| 2000 | S. mutans | | | | | | | | | | | | | |
| | | 3 | >65/? | Cauc. | <6 | 281 | — | H | 270 | 8.2 | 19.3 | 18.3 | 37.5 | 22 |
| | | 7 | >65/M | Cauc. | 805 | 624 | — | L | 240 | 88.7 | 12.8 | 39.6 | 167.5 | 42 |
| 2002 | Griffin | | | | | | | | | | | | | |
| | | 3 | 7/F | Chin. | 1863 | 1082 | H | — | 200 | 42.1 | 12.3 | 47.6 | 19.5 | 70 |
| | | 4 | 8/F | Chin. | 1191 | 289 | H | — | 559 | 53 | 21.8 | 49.7 | 6.3 | 58 |
| | | 5 | 7/F | Chin. | 1438 | 160 | H | — | 421 | 39.6 | 14.9 | 29.9 | 14.3 | 10 |
| | | 10 | 7/F | Chin. | 631 | 504 | zero | — | 1034 | 55 | 21.8 | 52.6 | 23.8 | 45 |
| | | 13 | 7/F | Chin. | 7 | 612 | zero | — | 399 | 20.5 | 21.9 | 52 | 30.5 | 36.5 |
| | | 15 | 7/M | Hisp. | 3078 | 3725 | zero | — | 100 | 100 | 100 | 100 | 100 | 100 |
| | | 27 | 8/M | Hisp. | 407 | 696 | H | — | 320 | 56.5 | 26.5 | 29.4 | 14.4 | |
| 2002 | USC | | | | | | | | | | | | | |
| | | 4 | 21/F | Asian | 2192 | 2743 | H | — | 354 | 76.6 | 2.2 | 61.3 | 8/5 | 70 |
| | | 35 | 26/M | Pac. Isl. | 765? | 20 | H | — | 78.1 | 6.8 | 2.4 | 10.7 | 7.0 | 9.5 |
| | | 42 | 23/F | Asian | 5767? | 2048? | zero | — | 221 | 63.7 | 12.7 | 51.6 | 70.5 | 82 |

This experiment confirms the contention from the previous experiment, that the amount of α-2,3 linked sialic acid is the most distinctive difference between the two salivas. The SNA result further supports the prominence of sialic acid. AAL and UEA I suggest that the amount of Lewis antigen, especially the variety with α-1,2 linked fucose, may somehow be interwoven in the relationship between mucin and DFT. On the other hand, the quantity of the form of T-antigen that is recognized by Jacalin may be a negative factor. Based in part on this experiment, ACL was dropped from the lectin panel and MAA (Maackia amenurensis, EY Laboratories) was added for evaluation of the broader panel of salivas. MAA, like MAL I, also shows a preference for α-2,3 over α-2,6 linked sialic acid, but it has other differences that may be useful in our application.

A panel of salivas was assembled from five different groups and spans the time period from our first study (1990) to the present. Half of the panel members exhibited an inverse relationship of MUC7 mucin concentration to DFT, and the remainder exhibited a direct relationship, e.g., high mucin and high caries or low mucin and low caries. The characteristics of each subject and their relative responses to the six lectins are shown in Table 2.

The patterns of reactivity are different for each lectin. The high or low DFT assignment was based on the relative numbers of DFT within each subject's peer group. The high titer of S. mutans referred to >$10^6$ and low to <$10^5$ cfu. The salivas from the S. mutans study were not included in the following calculations because of subject age and, lack of access to their DFT. The degree of correlation with DFT (H or L) differs for each lectin and is shown for the remaining salivas in Table 3.

TABLE 3

Regressions and Correlations Analyzing the Lectin Affinities to Whole Saliva Reported in Table 2

| Variable(s) | R | $R^2$ | Adj. $R^2$ | P-value |
| --- | --- | --- | --- | --- |
| A. MUC7 + MUC5B vs. DFT (H/L) | −0.35 | 0.12 | 0.00 | NS |
| B. MAL I vs. DFT (H/L) | −0.76 | 0.57 | 0.53 | 0.004 |
| C. SNA vs. DFT (H/L) | −0.59 | 0.34 | 0.28 | 0.05 |
| D. MAL I + SNA vs. DFT (H/L) | −0.76 | 0.57 | 0.48 | 0.02 |
| E. MAA vs. DFT (H/L) | | | 0.16 | NS |
| F. UEA 1 vs. DFT (H/L) | | | 0.22 | <0.10-->0.05 |
| G. AAL vs. DFT (H/L) | | | 0.06 | NS |
| H. JAC vs. DFT | | | 0.00 | NS |
| I. MAL I + JAC vs. DFT (H/L) | −0.83 | 0.69 | 0.62 | 0.005 |
| J. MAL I + JAC + AAL vs. DFT (H/L) | −0.89 | 0.78 | 0.70 | 0.005 |

The diverse nature of the saliva panel is evidenced by the fact that neither the MUC7 or MUC5B mucin nor the combination of the two has but a weak, non-significant correlation with DFT (Table 3, row A). MAL I shows the highest individual correlation with DFT and except for a relatively narrow range of lectin reactivity between high and low DFT, there is no overlap (Table 3, row B). SNA shows the next best individual correlation with DFT (Table 3, row C), but in combination with MAL I, the strength of the relationship to DFT is not improved (Table 3, row D). MAA, UEA I, and AAL all exhibit measurable correlation, but do not achieve significance (Table 3, rows E-G). Jacalin (JAC) is not correlated with DFT (Table 3, row H), however it does appear to contribute substantially to the correlation when included with MAL I (Table 3, row I). Inclusion of AAL in the multiple regression yielded the highest $R^2$ observed with the lectins alone (Table 3, row J).

Interestingly, MAL I, SNA, MAA, UEA I, and AAL are all significantly correlated with each other. JAC is not significantly correlated with any of the other lectins. These results suggest that the sialic acid-specific lectins are primarily associated with Lewis antigens and not T-antigen. However, none of the other lectins improve correlation when combined with MAL I. The exception is that after MAL I and JAC are combined then AAL contributes a further substantial improvement (Table 3, rows I and J).

When compared with the mucin concentrations, SNA, MAA, AAL, and MAL I are each significantly correlated with MUC5B mucin concentration. Only MAA, AAL, and MAL I showed correlation with MUC7 mucin concentration. In the unusual combination of MAL I reactivity and MUC5B concentration, there was an improvement of the overall relationship to DFT to an $R^2$ of 0.59.

Figure 2:
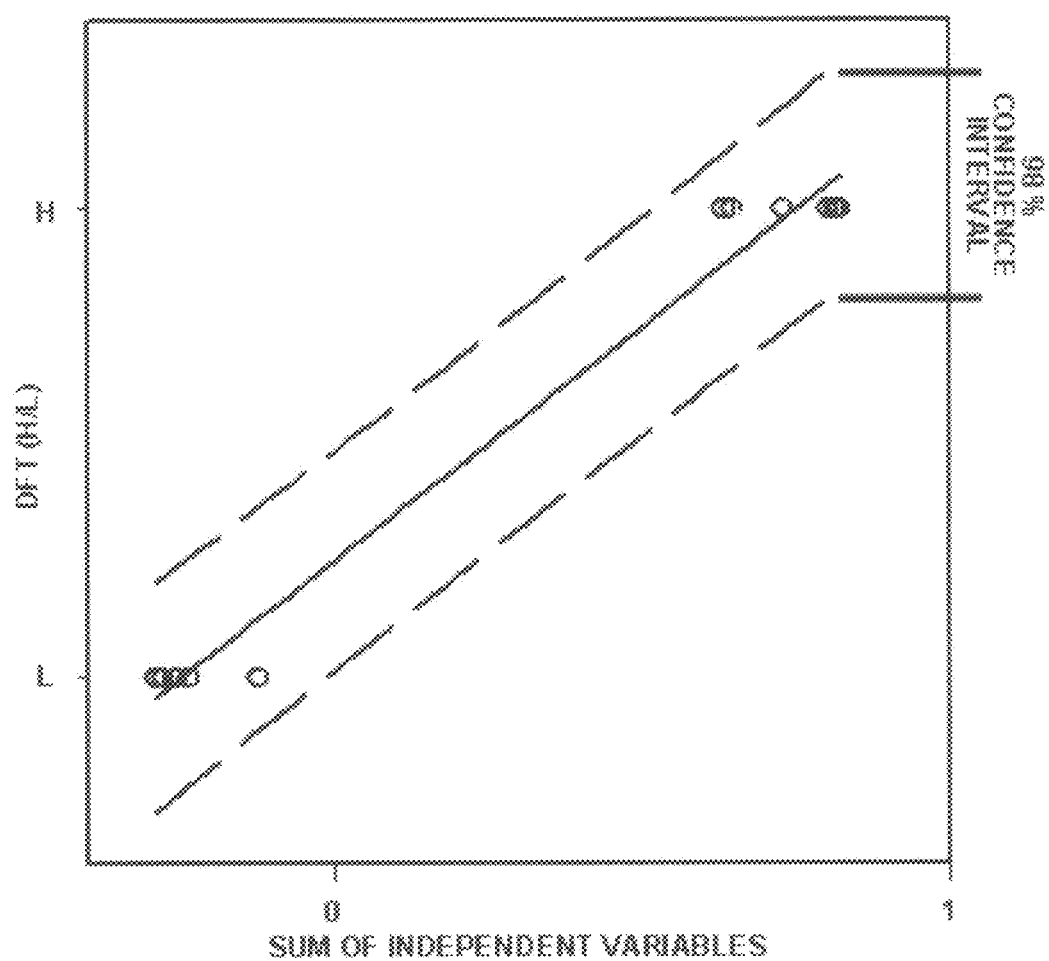
FIG. 2 describes a linear regression analysis of DFT versus the sum of independent variables (MAL I, JAC, MAA, MUC7 mucin, MUC5B mucin, gender, and age) for forecasting DFT with representative 98% confidence levels.
Figure 3:
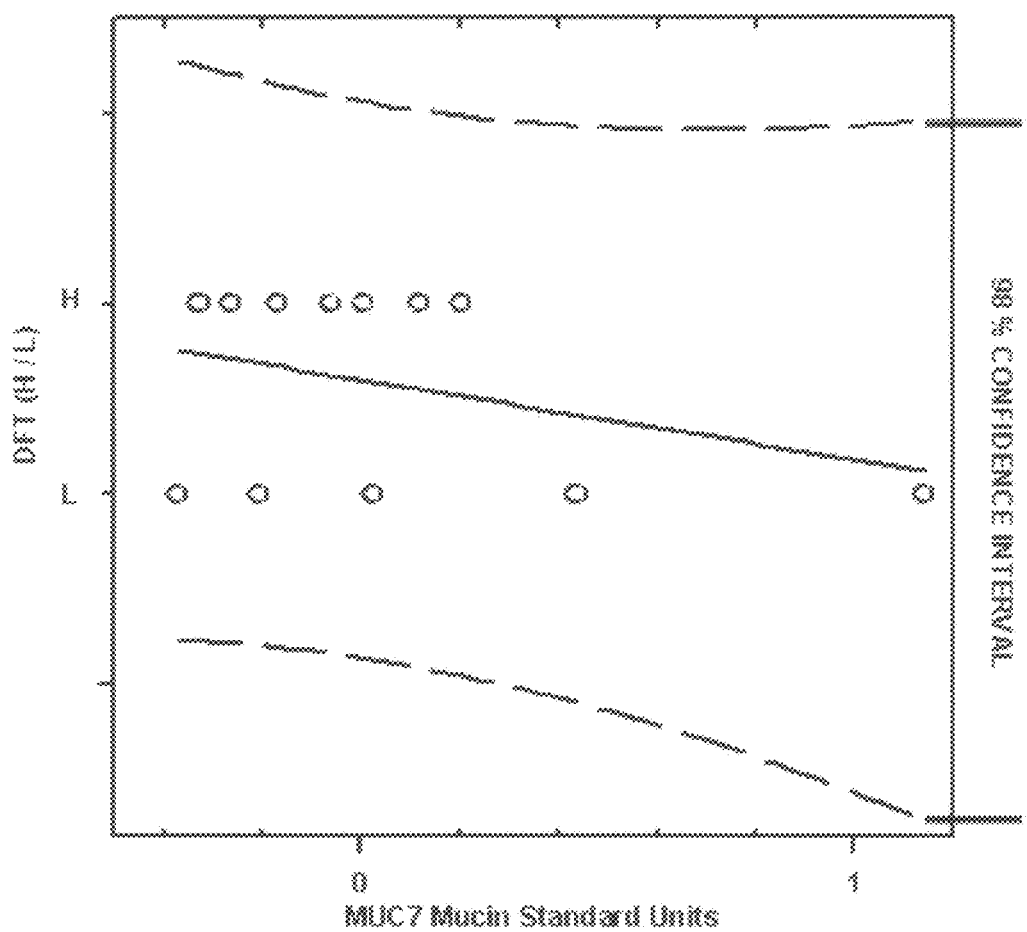
FIG. 3 describes a linear regression analysis for the relationship between MUC7 mucin alone and DFT with representative 98% confidence levels for the same subjects analyzed in FIG. 2.

The potential for one of the mucins to improve the regression equation led us to broaden the search to include age and gender, as well as the two mucins. The result was that a combination of independent variables was found that yielded an $R^2$ of 0.932. The significance of the regression equation was p=0.015 with satisfaction of normality, constant variance, and power tests. The independent variables followed by their relative contribution to the regression equation in parentheses are MAL (49%), JAC (6%), MAA (3%), MUC7 mucin (14%), MUC5B mucin (6%), gender (10%), and age (12%). By standardizing the contribution of each independent variable with the regression formulas, and then taking the sum of these values for each individual, the complex outcome of the relationship can be visualized by a simple linear regression graph as shown in FIG. 2. The graph illustrates that there are no overlaps between high and low caries experience for children and young adults of both genders and at least three different ethnicities, Chinese, Hispanic, and Caucasian. The population confidence interval was programmed at 98%. Thus, given the above information, a prediction of high or low caries experience can be made with high accuracy. FIG. 2 also demonstrates the potential for insertion of a highly significant middle range of caries experience as more data becomes available. The data shown in FIG. 3 demonstrates that the information needed to predict caries experience with high probability is still contained in the data even though the individuals represented near opposites with regard to MUC7 mucin concentration.

Development of an analytical test for the high throughput application that uses multiple independent data inputs requires the testing of multiple analytes on an automated format. The MAL I affinity for a subset of α-2,3 linked sialic acids provides a strong link to the forecast of DFT. An alternative approach to the strip test is the dot blot approach, as used above, which works with whole, unfractionated saliva. This greatly simplifies development, manufacture, packaging, and storage procedures. A preferred test strip provides $R^2$'s of 0.90 or better.

The information obtained from this Example suggests the possibility that whereas the two mucins are the primary carriers of the MAL I reactivity in Caucasians, in Asians there may be different molecules involved. Western blots analysis described in Example 2 provided definitive information in this regard.

Figure 4:
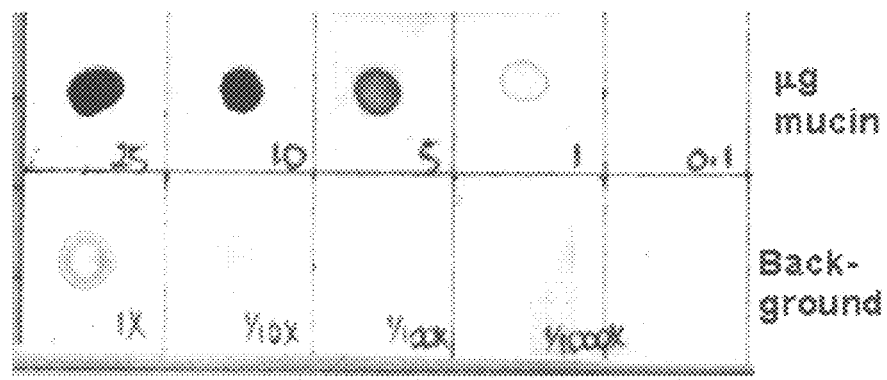
FIG. 4 is a dot blot of mouse sublingual mucin probed with specific antibody-secondary antibody HRP.
Figure 5:
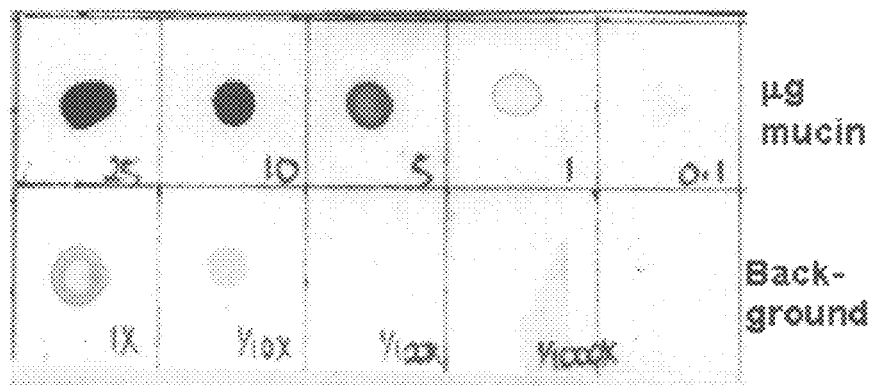
FIG. 5 is a dot blot of mouse sublingual mucin probed with specific antibody-secondary antibody-AP.

B. Tests for simple, reliable disclosants for the mucin's predictive element(s) that can be adapted to the above tests. The inventors' experience with quantitating dot blots demonstrated that this represents a greater potential for developing future tests than the PAGE approach that has been used extensively to this time. FIGS. 4 and 5 illustrate the linear potential, as well as a metachromatic color option, in a model system that used mouse sublingual mucin. As far as the MUC7 mucin relationship to DFT in Caucasian young adults, only a three-fold difference in concentration was needed to distinguish the three significant classes of caries experience. The dot blot can easily be calibrated to distinguish the two threshold concentrations required to assess the three levels of risk.

Figure 6:
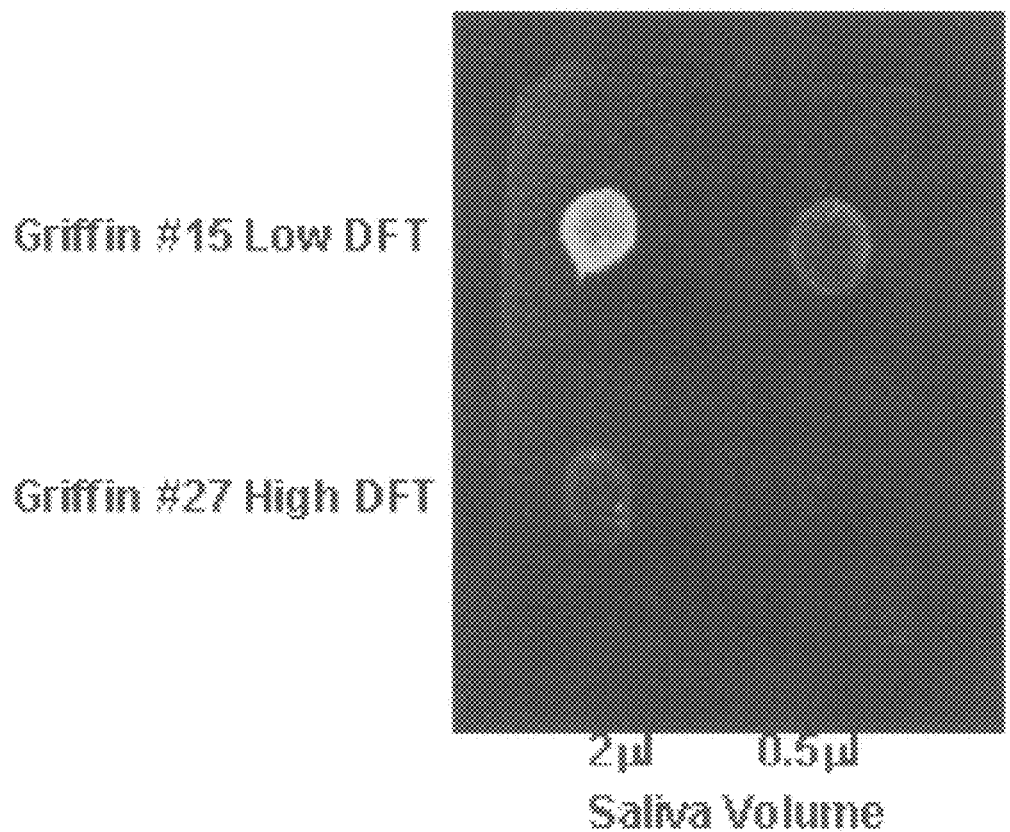
FIG. 6 is a dot blot of whole saliva from children with Low and High DFT following MAL I and AMCA incubations and long wave W.

FIG. 6 shows an example of the dot blot format. Using salivas from the two Hispanic boys featured in FIG. 1 and Table 1, a dried droplet of their whole saliva was probed with MAL I-biotin followed by avidin-AMCA. The result is a direct digital image of the fluorescence produced by long wave UV irradiation. The difference is striking and represents approximately a six-fold difference. The four-fold serially diluted homologous saliva samples also reveal easy differences to distinguish visually.

EXAMPLE 2

The purpose of this study was to "universalize" and complete development of several iterations of a simple, non-invasive saliva test not only for forecasting individual accumulated caries experience but, more importantly, for assessing levels of risk for future caries development. The test can be integrated into dental practice as a common diagnostic procedure health screening, and in broader oral health campaigns to improve identification, treatment, and prevention in high-risk individuals. The diagnostic screening information provided by these combinations of test and technology will aid the health care provider in identifying caries-prone children, teen-agers, and young adults. This will be most helpful at stages of dental development when physical examination alone or dmfs (decayed, missing, and filled surfaces) in deciduous teeth and DMFS in permanent teeth cannot identify with statistical certainty, those individuals who are at-risk.

Additional factors in saliva, which may or may not be associated with mucins, were identified and evaluated by lectin affinities for the property of caries prediction, and then were developed into a caries risk test suitable for commercialized. The assays provided factors that are better and more broadly applicable risk indicators than MUC7 and MUC5B mucins alone. With these factors, groups of children and young adults, for whom the mucins may not be forecasters of accumulated caries experience, can still be identified with high probability, even when grouped together with individuals for whom the mucins are indicators. These additional factors can be quantitated with less difficulty than the mucins and present greater opportunity for developing simple, reliable tests.

A. Background

1. Epidemiological studies leading to caries risk prediction: There have been numerous models generated for caries risk assessment, and they are rarely identical in design. A review of the caries risk assessment literature through 1989 concluded that: 1) clinical variables were better predictors, 2) the most significant indicator was past caries experience, and 3) regression analysis was the preferred statistical approach (Newbrun, E. and Leverett, D., *Risk Assessment in Dentistry*, Bader, J. D., ed. Chapel Hill: University of North Carolina Dental Ecology, 1990, p. 304; Powell, L. V. *Community Dent. Oral Epidemiol.* 26:361-371 (1998)). The literature published between 1989 and 1997 confirmed the preeminent role of past caries experience in caries risk prediction (Powell, supra). The most accurate models for risk assessment have also included bacterial levels. Assessing this information from a longitudinal perspective, as reviewed by Powell (supra), the present inventors noted that past caries experience is the only predictor of significance identified in every age group. Thus, to the extent that past caries experience or DFT can predict the level of caries risk, the forecast of past caries experience or DFT is also predictive.

The review by Powell also notes that there have been no caries risk studies of young adults (18 to 33 years of age). Another relevant observation was made in the NIH-sponsored epidemiological study entitled "Oral Health of United States Adults" (A. J. Miller, et al., *Oral Health of U.S. Adults, NIDR.* 87-2868 (1987)). Here it was shown that the decayed and filled surface measurement (DFS) on coronal surfaces is an accurate, linear record of initial incidents of caries formation until about age 40. Beyond that age, this clinical indicator becomes less and less reliable as an indicator of the long-term rate of caries formation. The subjects included in a study conducted by the present inventors, which harbored the discovery of the strong correlation between saliva mucin concentrations and DFT, ranged from 18 to 33 years of age, filling the gap in age groups that exists in the literature for prediction of caries risk. In addition, it appears that this age group embodies the period when the accurate record of first-time caries experience approaches its maximum range of expression.

2. The science of caries risk prediction and the multifactorial nature of cariogenesis: A recent review in this area upholds the long-held view that cariogenesis is multifactorial (M. Lenander-Lumikari and V. Loimaranta, *Adv. Dent. Res.* 14:40-47 (2000)). However, equally important is the principle that correlation does not determine or require any apparent known causal relationship. The variables tested in many of the caries risk studies are often far removed from any apparent or known direct relationship to cariogenesis (Powell, supra). Thus, because of the practical, predictive theme of the proposed project, developing a hypothesis that rationalizes the multifactorial nature of cariogenesis and the high coefficient of determination ($R^2$) between DFT and concentrations of saliva components is not critical to success. A model that explains approximately 90% of the variation in DFT, such as contained in our report for 24-33 year-olds, does not preclude existing data suggesting that cariogenesis is multifactorial. The review by Lenander-Lumikari and Loimaranta (supra) concludes that other than the early clinical signs that support caries formation, such as plaque build-up and enamel erosion, there is no single factor that can be viewed as having a broad, unified impact on the initiation of caries formation in individuals. Thus far, only low impact factors have been identified, leaving a huge void in quantitative assignment of the relative effects of various factors on cariogenesis. While not wishing to be bound by any particular theory, the inventors believe that mucins and other components in saliva are important factors that fill this void, permitting regression analysis with significant predictive potential.

3. Potential for the saliva test for caries risk to improve oral health care: The ability to predict the level of risk of future caries development creates the opportunity to "fine-tune" prevention. Scientifically based, individually appropriate modalities and spacing of preventive treatments, e.g., quarterly vs. semi-annual or annual visits, could be integrated into each patient's long-term treatment/prevention plan. This would be especially appropriate for children and young adults who otherwise might expect to develop substantial numbers of new caries as they grow older.

A second area oral of health care that the test could benefit is in the targeted treatment and prevention of high-risk children and young adults in third-world environments. Here, targeted application can maximize effectiveness of limited resources.

B. Model Three-Level Risk Test Based on Mucin Concentrations.

A model for forecasting accumulated caries experience was developed from our earlier young adult group. The model was targeted to MUC7 mucin concentration in the 24-33 year-old group and thus limited in its scope. However, in the course of working with the data to achieve this goal, several strategies became apparent that may be generally applicable to building future models for prediction. The first of these is that the goal of three non-overlapping zones of significant prediction may be achieved several ways in the same group of individuals. In addition, different combinations of independent variables may be used to achieve the three-level goal in different groups of individuals. In this particular regression analysis, there was only a three-fold difference in mucin concentration between high- and low-caries groups. Thus, once the analytical data is processed and these thresholds have been identified, future tests need to be calibrated only at the two threshold concentrations to complete a three-level test. Finally, since mucin concentrations and DFT are continua in the population, there will be legitimate borderline individuals who must be accounted for by the model.

The model developed for the 24-33 year-olds is as follows: 1)<400 MUC7 mucin units/mL=high risk/caries prone (25%); 2) 400-1200 MUC7 mucin units/mL=medium risk (58%); and 3)>1200 MUC7 mucin units/mL=low risk (17%). In this example, the threshold concentrations between high and medium and medium and low DFT coincide with the points at which the parallel confidence interval lines cross over the regression line. Individuals with borderline concentrations of mucin are best placed in the next higher risk category in order to avoid the error of predicting too low, which would have serious health consequence. The percentages listed above, next to the risk level, are that proportion of the model group who resides within the risk level. The distribution is similar to that found in the general population (U.S. Dept. of Health & Human Services. National Institutes of Health Consensus Development Conference Statement. *Diagnosis and Management of Dental Caries Throughout Life* (2001)). The major elements covered in this model can be replicated in any other predictive relationship that is exploited for the caries risk test.

Another phenomenon that was noticed in the young adult group of 12 years ago was that in those individuals with no detectable MUC7 mucin, DFT was perfectly correlated ($R^2$=1.00) with age over the range of 21 to 33 years. This allowed for calculating a rate of caries development in this group at 0.83 new DFT per year. If this was not a completely serendipitous occurrence, then we might find in our current subjects, a subgroup that will develop new caries at a relatively rapid, predictable rate. A group such as this would greatly facilitate clinical studies of potential caries preventives both in time, number of participants, and level of potential statistical certainty.

For any test to proceed to commercialization, the test and the prediction model must be validated. This is accomplished not only by accepted protocols for "blinding" the second-half phase of data collection and analysis, but also by analyses that reveal the type, frequency, and magnitude of errors, as well as for the usual measures of sensitivity and specificity.

C. Test Composition that Achieves a Lectin-Based, Three-Level Caries Risk Test.

Development of a caries risk test using a single droplet of saliva is extremely attractive because, in addition to simplifying the design and use of a strip test, it "globalizes" the predictive element(s) in saliva and accommodates the possibility that mucins may not be the only carriers of the predictive element. Cases in point are the Griffin subjects #3, 4, 5, 10, and 13. These children go completely against the inverse relationship between mucin concentration and DFT identified in the original study of young adult Caucasians. Subjects 3, 4, and 5 have relatively high concentrations of mucin and high DFT for their age, and subjects 10 and 13 have relatively low concentrations of mucins and zero caries. However, when the saliva panel is screened with lectins, a combination of factors can be assembled that still correctly forecasts each individual's caries load. From this the inventors concluded that factors other than the mucins may also carry the predictor elements and that there may be individual differences in the molecules that are associated with these elements. This possibility was explored by Western blot analyses of the panel salivas, as shown in Table 3 and FIG. 2, using the lectins that have been shown to be contributors to the predictive regression equations.

The regression equation that is illustrated in FIG. 2 used input from three lectins, both mucins, and two "fixed" variables, age and gender. With respect to the analytical test (vs. the strip test), if a dot blot high throughput format is used, the required lectin information could be acquired by multiple assays as above. The mucin concentrations could be acquired by antibody binding as illustrated in FIGS. 4 and 5. All of these assays could use the same avidin conjugated reporter, and all have been demonstrated to work within the dot blot format. The fixed variables are easy to interpret and factor into the analysis leading to the individual prediction.

The design of the strip test preferably provides simplicity and ease of use, while still achieving the three zones of significance. Preferably, the strip test is accomplished with a single spot of whole saliva that can be compared to two standard spots, which represent the two thresholds between high and medium and medium and low caries risk. One-step reporting and visual reading are also desirable and are discussed below. As noted for the analyses with the young adult data, the goal is equally achievable by different strategies or combinations of independent variables. In the case of the saliva panel, the $R^2$ can be substantially improved to 0.983 from 0.932 (FIG. 2) by inclusion of ethnicity. This provides the opportunity to drop MUC5B concentration from the equation with a relatively small loss of $R^2$ to 0.961. An $R^2$ of 0.90 or higher is the benchmark for achieving the significant three levels of prediction. If MUC7 mucin concentration is dropped from the equation, the $R^2$ falls to 0.421, even though its influence amounts to only 17.2% of the outcome.

One object of this study included screening with additional lectins to find a substitute for MUC7 mucin. Success in employing only lectins and fixed variables for the test allowed for the exploration of the use of a single reporter solution for reacting the strip that is composed of a mixture of the important lectins, calibrated to proportions that are equivalent to their contribution to the regression equation. If all lectins are conjugated to the same reporter molecule, the intensity of the dot should be equivalent to their sum. Further calibration achieves the appropriate responses within the range of the test.

There are many other options available for possible design of the strip test. For example, the inventors have shown that at least for young adult Caucasians, MUC7 mucin concentration can be used alone and satisfy the goal of three significant non-overlapping zones of prediction. This embodiment was designed for the whole saliva/dot blot format by using an antibody to MUC7 mucin sandwiched with the reporter. Different tests can be specifically designed and calibrated for gender, age, and ethnicity or race. For example, MAL I can be used to predict caries risk in both Caucasians and Hispanics. Preferably, the test is universalized as much as possible to avoid the problem that many individuals are a blend of ethnicities or races.

Another strategy that can be used to achieve the goal of three non-overlapping significant zones of prediction with the whole saliva/strip test format is the design of the regression analysis. Because caries-free has no variation, the test includes a reporter threshold above or below which reside all of the caries-free individuals. This group is automatically placed into the low caries risk group. The remaining individuals are then statistically grouped into medium or high-risk profiles. The value of this approach is that it is a realistic approximation of this age group, and the statistical demands for achieving the remaining two non-overlapping zones of significance are greatly relaxed and much easier to achieve.

a. Capture strategies. One approach to development of a strip test for caries uses capture strategies. This involves covalent attachment of an antibody or lectin to the strip, incubating with the saliva sample, rinsing and then reacting the strip with a second antibody or lectin linked to a reporter. The advantage of this approach is that the test can be developed with the option of two levels of specificity. For example, in one embodiment an antibody directed to the non-glycosylated 3' end of MUC7 can be used for capture, which then allows for probing the mucin with any of the lectin-reporter complexes that might have predictive potential. In another embodiment, the apomucin portion of the captured mucin is quantitated with a second antibody which is directed at the non-glycosylated 5' end of the mucin. In yet another embodiment, all saliva components that have a particular oligosaccharide configuration are captured using a lectin and then probed with a second lectin coupled with the reporter. For example, MAL I and MUC7 mucin along with the three fixed variables (age gender and ethnicity) gave an $R^2$ of 0.891 for members of the saliva panel.

b. Test disclosants. The goal for this part of the process was to develop a one-step procedure that involves a single incubation of the dried spot of saliva with a lectin-reporter complex, two rinses with water or buffer, and visual comparison of the saliva spot with a pair of calibrated standards. The fluorescent spots shown in FIG. 6 demonstrate the success of this protocol. The biotin and avidin complexes were combined and the resulting biotin-avidin complex was purified before incubation with the saliva blot. The fluorescent reporter was AMCA, which is activated by long wave UV and fluoresces in visible blue light. This is a useful reporter because long wave UV lamps are common and inexpensive (black light).

Alternatively, the strip test is evaluated by an enzymatic reaction, such as alkaline phosphatase or horseradish peroxidase. In one example, avidin conjugated to alkaline phosphatase was used for the assessment of the saliva panel with lectins, as shown in FIG. 1 and Tables 2 and 3.

The tests strips of this invention have broad application in the field of strip tests and other visually oriented diagnostic tests. In one embodiment, reporters can be used that alter the local pH and then assess the relative quantity of the reporter with a pH indicator. For example, protein derivatizing agents have been identified that add carboxyl groups to proteins. These derivatizing agents can be used to add carboxyl groups to the avidin that reacts with the lectin-biotin complex. When a drop of pH indicator is added, the color change can be noted, which is relatively proportional to the amount of bound avidin.

c. Test devices. In one embodiment the high throughput (HTP) test system is PAGE-based, which has both analytical and visual capabilities. In another embodiment, the high throughput analytical application is similar to the strip test except that many different saliva samples are pattern spotted on a nitrocellulose surface, communally reacted with the combination of the lectin-reporters, communally washed and reacted with a color- or fluorescence-generating signal. The actual quantitation is accomplished with a plate reader such as used for interpreting arrays. For example, the lectin-AMCA complex is suitable for this application because the quantitation can be judged against the blue color intensities of a pair of standards, high and low thresholds, revealed by long wave UV.

d. Test kits. Test kits provide the ability to validate the test in the group and to resolve potential issues that may be dependent on ethnicity, races, or ages, etc. Suitable formats for the test kits include the dot blot format and the PAGE system. The kit can include sampling devices, a pre-programmed calculator, standard instructions for non-X-ray dependent diagnosis of DFT, a test detection device, and the supplies to perform the required number of tests.

EXAMPLE 3

A Lectin-Based Four Level Caries Risk Test

This study demonstrated that certain combinations of lectins, such as MAL I, JAC and SNA, together with gender information, yields a good correlation with DFT in a statistical anaylsis by regression. This model provides four statistically different groups: high, medium, low and zero DFT into which a tested individual can be placed.

Figure 7:
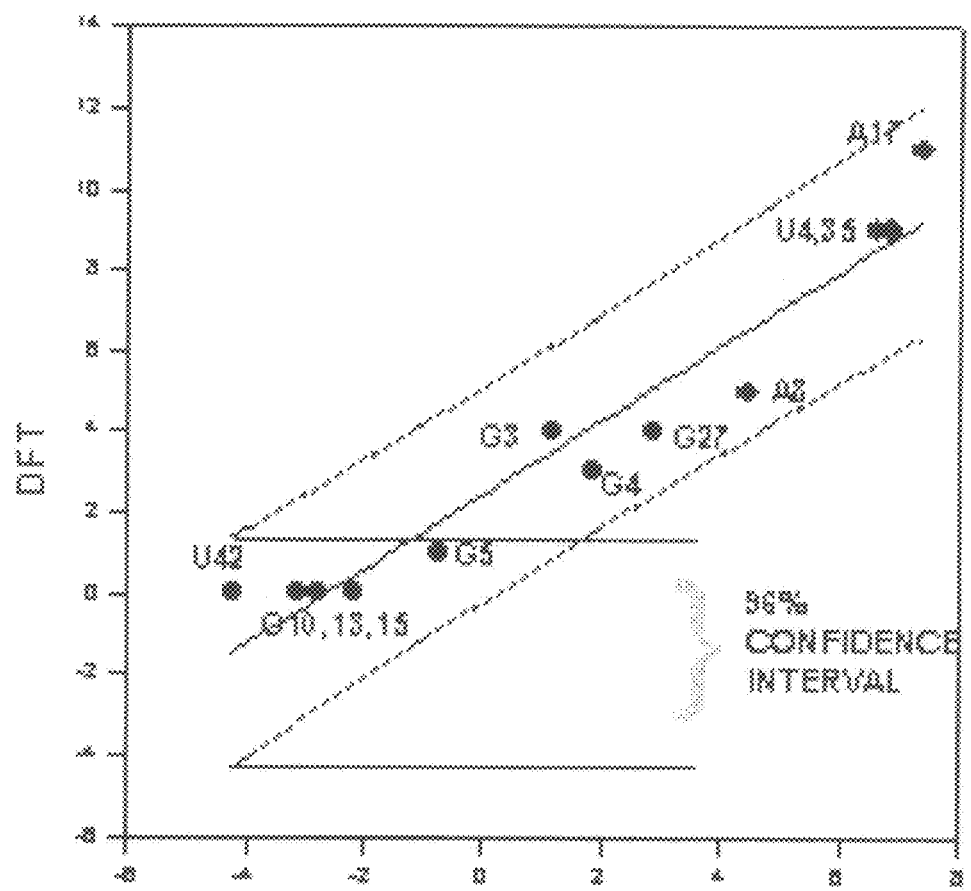
FIG. 7 describes a linear regression analysis of DFT versus the sum of independent variables (MAL I, JAC, SNA, ethnicity, and age) for forecasting DFT with representative 96% confidence levels.
Figure 8:
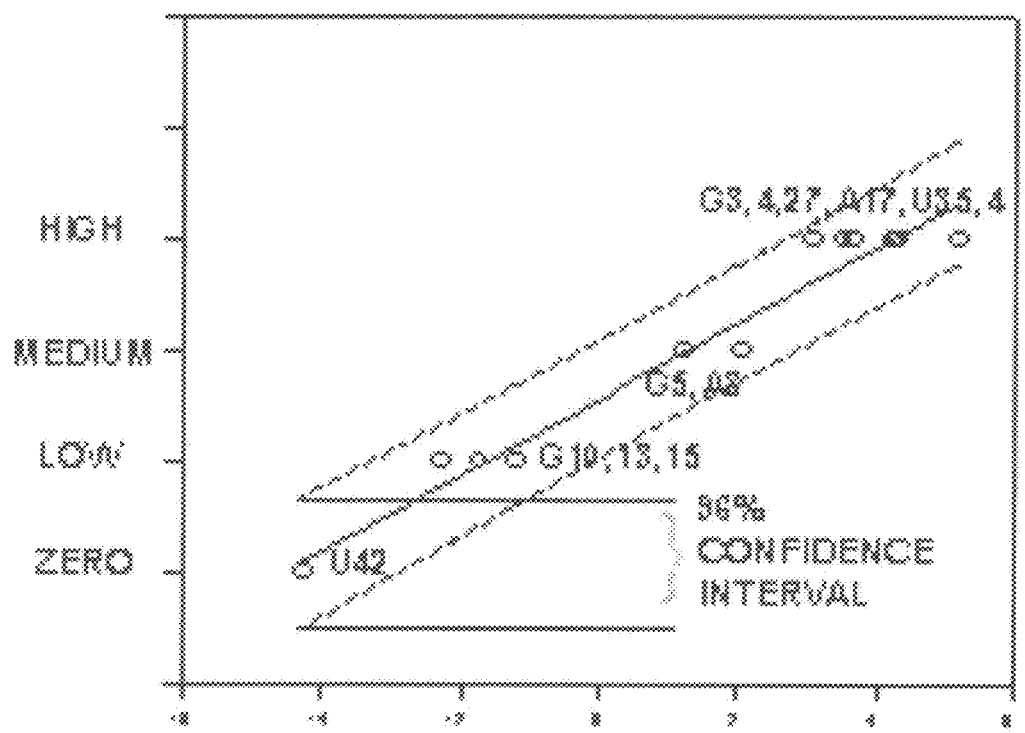
FIG. 8 describes a linear regression analyses of high, medium, low, and zero risk versus the sum of independent variables (MAL I, JAC, SNA, and gender) for forecasting DFT with representative 96% confidence levels.
Figure 9:
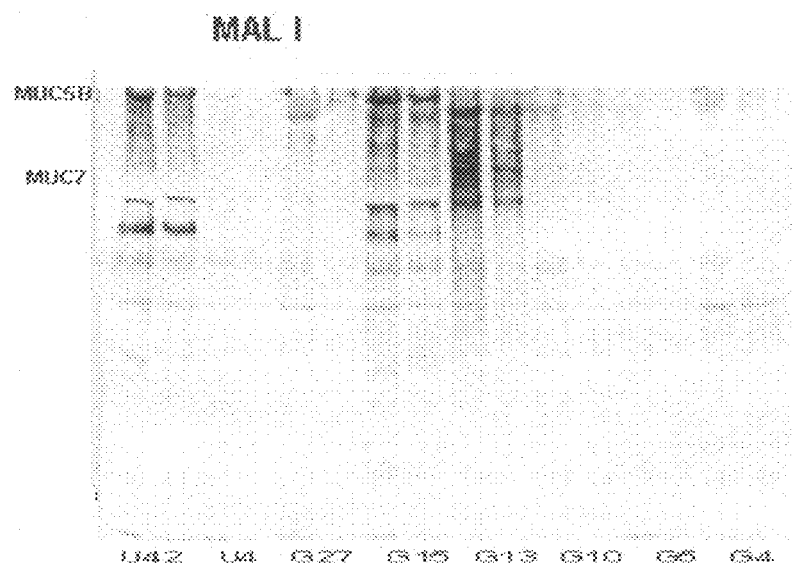
FIG. 9 is a Western blot assay of salivas from 8 subjects with the lectin MAL I.
Figure 10:
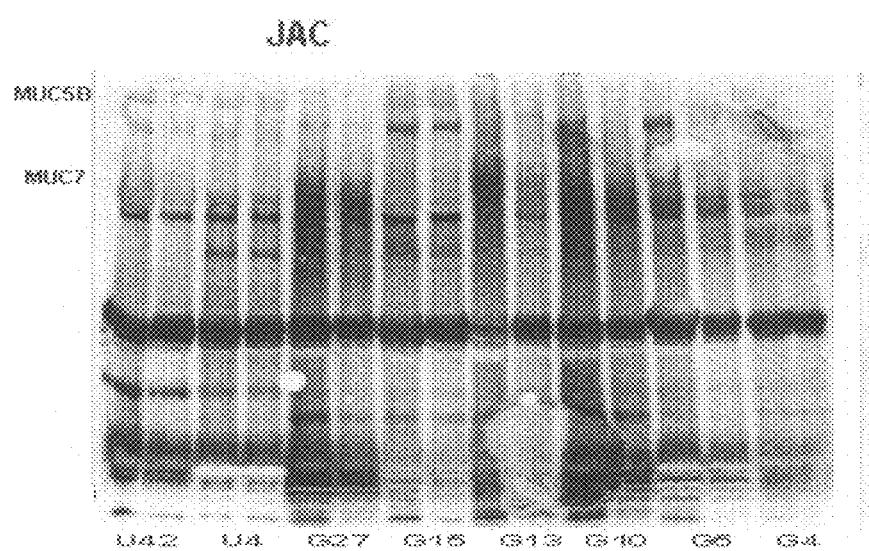
FIG. 10 is a Western blot assay of salivas from 8 subjects with the lectin JAC.
Figure 11:
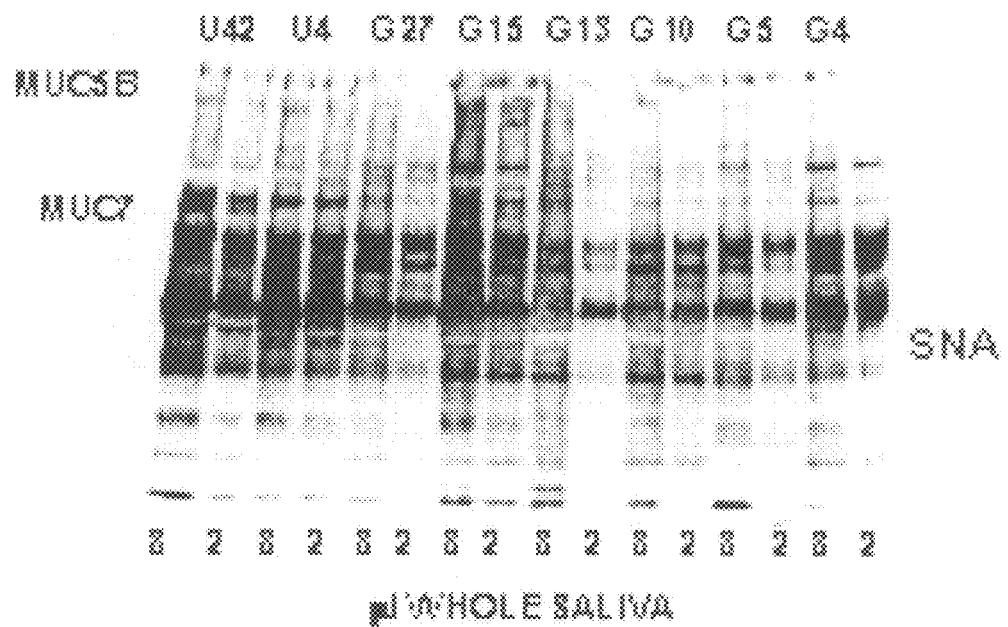
FIG. 11 is a Western blot assay of salivas from 8 subjects with the lectin SNA.

1. Saliva Panel-Dot Blot Assay:

a) This study is a continuation with the same subjects listed in table 3, using an alternative version of the high through-put assay system (HTP) of this invention. A notable advance from this study was the achievement of an all lectin system, i.e., MAL I, JAC, and SNA. When combined with age and ethnicity, this system forecasts DFT (decayed and filled permanent teeth) in the ages 7-26 years-old with an $R^2$ of 0.926 (FIG. 7). While this accomplishment is interesting, it does not have the potential for risk assessment because it tends to put DFT in numerical order rather than to age-appropriate categories. For instance, Aging subject #8 (Table 3) at age 26 with five DFT is in the correct numerical order above Griffin subjects #3 and #4 (Table 3), ages 7 and 8, with four DFT each, though Aging subject #8 (Table 3) is in the low to medium DFT range as an adult and the children appear to be in the highest group for their age. In this and the following analysis, MAL I accounts for more than 50% of the regression equation.

b) In modeling for a system that might be compatible with the earlier young adult study, with high, medium, and low significant ranges, the inventors found that by pairing the same panel of three lectins (MAL I, JAC, and SNA) and gender, an $R^2$ of 0.957 could be achieved (FIG. 8). Interestingly, the model suggests that there are four statistically different groups: high, medium, low, and very low or zero DFT. The possibility of a significant zero category was suggested earlier in the mucin data where the low range of the three-level risk model encompassed three to eight DFT, leaving the zero to two DFT category vacant. There were no subjects with zero DFT in that subject group. In the present lectin-based analysis providing this example, USC subject #42 is 23 years-old with zero caries. This subject's derived numerical value, which uses an age-independent regression equation, is significantly lower than the three children, Griffin subjects #10, #13, and #15 (Table 3), who also have no caries. The regression analysis numerically places these children in a low risk range rather than the zero group, indicating that they will acquire between 2 and 4 DFT by approximately 25 years of age. Another interesting forecast is that Griffin subject #5, a seven year-old with one DFT, actually belongs in the medium risk group (not low), and based on the inventors' earlier study, may be expected to acquire a total of 5 to 8 DFT by 25 years of age. The children in the high risk group are predicted to accumulate 9 or more caries by the age of 25. One conclusion from this study is that with an appropriate age-independent regression equation, predictions in children can be made that forecast the number of caries they will acquire by the time they are young adults, if individualized preventive treatments are not applied.

c) Western blots with the lectins MAL I, JAC, and SNA are shown in FIGS. 9, 10 and 11. The salivas selected for the Western blots represent the extreme combinations of mucin, MAL I, and DFT from the saliva panel. The blot reacted with MAL I illustrates several very important findings. First, not only both mucins, but also other saliva proteins appear to carry the oligosaccharide determinants, even in those salivas with high levels of mucin and no DFT (Griffin subject #15 and USC subject #42; Table 3). Griffin subject #13 had virtually no MUC7 mucin, no cavities, but relatively high MAL I reactivity. The Western blot indicates that the MAL I-reactive oligosaccharides in this saliva are primarily located on salivary glycoproteins intermediate in size between the two mucins, probably the agglutinins. Saliva from Griffin subject #3, with high DFT, also had relatively high mucin levels (Table 3), but it was nearly devoid of the MAL I-reactive oligosaccharides. Griffin subject #10, with no DFT, had relatively low MAL I reactivity, but appeared to make up for this lack by an unusually high level of JAC-reactive oligosaccharides. Both the JAC and SNA Western blots further illustrate the broad distribution of oligosaccharide determinants among salivary proteins, as well as striking individual differences.

d) Continuing to use this panel of salivas for discovery, assays were completed with the following lectins: MAL I, MAL II, SNA, JAC, AAL, AAA, LTL, LPA, MAA, PNA, UEA I, WGA, and PSA. One example of an improvement arising from this set of experiments is that relative to FIG. 7 discussed above, when AAL, UEA I and gender are added and SNA is dropped from the analysis, the $R^2$ improves from 0.926 to 0.990. This study also reaffirms our earlier observation that there may be more than one avenue to achieve the goal of obtaining an $R^2$ of >0.90. In this example, with regard to FIG. 8 discussed above with its $R^2$ of 0.957, a different combination of lectins (MAL I, AAL, JAC, LTL, and PSA) together with gender gives a slightly better $R^2$ of 0.966.

e) As potential standards for the strip test, fetuin and glycophorin were tested against all of the lectins. Glycophorin gave a color reaction with all of the lectins and thus became the standard for comparison of lectin affinities between different individuals, whereas fetuin gave only sporadic results.

Figure 12:
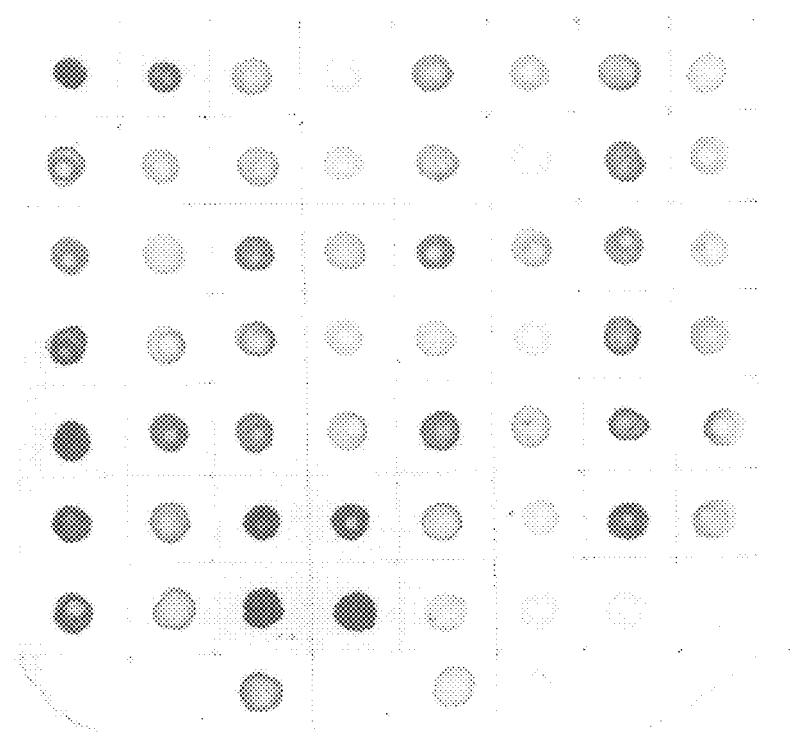
FIG. 12 is a high throughput Western blot assay for SNA reactivity in 0.2 and 0.1 µL, of whole saliva from Griffin Study subjects.
Figure 13:
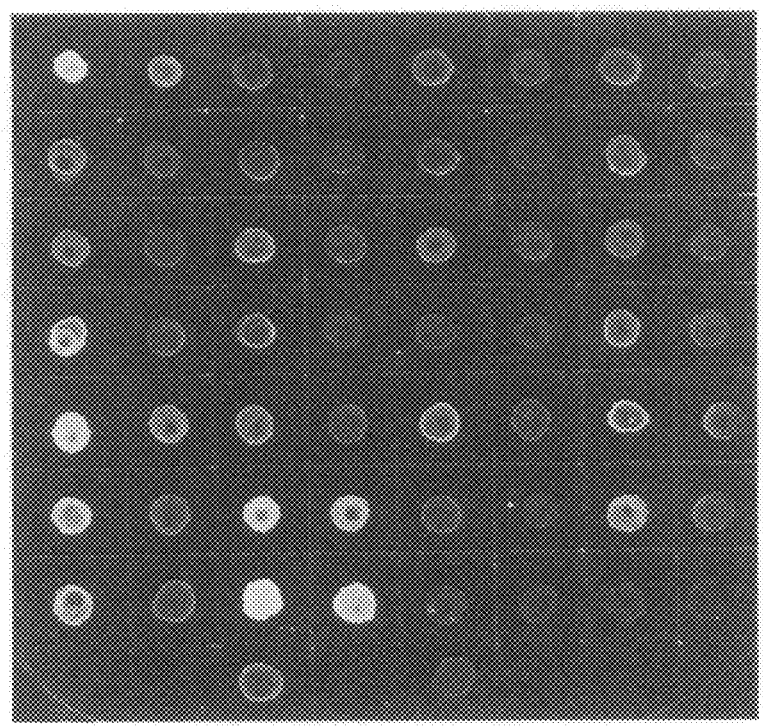
FIG. 13 is a negative image of the Western blot shown in FIG. 12.

2. Revisit of the Griffin Study with Salivas from 7-10 Year-Olds Using the HTP Assay System for MAL I, JAC, SNA, and UEA I FIG. 12 shows the HTP assay blot for SNA with all of the salivas in the data set, including a standard curve. The negative image of the gray scale is shown (FIG. 13), from which the average intensity of each spot is obtained using Sigma Scan Pro (SPSS, Inc.). These intensities were then converted to standardized units based on the standard curve generated from a subset of standards on the same blot. Early in the data analysis, several factors became apparent that greatly impacted the quality of subsequent data analyses. First, children with unerupted permanent molars contributed a lack of direction to the analyses and were subsequently excluded. Secondly, because of the variation in the number of deciduous teeth per individual, a normalized dfs/t was calculated and found to be a major contributor to all subsequent analyses. Some of the more informative analyses included the contributions of dfs/t, age and the various lectins to correlation with DFT or DFS. These analyses suggested that there might be a useful distinction between 7 year-olds and 8-10 year-olds. The contribution of dfs/t to correlation with DFT or DFS declines from 43% in 7 year-olds to 31% in 8-10 year-olds.

3. Additional Studies with Salivas from 7-10 Year-Olds Using the HTP assay system for MAL I, JAC, SNA, and UEA I With regard to the lectins, either MAL I or UEA I, when grouped with gender and dfs/t, yielded promising correlations with DFT, achieving $R^2$ of 0.46 and 0.33, respectively. Separation of the two age groups in the UEA I analysis improved both correlations to an $R^2$ of 0.86 for 8-10 year-olds and 0.43 for 7 year-olds. Separate analyses for the two ethnicities, Hispanic and Chinese (Mandarin-speaking), further illustrate the improvement gained by considering the age groups as different. The Hispanics of all ages gave an $R^2$ of 0.49 for DFT vs. UEA I, gender, and dfs/t, whereas the 7 year-old Hispanics alone had an $R^2$ of 0.88 and the 8-10 year-olds 0.94. The $R^2$ for all of the Chinese children was 0.45, whereas for 7 year-olds alone it was 0.80. There were not enough 8-10 year-old Chinese subjects to complete this comparison. Clearly different regression equations apply to the two age groups. While not wishing to be bound by any particular theory, the inventors believe this reflects the relatively rapid decline in contribution by dfs/t with age and the difference in length of exposure of the permanent teeth.

4. Conclusions a) The caries test can be performed entirely with lectins.

b) The test can be "universalized" by using lectins as evidenced by the work to date with the saliva panel that represents a microcosm of a variety of races and ages.

c) The use of an age-independent regression equation was also demonstrated on the saliva panel. In spite of current DFS, DFS/T, or DFT that were to low to support assignment of risk levels, the children included in the saliva panel could be assigned to risk groups based on numerical values derived from this regression equation, which was influenced heavily by the presence of adults in the analysis. In addition, these risk group assignments provide concrete targets of DFS or DFT that will be reached in adulthood if preventive treatments are not initiated.

d) The companion study, employing young adults, confirmed all of the elements of the 1991 Caucasian study with regard to the correlation of saliva mucins and caries history.

e) The companion study also confirmed that different races may have different relationships of mucins to DFS, as first observed in the Griffin Study of 7-10 year-olds, but that use of lectins in the caries test abolished these differences.

f) Based on the results with the saliva samples from children, it can be concluded that lectin studies with young adults are the source of the age-independent regression equation (s) that can then be applied to children to predict their risk levels.

EXAMPLE 4

Caries Assessment and Risk Evaluation of Permanent Teeth in Young Adults

The dot blots in this study were performed as described in Example 3. This study included more than 70 young adults ranging in ages from 18 to 34 years. The results indicate that of this group, those 24 and older provide a subject pool in which age was not a factor in the analyses of the relationship of lectin affinities in saliva and caries history. Thus, the 24-34 age group was chosen to represent an end-point of the childhood to young adult caries acquisition process in permanent teeth. This age group then also provides the end-point for predictions made on younger ages and the ranges of DFS at each risk level. For FIGS. 14 and 15, resting saliva samples were collected from 21 subjects of different races and genders. Their ages ranged from 24 to 34 years old. Their DFS's ranged from 0 to 36. More than 30 different lectin affinities were sampled.

A revealing observation was that intermediate in the study, three lectins (AAL, LTL, and UEA I) combined to create a highly significant (p=0.006) correlation with DFS with an $R^2$ of 0.51. The significance of this observation is that each lectin is related, to various degrees, to the secretor status of the individual. However, as more oligosaccharide motifs were included in the analysis, the role of secretor status became less prominent and ultimately appeared to have a relatively small (about 10%), but significant (p=<0.001), contribution to a complex web of positive/negative correlations. AAL, LTL, and UEA I also figured prominently in all of our previous studies.

All of the sugar affinities, including secretor status, that are represented in the above mixture of lectins have previously been implicated in the binding or aggregation of various oral microbes (Sharon, N., *Adv. Exp. Med. Biol.* 408:1-8 (1996)).

Figure 14:
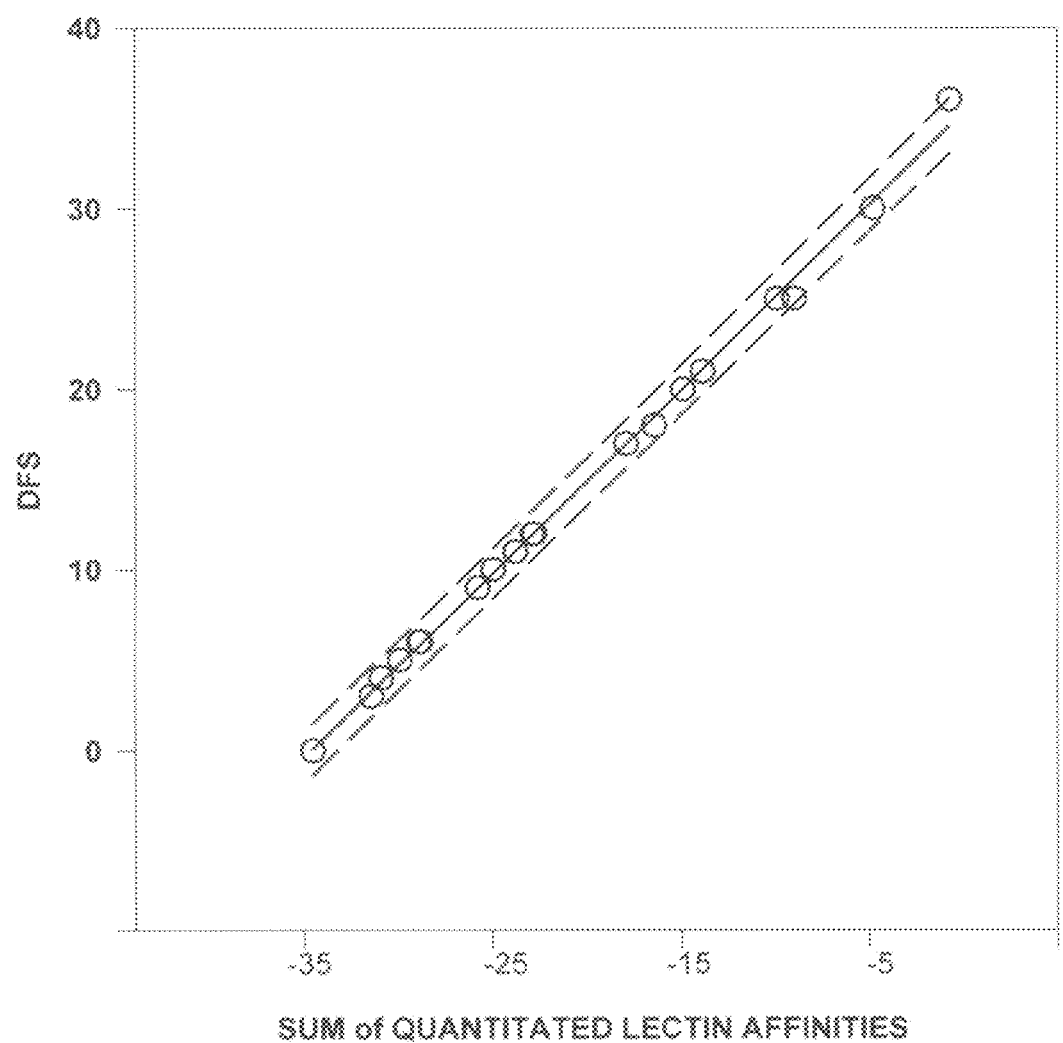
FIG. 14 is a graph showing the relationship of the results from a caries test of this invention to each individual's accumulated caries history. DFS is the dependent variable in this plot.

FIG. 14 shows the relationship of the caries test results to each individual's accumulated caries history. In FIG. 14 the solid line is a plot of the regression equation using DFS as the dependent variable. The quantitated affinities of 19 different lectins were used in the regression equation. The $R^2$ (Coefficient of Determination) is 1.00. The significance is p=<0.001. The dashed lines enclose the Population Confidence Interval at 98%, which is also known as the Confidence Interval of Prediction.

Figure 15:
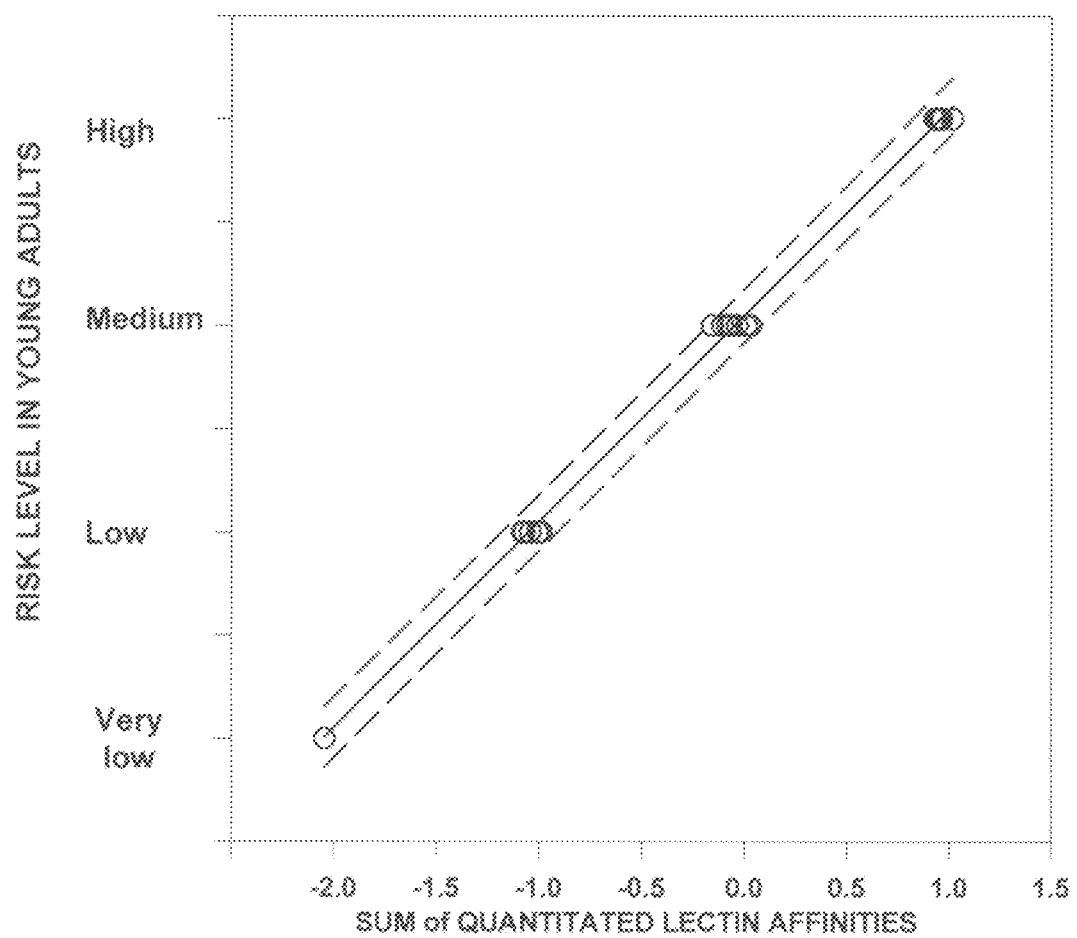
FIG. 15 is a graph showing the relationship between risk level in young adults versus the sum of quantitated lectin affinities.

FIG. 15 shows the assignment of risk levels to different ranges of DFS, and the ability of the lectin-based test to yield a robust regression equation using risk levels as the dependent variable. For FIG. 15, the significance (p) and Confidence Interval of Prediction are the same as for FIG. 14, however $R^2$ is slightly less at 0.998. A modified combination of lectin affinities was also needed in order to achieve the "best" results for FIG. 15. The ranges of DFS that were selected were 0-2 DFS for very low risk, 3-8 DFS for low risk, 9-16 DFS for medium risk, and 17 or more DFS for high risk. Statistically valid results were obtained with as many as 12 different risk levels.

EXAMPLE 5

Caries Assessment and Risk Evaluation of Deciduous Teeth in Children

The focus on the 7-10 year-olds in this study is very important for three reasons. First, this is the usual time that sealants are applied to the permanent molars, and the results of the caries risk test can provide the rationale for application of this preventive treatment on an individual basis. Secondly, this is the age where statistical correlates between caries history (DFS/T) or risk level in permanent teeth and the caries assessment test first become evident and can be linked with specific and predictable outcomes in young adults. Finally, this age group represents an end-point of caries history for the deciduous teeth.

Figure 16:
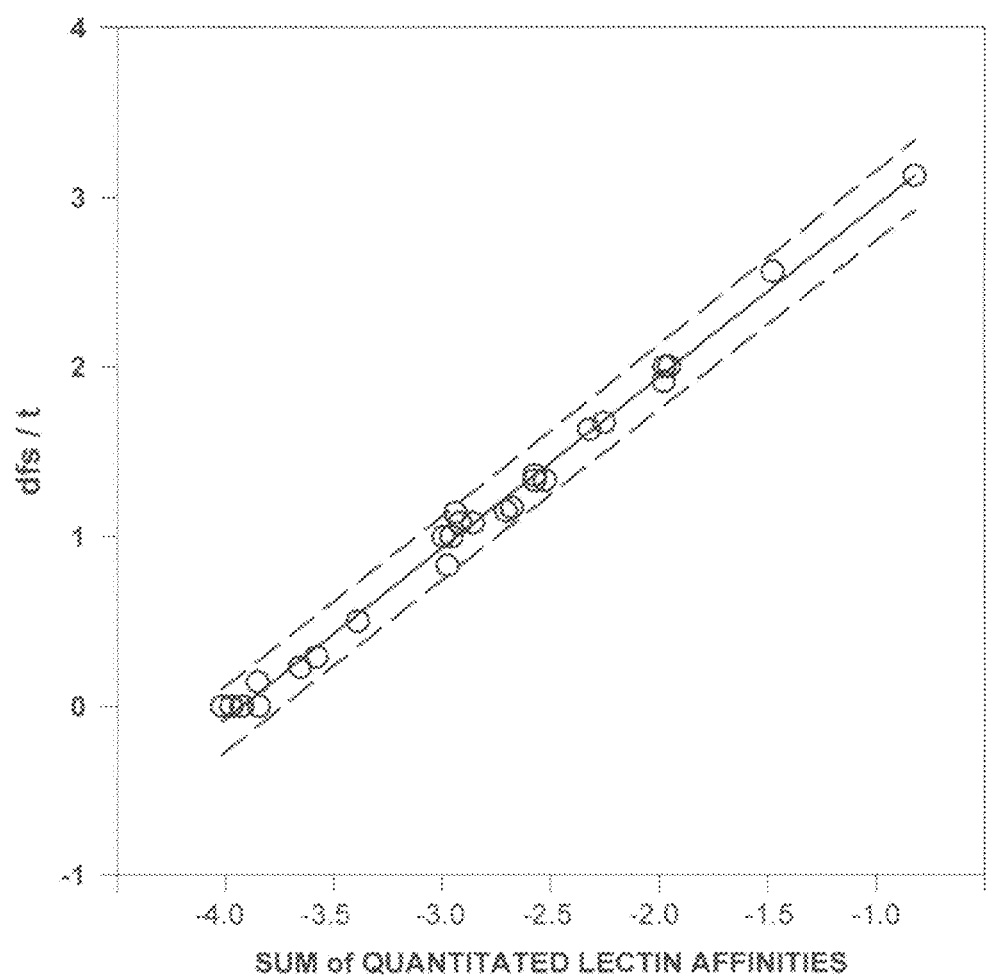
FIG. 16 is a graph showing the relationship of dfs/t (number of deciduous caries per remaining deciduous teeth) and the sum of quantitated lectin affinities.
Figure 17:
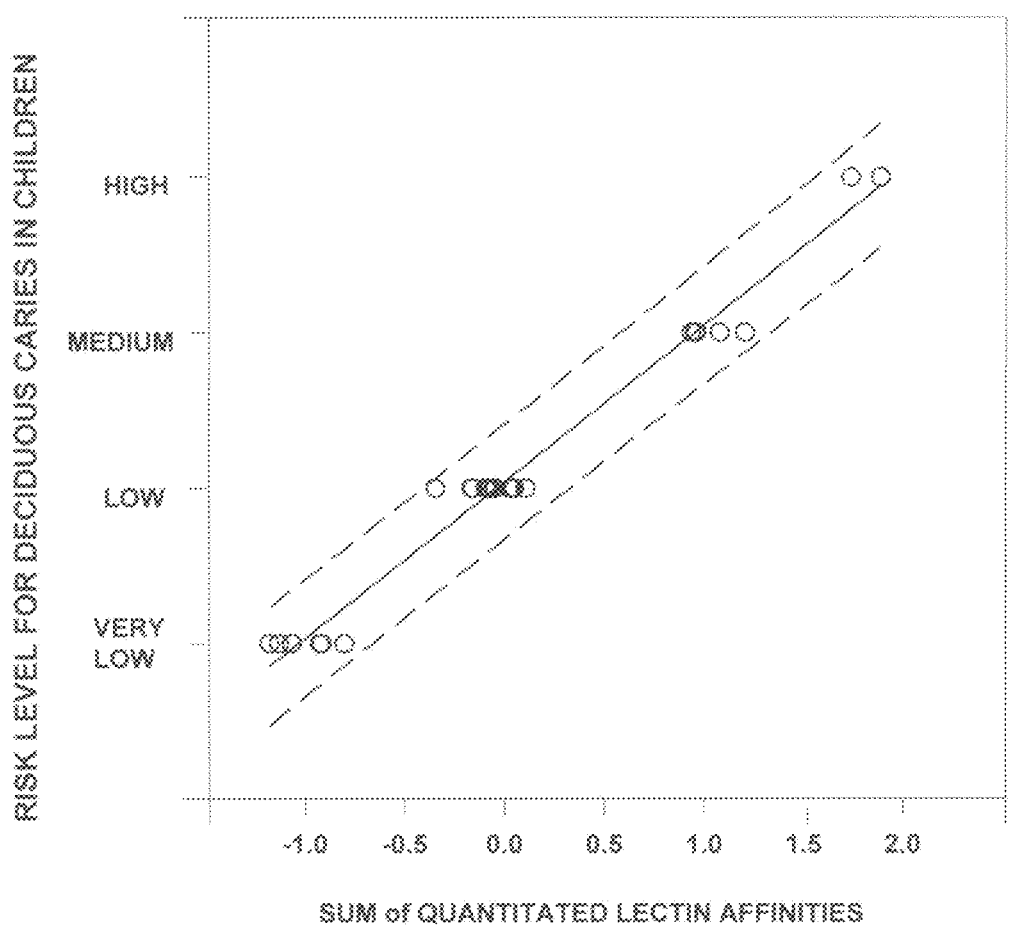
FIG. 17 is a graph showing the relationship of the risk level for deciduous caries in children and the sum of quantitated lectin affinities.

The dot blots in this study were performed as described in Example 3. The number of children in this group is 27, with an approximate equal distribution of males and females and Hispanic and Chinese, ranging in ages from 7-10 years. Though the number of remaining deciduous teeth varies among individuals, the accumulated caries history of the deciduous teeth is represented in this age group as the endpoint of caries development in deciduous teeth. FIGS. 16 and 17 illustrate that the caries test can accurately assess the number of remaining caries, and translates that into statistically significant risk levels.

FIG. 16 shows the relationship of the caries test results to each individual's accumulated caries history. FIG. 16 uses dfs/t as its dependent variable in order to accommodate the individual differences in the number of remaining deciduous teeth. The range of remaining caries was from 0 per tooth to 3 per tooth. The test itself required the input of 21 different lectin affinities. The $R^2$ is 0.996 with a significance of p=0.001. The Confidence Interval of Prediction was maintained at 98%. FIG. 17 shows the assignment of risk levels to different ranges of dfs/t, and the ability of the lectin-based test to yield a robust regression equation using risk levels as the dependent variable.

FIG. 17 illustrates the ability of the caries test to translate the caries assessment information into four risk levels based ranges of dfs/t. Though the Confidence Interval of Prediction at 98% is broader than in FIG. 16, there are still four non-overlapping zones of significance that assign all of the subjects into their appropriate risk levels. The regression equation graphed in FIG. 17 has an $R^2$ of 0.980, and is significant at p=<0.001. The ranges of dfs/t that were selected were 0-0.35 dfs/t for very low risk, 0.36-1.35 dfs/t for low risk, 1.36-2.00 dfs/t for medium risk, and 2.01 dfs/t or more for high risk.

EXAMPLE 6

Figure 18:
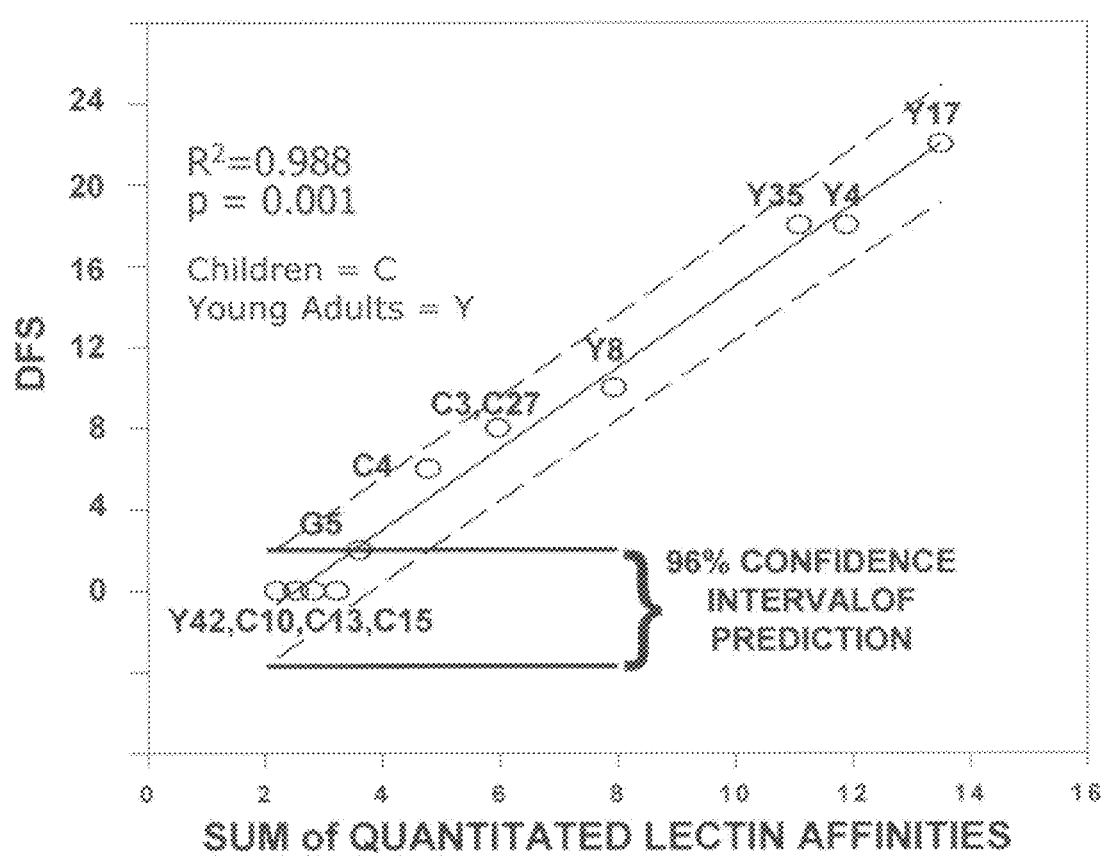
FIG. 18 describes a linear regression analysis of DFT versus the sum of quantitated lectin affinities with representative 96% confidence levels in a mixed group of children and adults.

Caries Assessment and Risk Evaluation of Permanent Teeth in a Mixed Population of Children and Young Adults This study provides a model for prediction of future caries development in children. The dot blots in this study were performed as described in Example 3. The test group was comprised of 12 subjects, half of which are young adult Asians and Caucasians and the other half is divided between Chinese and Hispanic 7-9 year-old children. There were approximately equal numbers of males and females. The age range of the group was 7-26 years-old. FIG. 18 was derived from a regression equation that included age of the individual, as well as the results of the lectin-based tests as independent variables. Comparison of FIG. 18 with FIG. 7 shows the improvements embodied in the caries risk test over time in a mixed population of children and adults.

FIG. 18 shows that when age is factored in as an independent variable, the lectin-based caries test can accurately assess DFS in a broad range of ages. The rationale for prediction of future caries development is based on the idea that risk levels are first derived from a young adult group of subjects that represents an end-point for caries development, such as was done in FIG. 14.

Figure 19:
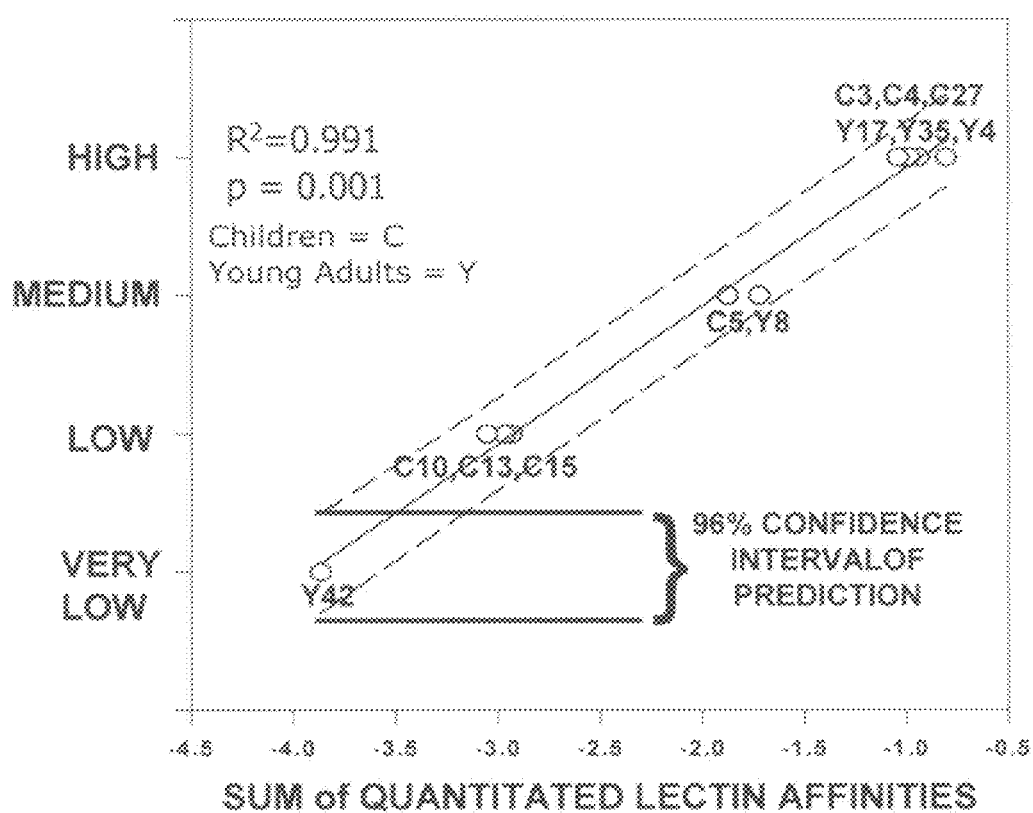
FIG. 19 describes a linear regression analysis of risk level for children and young adults versus the sum of quantitated lectin affinities with representative 96% confidence levels.

FIG. 19 shows that age is no longer a factor and the regression equation was generated by the lectin-based tests on young adults, as were the risk levels. The lectin-based data for the children was analyzed by the adult-derived equation to yield the observed risk levels. FIG. 19 shows that when the caries test data from the children is processed by the adult-derived regression equation, the children are then assigned to specific risk levels. The ranges for the different risk levels in FIGS. 18 and 19 are the same as those above, i.e., 0-2 DFS for very low risk, 3-8 DFS for low risk, 9-16 DFS for medium risk, and 17 or more DFS for high risk. The interpretation from this application of the caries test is that even though some of the children in this group have no caries on their permanent teeth, the test suggests that they will acquire 3-8 by the time they are approximately 25 years-old. The test also suggests that the child with one DFS will acquire from 8 to 15 more caries by age 25. The high risk children are targeted to accumulate 17 or more DFS by the age of 25. Comparison of FIG. 19 with FIG. 8 illustrates the improvement in the prediction potential of the caries risk test.

EXAMPLE 7

Colored Microbead Assays

Figure 20:
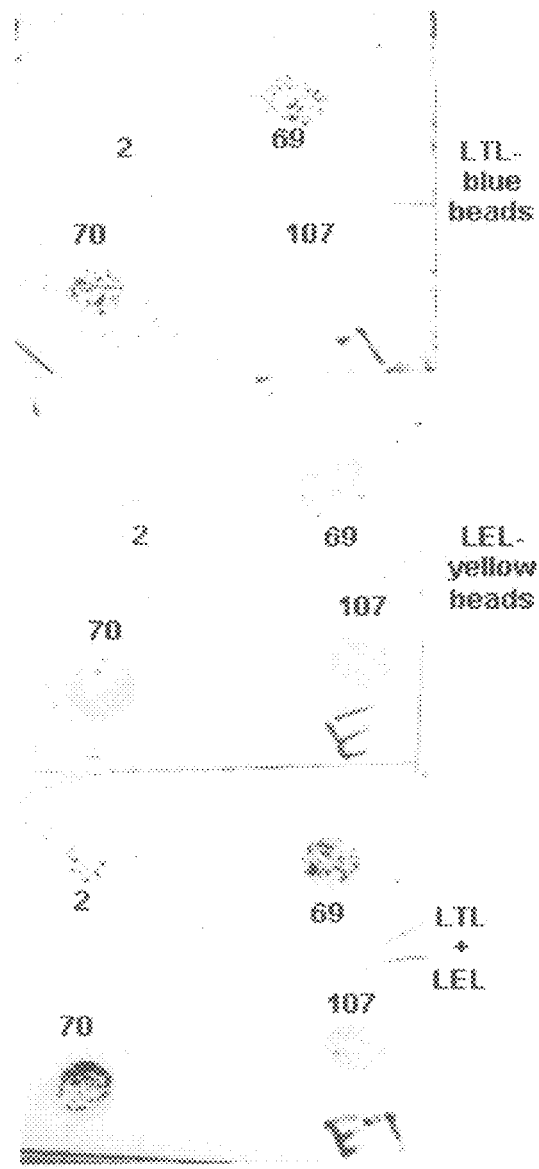
FIG. 20 is a Western blot assay of salivas with lectins LTL and LEL conjugated to blue and yellow colored mierolatex beads, respectively.

FIG. 20 illustrates the use of the blue-yellow bead model to express intermediate ratios of two lectins as green while still preserving the end points of the color scale. LTL and LEL were derivatized directly to blue and yellow microlatex beads, respectively. To accomplish the test itself, the concentrations of derivatized beads were first calibrated separately on saliva samples that represented the population range of affinities observed on the dot blot assay. This is shown on the top two tests of FIG. 20. The beads were then mixed to achieve the calibrated concentrations, and the suspension was overlaid on the membrane containing 5 mL spots of dried saliva. Binding was rapid and appeared to be limited by bead settling times.

The bottom of FIG. 20 shows the full range of colors. In the regression equation that is illustrated with these saliva samples, LTL is positively correlated with DFS, and LEL is negatively correlated with DFS. In FIG. 20, the numbers represent saliva samples from different students. The colors coincide with the following DFS for this group: #2-34 DFS, #69-20 DFS, #70-17 DFS, and #107-5 DFS. Student #2 has a very high ratio of LTL to LEL affinities, but even at low concentrations of each, the color on the test strip is blue. Students #69 and #70 also have relatively high rations, >10:1, but since the test was been calibrated to see this as an intermediate ratio, the color on the test strip is green. Student #107 has a ratio of 0.46:1 of LTL:LEL, i.e., a very low ratio of LTL to LEL, and the color on the test strip is yellow. The color test appears to preserve the ratio of positive to negative affinities, in spite of over-all concentration differences between saliva samples.

Figure 21:
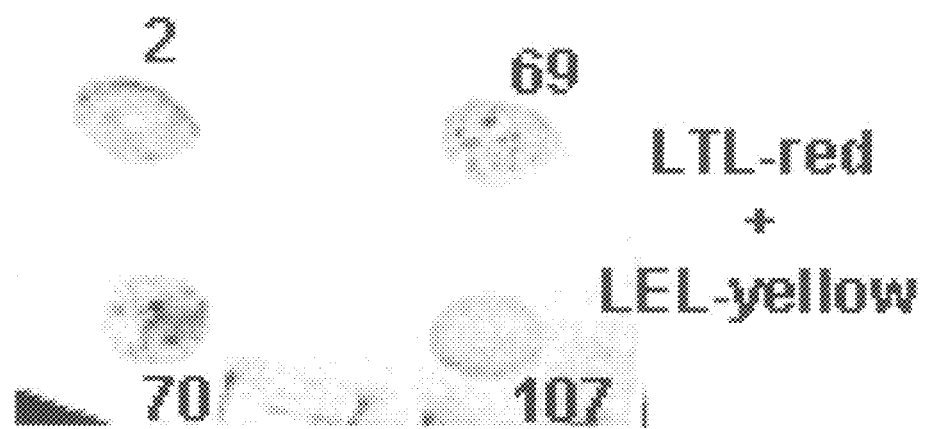
FIG. 21 is a Western blot assay of salivas with lectins LTL and LEL conjugated to red and yellow colored microlatex beads, respectively.

As an alternative, the red-yellow combination was also tested with the same lectins and saliva samples. Like the above test, the two end colors formed the intermediate color (orange), which dominated at most ratios of the two lectins (Figure 21). A weakness of both color combinations is the difficulty of visualizing the pure yellow color against the white background. As an alternative, LEL was conjugated to a mixture of red and yellow beads, producing the easier-to-see orange. The most recent color endpoints are blue and orange with intermediate colors that are still predominantly shades of green. As noted above, each test will have a range of standards covalently linked to the test strip to produce the different colors associated with each risk level.

EXAMPLE 8

Permissive and Preventive Oligosaccharide Motifs Suggested by the Lectin Affinity Studies This study was to determine the most important oligosaccharide motifs sampled for the test. The strategy was to search for the convergence of correlations between lectin affinities in the context of their individual significant positive or negative correlations with DFS using the most recent group of student saliva samples.

The two main core motifs that emerged are Fucα-1,2Gal-GlcNAc (also known as the H antigen, which is usually associated with the secretor positive trait) and ±Galαorβ-1,3GalNAcα orβ. In short, these oligosaccharide motifs when not sialylated were permissive, i.e., positively correlated with DFS, but when sialylated either by α-2,3 or α-2,6 sialic acid, they were preventive, i.e., negatively correlated with DFS. The one exception is that ±Galα-1,3GalNAcβ also appears to be preventive whether or not it is sialylated. The third motif that appears to be important in the test is chitobiose or chitotriose ($GlcNAc_{(2 \text{ or } 3)}$). This also shifted from permissive to preventive upon sialylation. In addition, when the chitobiose segment is α-fucosylated, which is likely to include the $Lewis_a$ antigen, it appears to be preventive regardless of sialylation.

It is also noteworthy that while six of the 21 students in the 24-34 year-old group are non-secretors as judged by very low levels of UEA affinities, the H antigen motif was equally important to the test regardless of its absolute concentration even in the non-secretors, all of whom still had measurable amounts of UEA affinity binding. This analysis affirms that the ratios of lectin affinities are more important to the test than the absolute affinity-based concentrations.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method for predicting the risk of disease in a subject, said method comprising:
    obtaining an unfractionated saliva sample from said subject;
    contacting an aliquot of said saliva with two or more lectins under conditions that allow said two or more lectins to bind to two or more respective lectin-binding components of said saliva;
    detecting the amounts of bound lectins; and
    comparing the amounts of bound lectins to the respective amounts known to bind a saliva sample from a control subject, wherein the amounts of bound lectins are indicative of the risk of said disease.

2. The method of claim 1, wherein said saliva sample is an unstimulated saliva sample.

3. The method of claim 1, wherein said lectin-binding components are oligosaccharides.

4. The method of claim 1, wherein the two or more lectins are selected from the group consisting of DSL (*datura stramonium*), ECL (erythrina cristagalli), PSA (*pisum sativum*), WGA (*triticum* vulgaris), UEA I (*ulex europaeus*), MAL I (*maackia amurensis*), MAA (*maackia amurensis*), PNA (*arachis hypogaea*), AAL (aleuria aurantia), LTL (lotus tetragonolobus), MAL II (*maackia amurensis*), JAC (*Artocarpus* integrifolia), LEL (*lycopersicon esculentum*), SNA (*sambucus nigra*), PTL I (psophocarpus tetrogonolobus), ACL (*amaranthus caudatus*), GSL II (griffonia simplicifolia), VVA (*vicia* villosa), BPL (*bauhinia purpurea*), WFL (*wisteria floribunda*), SJA (*sophora japonica*), MPL (maclura pomifera), GNL (*galanthus nivalis*), HHL (hippeastrum hybrid), CCA (*canavalia ensiformis*), NPL (*narcissus pseudonarcissus*), STL (*solanum* tuberosum), PHA-L (*phaseolus* vulgaris), PHA-E (*phaseolus* vulgaris), GSL I (griffonia simplicifolia), DBA (*dolichos biflorus*), HMA (homarus americanus), EEA (euonymous europaeus), LPA (*limulus polyphemus*), and PTL II (psophocarpus tetrogonolobus).

5. The method of claim 4, wherein the two or more lectins include MAL I.

6. The method of claim 1, further comprising assessing the risk of said disease at a defined level.

7. The method of claim 1, further comprising assessing the risk of said disease as high, medium, low, or very low.

8. The method of claim 1, further comprising assessing the risk of future development of said disease in said subject.

9. The method of claim 8, wherein said assessing comprises comparing the amount of binding to a regression analysis derived from a group of subjects expressing a range of disease severity.

10. The method of claim 1, wherein said contacting and said detecting are part of a Western blot procedure.

11. The method of claim 10, wherein said contacting comprises:
    applying a drop of said saliva to a matrix material; and
    contacting the matrix with a solution containing said two or more lectins.

12. The method of claim 10, wherein said two or more lectins are each coupled to a reporter selected from the group consisting of dyes, chemiluminescent compounds, enzymes, fluorescent compounds, biotin, haptens, radioluminescent compounds, and radioactive-labeled biomolecules.

13. The method of claim 10, wherein said detecting comprises contacting a matrix with a visualizing stain.

14. The method of claim 11, wherein said contacting comprises:
    contacting the matrix with a mixture of a first set of lectins conjugated to a microparticle having a first color and a second set of lectins conjugated to a microparticle having a second color, wherein said first and second colors are distinguishable from one another.

15. The method of claim 11, further comprising applying a drop of saliva from a control subject to said matrix.

16. The method of claim 10, wherein said procedure comprises:
    applying said two or more lectins to a surface of a matrix material; and
    contacting the matrix material with said saliva sample under conditions that allow the lectin-binding component to bind to the two or more lectins.

17. The method of claim 16, wherein said two or more lectins comprise a first set of lectins and a second set of lectins, said first and second sets of lectins being distinguishable from one another.

18. The method of claim 16, wherein said detecting comprises contacting said matrix material with a binding partner coupled to a reporter, wherein said binding partner specifically binds said lectin-binding component.

19. The method of claim 18, wherein said binding partner is an antibody or a lectin.

20. The method of claim 18, wherein said reporter is selected from the group consisting of dyes, chemiluminescent compounds, enzymes, fluorescent compounds, biotin, haptens, radioluminescent compounds, and radioactive-labeled biomolecules.

21. The method of claim 1, wherein said subject is a human.

22. The method of claim 1, wherein said disease is selected from the group consisting of dental caries, periodontal diseases, pulmonary diseases, respiratory diseases, cardiovascular diseases, diabetes, perinatal disorders, mucosal infections, oral cancers, pharyngeal cancers, precancerous lesions, associated autoimmune disorders, HIV, and osteoporosis, and a combination thereof.

23. A method for preventing or reducing the risk of a disease, the method comprising:
    obtaining an unfractionated saliva sample from a subject;
    contacting an aliquot of said saliva with two or more lectins under conditions that allow said two or more lectins to bind respectively to two or more lectin-binding components of said saliva;
    detecting the amounts of bound lectins;
    comparing the amounts of bound lectins to the respective amounts known to bind a saliva sample from a control subject, wherein the amounts of bound lectins are proportional to the risk of a disease in said subject; and
    administering a therapeutic reagent to said subject when the content of the components in said saliva are above or below the respective levels contained in a normal control.

24. A kit for detecting disease, the kit comprising:
    means for collecting a saliva sample;
    means for measuring the amounts of two or more lectin-binding components in said sample; and
    an oral fluid standard for comparing with the amounts of said components in said sample.

25. The kit of claim 24, wherein said disease is selected from the group consisting of dental caries, periodontal diseases, pulmonary diseases, respiratory diseases, cardiovascular diseases, diabetes, perinatal disorders, mucosal infections, oral cancers, pharyngeal cancers, precancerous lesions, associated autoimmune disorders, HIV, and osteoporosis, and a combination thereof.

26. The kit of claim 24, further comprising a matrix material, and wherein the kit is configured to detect each of the lectin-binding components by carrying out a Western blot analysis.

* * * * *